(12) United States Patent
Garza et al.

(10) Patent No.: US 11,964,109 B2
(45) Date of Patent: Apr. 23, 2024

(54) SYSTEMS AND METHODS FOR DRIVING NEURAL ACTIVITY TO CONTROL BRAIN SIGNALING AND GENE EXPRESSION

(71) Applicants: GEORGIA TECH RESEARCH CORPORATION, Atlanta, GA (US); EMORY UNIVERSITY, Atlanta, GA (US)

(72) Inventors: Kristie Michelle Garza, Decatur, GA (US); Annabelle C. Singer, Atlanta, GA (US); Levi Wood, Atlanta, GA (US); Abigail L. Paulson, Atlanta, GA (US)

(73) Assignees: Georgia Tech Research Corporation, Atlanta, GA (US); Emory University, Atlanta, GA (US)

(*) Notice: Subject to any disclaimer, the term of this patent is extended or adjusted under 35 U.S.C. 154(b) by 672 days.

(21) Appl. No.: 16/979,226

(22) PCT Filed: Mar. 11, 2019

(86) PCT No.: PCT/US2019/021701
§ 371 (c)(1),
(2) Date: Sep. 9, 2020

(87) PCT Pub. No.: WO2019/173847
PCT Pub. Date: Sep. 12, 2019

(65) Prior Publication Data
US 2020/0398021 A1  Dec. 24, 2020

Related U.S. Application Data
(60) Provisional application No. 62/648,472, filed on Mar. 27, 2018, provisional application No. 62/640,736, filed on Mar. 9, 2018.

(51) Int. Cl.
*A61M 21/00* (2006.01)
*A61N 2/00* (2006.01)
*A61N 1/36* (2006.01)

(52) U.S. Cl.
CPC .............. *A61M 21/00* (2013.01); *A61N 2/006* (2013.01); *A61M 2021/0027* (2013.01);
(Continued)

(58) Field of Classification Search
CPC .......... A61M 21/00; A61M 2021/0027; A61M 2021/0044; A61N 5/0622
See application file for complete search history.

(56) References Cited

U.S. PATENT DOCUMENTS 5,599,274 A * 2/1997 Widjaja ................ A61M 21/00
                                                            600/26
9,629,976 B1 * 4/2017 Acton ...................... A61H 5/00
(Continued)

FOREIGN PATENT DOCUMENTS

EP  2272561 A1   1/2011
GB  2352182 A *  1/2001  ............ A61M 21/00

OTHER PUBLICATIONS

Allan, S. M. & Rothwell, N. J. Cytokines and acute neurodegeneration. Nat. Rev. Neurosci. 2, 734-44 (2001).
(Continued)

*Primary Examiner* — Kaylee R Wilson
(74) *Attorney, Agent, or Firm* — Meunier Carlin & Curfman LLC

(57) ABSTRACT

Methods for controlling brain activity in a subject are described herein. An example method can include delivering a stimulus to the subject, wherein the stimulus induces neural activity in the subjects brain and modulates expression of at least one soluble mediator of cellular activity (such as, for example, a cytokine, chemokine, and/or growth
(Continued)

factor) within the subject, and the stimulus is delivered to the subject for less than one hour.

30 Claims, 43 Drawing Sheets

(52) U.S. Cl.
CPC ............... *A61M 2021/0044* (2013.01); *A61M 2021/0055* (2013.01); *A61M 2021/0072* (2013.01); *A61M 2250/00* (2013.01); *A61N 1/36025* (2013.01)

(56) References Cited

U.S. PATENT DOCUMENTS

| | | | |
|---|---|---|---|
| 2006/0047324 A1* | 3/2006 | Tass ..................... | A61M 21/00 607/45 |
| 2008/0262287 A1 | 10/2008 | Dussau | |
| 2012/0101327 A1 | 4/2012 | Dissing et al. | |
| 2013/0184792 A1 | 7/2013 | Simon et al. | |
| 2015/0174418 A1* | 6/2015 | Tyler ....................... | A61N 7/00 607/45 |
| 2015/0367133 A1 | 12/2015 | Schiff et al. | |
| 2016/0362692 A1 | 12/2016 | MacLaren et al. | |
| 2017/0080246 A1 | 3/2017 | Knight | |
| 2017/0143934 A1 | 5/2017 | Tsai et al. | |
| 2017/0304584 A1 | 10/2017 | Tsai et al. | |
| 2020/0269065 A1* | 8/2020 | Broeng ................ | A61N 5/0618 |

OTHER PUBLICATIONS

Axmacher, N., Elger, C. E. & Fell, J. Ripples in the medial temporal lobe are relevant for human memory consolidation. Brain 131, 1806-17 (2008).
Bahrami, S. & Drabløs, F. Gene regulation in the immediate-early response process. Adv. Biol. Regul. 62, 37-49 (2016).
Bennett, B. L. et al. SP600125, an anthrapyrazolone inhibitor of Jun N-terminal kinase. Proc. Natl. Acad. Sci. U. S. A. 98, 13681-6 (2001).
Buzsaki, G. et al. Hippocampal network patterns of activity in the mouse. Neuroscience 116, 201-211 (2003).
Camer, D et al. Bardoxolone methyl prevents high-fat diet-induced alterations in prefrontal cortex signalling molecules involved in recognition memory. Prog. Neuro-Psychopharmacology Biol. Psychiatry 59, 68-75 (2015).
Carr, M. F. F. F., Karlsson, M. P. P. P. & Frank, L. M. M. M. Transient Slow Gamma Synchrony Underlies Hippocampal Memory Replay. Neuron 75, 700-713 (2012).
Carr, M. F., Jadhav, S. P. & Frank, L. M. Hippocampal replay in the awake state: a potential substrate for memory consolidation and retrieval. Nat. Neurosci. 14, 147-153 (2011).
Clemens, Z. et al. Temporal coupling of parahippocampal ripples, sleep spindles and slow oscillations in humans. Brain 130, 2868-78 (2007).
Colgin, L. L. Rhythms of the hippocampal network. Nat. Rev. Neurosci. 17, 239-249 (2016).
Dansokho, C. & Heneka, M. T. Neuroinflammatory responses in Alzheimer's disease. J. Neural Transm. (2017). doi:10.1007/s00702-017-1831-7.
Dombeck, D. A. & Reiser, M. B. Real neuroscience in virtual worlds. Curr. Opin. Neurobiol. 22, 3-10 (2012).
Dragoi, G. & Buzsaki, G. Temporal Encoding of Place Sequences by Hippocampal Cell Assemblies. Neuron 50, 145-157 (2006).
Elmore, M. R. P. et al. Colony-Stimulating Factor 1 Receptor Signaling Is Necessary for Microglia Viability, Unmasking a Microglia Progenitor Cell in the Adult Brain. Neuron 82, 380-397 (2014).
Foster, D. J. & Wilson, M. A. Reverse replay of behavioural sequences in hippocampal place cells during the awake state. Nature 440, 680-3 (2006).

Fries, P., Nikolić, D. & Singer, W. The gamma cycle. Trends Neurosci. 30, 309-16 (2007).
Gierut, J. J. et al. Network-level effects of kinase inhibitors modulate TNF-alpha-induced apoptosis in the intestinal epithelium. Sci Signal 8, ra129 (2015).
Gillespie, A. K. et al. Apolipoprotein E4 Causes Age-Dependent Disruption of Slow Gamma Oscillations during Hippocampal Sharp-Wave Ripples. Neuron 1-12 (2016). doi:10.1016/j.neuron.2016.04.009.
Girardeau, G. & Zugaro, M. Hippocampal ripples and memory consolidation. Curr. Opin. Neurobiol. 21, 452-459 (2011).
Girardeau, G., Benchenane, K., Wiener, S. I., Buzsáki, G. & Zugaro, M. B. Selective suppression of hippocampal ripples impairs spatial memory. Nat. Neurosci. 12, 1222-1223 (2009).
Hanisch, U.-K. Microglia as a source and target of cytokines. Glia 40, 140-55 (2002).
Hasselmo, M. E. & Stern, C. E. Theta rhythm and the encoding and retrieval of space and time. Neuroimage 85 Pt 2, 656-66 (2014).
Iaccarino, H. F. et al. Gamma frequency entrainment attenuates amyloid load and modifies microglia. Nature (2016).
Jadhav, S. P., Kemere, C., German, P. W. & Frank, L. M. Awake hippocampal sharp-wave ripples support spatial memory.e. Science (80-. ). 336, 1454-8 (2012).
Janes, K. A. et al. A systems model of signaling identifies a molecular basis set for cytokine-induced apoptosis. Science 310, 1646-1653 (2005).
Kaminska, B. MAPK signalling pathways as molecular targets for anti-inflammatory therapy—from molecular mechanisms to therapeutic benefits. Biochim. Biophys. Acta 1754, 253-62 (2005).
Karlsson, M. P. & Frank, L. M. Awake replay of remote experiences in the hippocampus. Nat. Neurosci. 12, 913-8 (2009).
Keren-Shaul, H. et al. A Unique Microglia Type Associated with Restricting Development of Alzheimer's Disease. Cell 169, 1276-1290.e17 (2017).
Logothetis, N. K. et al. Hippocampal-cortical interaction during periods of subcortical silence. Nature 491, 547-553 (2013).
Nakazawa, K., McHugh, T. J., Wilson, M. A. & Tonegawa, S. NMDA receptors, place cells and hippocampal spatial memory. Nat. Rev. Neurosci. 5, 361-372 (2004).
O'Keefe, J. & Dostrovsky, J. The hippocampus as a spatial map. Preliminary evidence from unit activity in the freely-moving rat. Brain Research 34, 171-175 (1971).
Onai, Y. et al. Inhibition of IkappaB phosphorylation in cardiomyocytes attenuates myocardial ischemia/reperfusion injury. Cardiovasc. Res. 63, 51-9 (2004).
Rajasethupathy, P. et al. Projections from neocortex mediate top-down control of memory retrieval. Nature 526, 653-659 (2015).
Rangaraju, S. et al. A systems pharmacology-based approach to identify novel Kv1.3 channel-dependent mechanisms in microglial activation. J. Neuroinflammation 14, 128 (2017).
Ravassard, P. et al. Multisensory control of hippocampal spatiotemporal selectivity. Science (80-. ). 340, 1342-6 (2013).
Rehman, S. U. et al. Inhibition of c-Jun N-Terminal Kinase Protects Against Brain Damage and Improves Learning and Memory After Traumatic Brain Injury in Adult Mice. Cereb. Cortex 1-19 (2017). doi:10.1093/cercor/bhx164.
Rothschild, D. E., McDaniel, D. K., Ringel-Scaia, V. M. & Allen, I. C. Modulating inflammation through the negative regulation of NF-κB signaling. J. Leukoc. Biol. (2018). doi:10.1002/JLB.3MIR0817-346RRR.
Seyfried, N. T. et al. A Multi-network Approach Identifies Protein-Specific Co-expression in Asymptomatic and Symptomatic Alzheimer's Disease. Cell Syst. 4, 60-72.e4 (2017).
Singer, A. C. & Frank, L. M. Rewarded outcomes enhance reactivation of experience in the hippocampus. Neuron 64, 910-21 (2009).
Singer, A. C., Carr, M. F., Karlsson, M. P. & Frank, L. M. Hippocampal SWR activity predicts correct decisions during the initial learning of an alternation task. Neuron 77, 1163-73 (2013).
Skaggs, W. & McNaughton, B. Replay of neuronal firing sequences in rat hippocampus during sleep following spatial experience—ProQuest. Science (80-. ). 271, 1870 (1996).

(56) References Cited

OTHER PUBLICATIONS

Stam, C. J. et al. Generalized Synchronization of MEG Recordings in Alzheimer's Disease: Evidence for Involvement of the Gamma Band. J. Clin. Neurophysiol. 19, 562-574 (2002).
Tischer, J. et al. Inhomogeneous distribution of Iba-1 characterizes microglial pathology in Alzheimer's disease. Glia 64, 1562-1572 (2016).
Trapnell, C., Pachter, L. & Salzberg, S. L. TopHat: discovering splice junctions with RNA-Seq. Bioinformatics 25, 1105-1111 (2009).
Verret, L. et al. Inhibitory Interneuron Deficit Links Altered Network Activity and Cognitive Dysfunction in Alzheimer Model. Cell 149, 708-721 (2012).
Wang, Y.-Y., Yang, Y.-X., Zhe, H., He, Z.-X. & Zhou, S.-F. Bardoxolone methyl (CDDO-Me) as a therapeutic agent: an update on its pharmacokinetic and pharmacodynamic properties. Drug Des. Devel. Ther. 8, 2075-88 (2014).
Wood, L. B. et al. Identification of neurotoxic cytokines by profiling Alzheimer's disease tissues and neuron culture viability screening. Sci Rep 5, 16622 (2015).
Wood, L. B., Winslow, A. R. & Strasser, S. D. Systems biology of neurodegenerative diseases. Integr Biol 7, 758-775 (2015).
Zhang, B. & Horvath, S. A general framework for weighted gene co-expression network analysis. Stat. Appl. Genet. Mol. Biol. 4, Article17 (2005).
Araujo, D. M., & Cotman, C. W. (1993). Trophic effects of interleukin-4, -7 and -8 on hippocampal neuronal cultures: potential involvement of glial-derived factors. Brain Research, 600(1), 49-55.
Araujo, D. M., & Lapchak, P. A. (1994). Induction of immune system mediators in the hippocampal formation in Alzheimer's and Parkinson's diseases: selective effects on specific interleukins and interleukin receptors. Neuroscience, 61(4), 745-754.
Balasingam, V., & Yong, V. W. (1996). Attenuation of astroglial reactivity by interleukin-10. Journal of Neuroscience, 16(9), 2945-2955.
Baron, P., Bussini, S., Cardin, V., Corbo, M., Conti, G., Galimberti, D., . . . Silani, V. (2005). Production of monocyte chemoattractant protein-1 in amyotrophic lateral sclerosis. Muscle Nerve, 32(4), 541-544. doi:10.1002/mus.20376.
Barroeta-Espar, I., Weinstock, L. D., Perez-Nievas, B. G., Meltzer, A. C., Siao Tick Chong, M., Amaral, A. C., . . . Gomez-Isla, T. (2019). Distinct cytokine profiles in human brains resilient to Alzheimer's pathology. Neurobiol Dis, 121, 327-337. doi:10.1016/j.nbd.2018.10.009.
Bartosik-Psujek, H., Belniak, E., Mitosek-Szewczyk, K., Dobosz, B., & Stelmasiak, Z. (2004). Interleukin-8 and RANTES levels in patients with relapsing-remitting multiple sclerosis (RR-MS) treated with cladribine. Acta Neurol Scand, 109(6), 390-392. doi:10.1111/j.1600-0404.2004.00259.x.
Benveniste, E. N., Tang, L. P., & Law, R. M. (1995). Differential regulation of astrocyte TNF-alpha expression by the cytokines TGF-beta, IL-6 and IL-10. International Journal of Developmental Neuroscience, 13(3-4), 341-349.
Biber, K., Dijkstra, I., Trebst, C., De Groot, C. J., Ransohoff, R. M., & Boddeke, H. W. (2002). Functional expression of CXCR3 in cultured mouse and human astrocytes and microglia. Neuroscience, 112(3), 487-497.
Boissonneault, V., Filali, M., Lessard, M., Relton, J., Wong, G., & Rivest, S. (2009). Powerful beneficial effects of macrophage colony-stimulating factor on beta-amyloid deposition and cognitive impairment in Alzheimer's disease. Brain, 132(Pt 4), 1078-1092. doi:10.1093/brain/awn331.
Brombacher, T. M., Nono, J. K., De Gouveia, K. S., Makena, N., Darby, M., Womersley, J., . . . Brombacher, F. (2017). IL-13-Mediated Regulation of Learning and Memory. J Immunol, 198(7), 2681-2688. doi:10.4049/jimmunol.1601546.
Canoui-Poitrine, F., Luc, G., Mallat, Z., Machez, E., Bingham, A., Ferrieres, J., . . . Group, P. S. (2011). Systemic chemokine levels, coronary heart disease, and ischemic stroke events: the PRIME study. Neurology, 77(12), 1165-1173. doi:10.1212/WNL.0b013e31822dc7c8.

Cash, E., Minty, A., Ferrara, P., Caput, D., Fradelizi, D., & Rott, O. (1994). Macrophage-inactivating IL-13 suppresses experimental autoimmune encephalomyelitis in rats. J Immunol, 153(9), 4258-4267.
Chang, K. A., Kim, S. H., Sakaki, Y., Kim, H. S., Park, C. W., & Suh, Y. H. (1999). Inhibition of the NGF and IL-1beta-induced expression of Alzheimer's amyloid precursor protein by antisense oligonucleotides. Journal of Molecular Neuroscience, 12(1), 69-74.
Chavany, C., Vicario-Abejon, C., Miller, G., & Jendoubi, M. (1998). Transgenic mice for interleukin 3 develop motor neuron degeneration associated with autoimmune reaction against spinal cord motor neurons. Proc Natl Acad Sci U S A, 95(19), 11354-11359.
Chiang, C. S., Powell, H. C., Gold, L. H., Samimi, A., & Campbell, I. L. (1996). Macrophage/microglial-mediated primary demyelination and motor disease induced by the central nervous system production of interleukin-3 in transgenic mice. J Clin Invest, 97(6), 1512-1524. doi:10.1172/JCI118574.
Cho, H., Hashimoto, T., Wong, E., Hori, Y., Wood, L. B., Zhao, L., . . . Irimia, D. (2013). Microfluidic Chemotaxis Platform for Differentiating the Roles of Soluble and Bound Amyloid-beta on Microglial Accumulation. Scientific reports, 3, 1823. doi:10.1038/srep01823.
Chung, I. Y., & Benveniste, E. N. (1990). Tumor necrosis factor-alpha production by astrocytes. Induction by lipopolysaccharide, IFN-gamma, and IL-1 beta. Journal of Immunology, 144(8), 2999-3007.
Combarros, O., Sanchez-Guerra, M., Infante, J., Llorca, J., & Berciano, J. (2002). Gene dose-dependent association of interleukin-1A [-889] allele 2 polymorphism with Alzheimer's disease. J Neurol, 249(9), 1242-1245. doi:10.1007/s00415-002-0819-9.
Davis, S. M., Collier, L. A., Leonardo, C. C., Seifert, H. A., Ajmo, C. T., Jr., & Pennypacker, K. R. (2017). Leukemia Inhibitory Factor Protects Neurons from Ischemic Damage via Upregulation of Superoxide Dismutase 3. Mol Neurobiol, 54(1), 608-622. doi:10.1007/s12035-015-9587-2.
Del Bo, R., Angeretti, N., Lucca, E., De Simoni, M. G., & Forloni, G. (1995). Reciprocal control of inflammatory cytokines, IL-1 and IL-6, and beta-amyloid production in cultures. Neuroscience Letters, 188(1), 70-74.
Derecki, N. C., Cardani, A. N., Yang, C. H., Quinnies, K. M., Crihfield, A., Lynch, K. R., & Kipnis, J. (2010). Regulation of learning and memory by meningeal immunity: a key role for IL-4. J Exp Med, 207(5), 1067-1080. doi:10.1084/jem.20091419.
Ding, X., Cao, F., Cui, L., Ciric, B., Zhang, G. X., & Rostami, A. (2015). IL-9 signaling affects central nervous system resident cells during inflammatory stimuli. Exp Mol Pathol, 99(3), 570-574. doi:10.1016/j.yexmp.2015.07.010.
Dorf, M. E., Berman, M. A., Tanabe, S., Heesen, M., & Luo, Y. (2000). Astrocytes express functional chemokine receptors. Journal of Neuroimmunology, 111(1-2), 109-121.
Du Yan, S., Zhu, H., Fu, J., Yan, S. F., Roher, A., Tourtellotte, W. W., . . . Schmidt, A. M. (1997). Amyloid-beta peptide-receptor for advanced glycation endproduct interaction elicits neuronal expression of macrophage-colony stimulating factor: a proinflammatory pathway in Alzheimer disease. Proc Natl Acad Sci U S A, 94(10), 5296-5301.
Ellis, S. L., Gysbers, V., Manders, P. M., Li, W., Hofer, M. J., Muller, M., & Campbell, I. L. (2010). The cell-specific induction of CXC chemokine ligand 9 mediated by IFN-gamma in microglia of the central nervous system is determined by the myeloid transcription factor PU.1. Journal of Immunology, 185(3), 1864-1877. doi:10.4049/jimmunol.1000900.
Fiala, M., Avagyan, H., Merino, J. J., Bernas, M., Valdivia, J., Espinosa-Jeffrey, A., . . . Weinand, M. (2013). Chemotactic and mitogenic stimuli of neuronal apoptosis in patients with medically intractable temporal lobe epilepsy. Pathophysiology, 20(1), 59-69. doi: 10.1016/j.pathophys.2012.02.003.
Fontaine, R. H., Cases, O., Lelievre, V., Mesples, B., Renauld, J. C., Loron, G., . . . Gressens, P. (2008). IL-9/IL-9 receptor signaling selectively protects cortical neurons against developmental apoptosis. Cell Death and Differentiation, 15(10), 1542-1552. doi:10.1038/cdd.2008.79.

(56) References Cited

OTHER PUBLICATIONS

Frydecka, D., Krzystek-Korpacka, M., Lubeiro, A., Stramecki, F., Stanczykiewicz, B., Beszlej, J. A., . . . Misiak, B. (2018). Profiling inflammatory signatures of schizophrenia: A cross-sectional and meta-analysis study. Brain Behav Immun, 71, 28-36. doi:10.1016/j.bbi.2018.05.002.

Fulzele, S., & Pillai, A. (2009). Decreased VEGF mRNA expression in the dorsolateral prefrontal cortex of schizophrenia subjects. Schizophr Res, 115(2-3), 372-373. doi:10.1016/j.schres.2009.06.005.

Gade-Andavolu, R., Comings, D. E., MacMurray, J., Vuthoori, R. K., Tourtellotte, W. W., Nagra, R. M., & Cone, L. A. (2004). RANTES: a genetic risk marker for multiple sclerosis. Mult Scler, 10(5), 536-539. doi:10.1191/1352458504ms1080oa.

Gadient, R. A., & Otten, U. H. (1997). Interleukin-6 (IL-6)—a molecule with both beneficial and destructive potentials. Progress in Neurobiology, 52(5), 379-390.

Gahring, L. C., White, H. S., Skradski, S. L., Carlson, N. G., & Rogers, S. W. (1997). Interleukin-1alpha in the brain is induced by audiogenic seizure. Neurobiol Dis, 3(4), 263-269. doi:10.1006/nbdi.1996.0123.

Gallo, P., Pagni, S., Giometto, B., Piccinno, M. G., Bozza, F., Argentiero, V., & Tavolato, B. (1990). Macrophage-colony stimulating factor (M-CSF) in the cerebrospinal fluid. J Neuroimmunol, 29(1-3), 105-112.

Greenberg, D. A., & Jin, K. (2006). Growth factors and stroke. NeuroRx, 3(4), 458-465. doi:10.1016/j.nurx.2006.08.003.

Hanisch, U. K., Lyons, S. A., Prinz, M., Nolte, C., Weber, J. R., Kettenmann, H., & Kirchhoff, F. (1997). Mouse brain microglia express interleukin-15 and its multimeric receptor complex functionally coupled to Janus kinase activity. J Biol Chem, 272(46), 28853-28860.

He, Y., Hsuchou, H., Wu, X., Kastin, A. J., Khan, R. S., Pistell, P. J., . . . Pan, W. (2010). Interleukin-15 receptor is essential to facilitate GABA transmission and hippocampal-dependent memory. Journal of Neuroscience, 30(13), 4725-4734. doi:10.1523/JNEUROSCI.6160-09.2010.

Heyen, J. R., Ye, S., Finck, B. N., & Johnson, R. W. (2000). Interleukin (IL)-10 inhibits IL-6 production in microglia by preventing activation of NF-kappaB. Molecular Brain Research, 77(1), 138-147.

Hinojosa, A. E., Garcia-Bueno, B., Leza, J. C., & Madrigal, J. L. (2011). CCL2/MCP-1 modulation of microglial activation and proliferation. J Neuroinflammation, 8, 77. doi:10.1186/1742-2094-8-77.

Hotta, K., Emala, C. W., & Hirshman, C. A. (1999). TNF-alpha upregulates Gialpha and Gqalpha protein expression and function in human airway smooth muscle cells. American Journal of Physiology, 276(3 Pt 1), L405-411.

Huang, Y. S., Cheng, S. N., Chuch, S. H., Tsai, Y. L., Liou, N. H., Guo, Y. W., . . . Ma, K. H. (2009). Effects of interleukin-15 on neuronal differentiation of neural stem cells. Brain Research, 1304, 38-48. doi:10.1016/j.brainres.2009.09.009.

Imai, Y., & Kohsaka, S. (2002). Intracellular signaling in M-CSF-induced microglia activation: role of Iba1. Glia, 40(2), 164-174. doi:10.1002/glia.10149.

Ireland, D. D., & Reiss, C. S. (2004). Expression of IL-12 receptor by neurons. Viral Immunology, 17(3), 411-422. doi:10.1089/0882824041856987.

Jana, M., Dasgupta, S., Pal, U., & Pahan, K. (2009). IL-12 p40 homodimer, the so-called biologically inactive molecule, induces nitric oxide synthase in microglia via IL-12R beta 1. Glia, 57(14), 1553-1565. doi:10.1002/glia.20869.

Jana, M., & Pahan, K. (2009). IL-12 p40 homodimer, but not IL-12 p70, induces the expression of IL-16 in microglia and macrophages. Molecular Immunology, 46(5), 773-783. doi:10.1016/j.molimm.2008.10.033.

Janelsins, M. C., Mastrangelo, M. A., Park, K. M., Sudol, K. L., Narrow, W. C., Oddo, S., . . . Bowers, W. J. (2008). Chronic neuron-specific tumor necrosis factor-alpha expression enhances the local inflammatory environment ultimately leading to neuronal death in 3xTg-AD mice. American Journal of Pathology, 173(6), 1768-1782. doi:10.2353/ajpath.2008.080528.

Jiang, C. L., & Lu, C. L. (1998). Interleukin-2 and its effects in the central nervous system. Biological Signals and Receptors, 7(3), 148-156.

Jin, K., Zhu, Y., Sun, Y., Mao, X. O., Xie, L., & Greenberg, D. A. (2002). Vascular endothelial growth factor (VEGF) stimulates neurogenesis in vitro and in vivo. Proceedings of the National Academy of Sciences of the United States of America, 99(18), 11946-11950. doi:10.1073/pnas.182296499.

Johnson, E. A., Dao, T. L., Guignet, M. A., Geddes, C. E., Koemeter-Cox, A. I., & Kan, R. K. (2011a). Increased expression of the chemokines CXCL1 and MIP-1alpha by resident brain cells precedes neutrophil infiltration in the brain following prolonged soman-induced status epilepticus in rats. Journal of neuroinflammation, 8, 41. doi:10.1186/1742-2094-8-41.

Johnstone, M., Gearing, A. J., & Miller, K. M. (1999). A central role for astrocytes in the inflammatory response to beta-amyloid; chemokines, cytokines and reactive oxygen species are produced. Journal of Neuroimmunology, 93(1-2), 182-193.

Jones, N. C., Prior, M. J., Burden-Teh, E., Marsden, C. A., Morris, P. G., & Murphy, S. (2005). Antagonism of the interleukin-1 receptor following traumatic brain injury in the mouse reduces the No. of nitric oxide synthase-2-positive cells and improves anatomical and functional outcomes. Eur J Neurosci, 22(1), 72-78. doi:10.1111/j.1460-9568.2005.04221.x.

Kawahara, K., Suenobu, M., Yoshida, A., Koga, K., Hyodo, A., Ohtsuka, H., . . . Nakayama, H. (2012). Intracerebral microinjection of interleukin-4/interleukin-13 reduces beta-amyloid accumulation in the ipsilateral side and improves cognitive deficits in young amyloid precursor protein 23 mice. Neuroscience, 207, 243-260. doi:10.1016/j.neuroscience.2012.01.049.

Kiyota, T., Okuyama, S., Swan, R. J., Jacobsen, M. T., Gendelman, H. E., & Ikezu, T. (2010). CNS expression of anti-inflammatory cytokine interleukin-4 attenuates Alzheimer's disease-like pathogenesis in APP+PS1 bigenic mice. FASEB Journal, 24(8), 3093-3102. doi:10.1096/fj.10-155317.

Konoeda, F., Shichita, T., Yoshida, H., Sugiyama, Y., Muto, G., Hasegawa, E., . . . Yoshimura, A. (2010). Therapeutic effect of IL-12/23 and their signaling pathway blockade on brain ischemia model. Biochem Biophys Res Commun, 402(3), 500-506. doi:10.1016/j.bbrc.2010.10.058.

Lampron, A., Pimentel-Coelho, P. M., & Rivest, S. (2013). Migration of bone marrow-derived cells into the central nervous system in models of neurodegeneration. J Comp Neurol, 521(17), 3863-3876. doi:10.1002/cne.23363.

Laske, C., Stellos, K., Stransky, E., Leyhe, T., & Gawaz, M. (2009). Decreased plasma levels of granulocyte-colony stimulating factor (G-CSF) in patients with early Alzheimer's disease. J Alzheimers Dis, 17(1), 115-123. doi:10.3233/JAD-2009-1017.

Lee, Y. B., Satoh, J., Walker, D. G., & Kim, S. U. (1996). Interleukin-15 gene expression in human astrocytes and microglia in culture. Neuroreport, 7(5), 1062-1066.

Li, T., Zhai, X., Jiang, J., Song, X., Han, W., Ma, J., . . . Jiang, L. (2017). Intraperitoneal injection of IL-4/IFN-gamma modulates the proportions of microglial phenotypes and improves epilepsy outcomes in a pilocarpine model of acquired epilepsy. Brain Res, 1657, 120-129. doi:10.1016/j.brainres.2016.12.006.

Lin, H., Hikawa, N., Takenaka, T., & Ishikawa, Y. (2000). Interleukin-12 promotes neurite outgrowth in mouse sympathetic superior cervical ganglion neurons. Neuroscience Letters, 278(3), 129-132.

Lin, Y., Zhang, L., Dai, Y., Li, H., Wang, Y., Zhang, B., . . . Lu, Z. (2015). Expression of interleukin-9 and its upstream stimulating factors in rats with ischemic stroke. Neurol Sci, 36(6), 913-920. doi:10.1007/s10072-015-2096-2.

Liva, S. M., & de Vellis, J. (2001). IL-5 induces proliferation and activation of microglia via an unknown receptor. Neurochemical Research, 26(6), 629-637.

Luo, X. J., Li, M., Huang, L., Nho, K., Deng, M., Chen, Q., . . . Su, B. (2012). The interleukin 3 gene (IL3) contributes to human brain

(56) References Cited

OTHER PUBLICATIONS volume variation by regulating proliferation and survival of neural progenitors. PLoS One, 7(11), e50375. doi:10.1371/journal.pone. 0050375.
Luo, Y., Fischer, F. R., Hancock, W. W., & Dorf, M. E. (2000). Macrophage inflammatory protein-2 and KC induce chemokine production by mouse astrocytes. J Immunol, 165(7), 4015-4023.
Madrigal, J. L., Leza, J. C., Polak, P., Kalinin, S., & Feinstein, D. L. (2009). Astrocyte-derived MCP-1 mediates neuroprotective effects of noradrenaline. J Neurosci, 29(1), 263-267. doi:10.1523/JNEUROSCI. 4926-08.2009.
Mangano, E. N., Peters, S., Litteljohn, D., So, R., Bethune, C., Bobyn, J., . . . Hayley, S. (2011). Granulocyte macrophage-colony stimulating factor protects against substantia nigra dopaminergic cell loss in an environmental toxin model of Parkinson's disease. Neurobiol Dis, 43(1), 99-112. doi:10.1016/j.nbd.2011.02.011.
McAlpine, F. E., Lee, J. K., Harms, A. S., Ruhn, K. A., Blurton-Jones, M., Hong, J., . . . Tansey, M. G. (2009). Inhibition of soluble TNF signaling in a mouse model of Alzheimer's disease prevents pre-plaque amyloid-associated neuropathology. Neurobiol Dis, 34(1), 163-177.
Meda, L., Cassatella, M. A., Szendrei, G. I., Otvos, L., Jr., Baron, P., Villalba, M., . . . Rossi, F. (1995). Activation of microglial cells by beta-amyloid protein and interferon-gamma. Nature, 374(6523), 647-650. doi:10.1038/374647a0.
Mehler, M. F., Rozental, R., Dougherty, M., Spray, D. C., & Kessler, J. A. (1993). Cytokine regulation of neuronal differentiation of hippocampal progenitor cells. Nature, 362(6415), 62-65. doi:10. 1038/362062a0.
Mehta, H. M., Malandra, M., & Corey, S. J. (2015). G-CSF and GM-CSF in Neutropenia. J Immunol, 195(4), 1341-1349. doi: 10.4049/jimmunol.1500861.
Mitrasinovic, O. M., Perez, G. V., Zhao, F., Lee, Y. L., Poon, C., & Murphy, G. M., Jr. (2001). Overexpression of macrophage colony-stimulating factor receptor on microglial cells induces an inflammatory response. J Biol Chem, 276(32), 30142-30149. doi:10.1074/ jbc.M104265200.
Moors, M., Vudattu, N. K., Abel, J., Kramer, U., Rane, L., Ulfig, N., . . . Maeurer, M. J. (2010). Interleukin-7 (IL-7) and IL-7 splice variants affect differentiation of human neural progenitor cells. Genes Immun, 11(1), 11-20. doi:10.1038/gene.2009.77.
Mrak, R. E., & Griffin, W. S. (2001). Interleukin-1, neuroinflammation, and Alzheimer's disease. Neurobiology of Aging, 22(6), 903-908.
Muneer, A. (2016). Bipolar Disorder: Role of Inflammation and the Development of Disease Biomarkers. Psychiatry Investig, 13(1), 18-33. doi:10.4306/pi.2016.13.1.18.
Murphy, G. M., Jr., Yang, L., & Cordell, B. (1998). Macrophage colony-stimulating factor augments beta-amyloid-induced interleukin-1, interleukin-6, and nitric oxide production by microglial cells. J Biol Chem, 273(33), 20967-20971.
Murphy, G. M., Jr., Zhao, F., Yang, L., & Cordell, B. (2000). Expression of macrophage colony-stimulating factor receptor is increased in the AbetaPP(V717F) transgenic mouse model of Alzheimer's disease. Am J Pathol, 157(3), 895-904.
Nakanishi, M., Niidome, T., Matsuda, S., Akaike, A., Kihara, T., & Sugimoto, H. (2007). Microglia-derived interleukin-6 and leukaemia inhibitory factor promote astrocytic differentiation of neural stem/ progenitor cells. European Journal of Neuroscience, 25(3), 649-658. doi:10.1111/j.1460-9568.2007.05309.x.
Natarajan, C., Sriram, S., Muthian, G., & Bright, J. J. (2004). Signaling through JAK2-STAT5 pathway is essential for IL-3-induced activation of microglia. Glia, 45(2), 188-196. doi:10.1002/ glia.10316.
Nunnari, G., Xu, Y., Acheampong, E. A., Fang, J., Daniel, R., Zhang, C., . . . Pomerantz, R. J. (2005). Exogenous IL-7 induces Fas-mediated human neuronal apoptosis: potential effects during human immunodeficiency virus type 1 infection. Journal of Neurovirology, 11(4), 319-328. doi:10.1080/13550280500187005.

Park, K. W., Baik, H. H., & Jin, B. K. (2009). IL-13-induced oxidative stress via microglial NADPH oxidase contributes to death of hippocampal neurons in vivo. J Immunol, 183(7), 4666-4674. doi:10.4049/jimmunol.0803392.
Passos, G. F., Figueiredo, C. P., Prediger, R. D., Silva, K. A., Siqueira, J. M., Duarte, F. S., . . . Calixto, J. B. (2010). Involvement of phosphoinositide 3-kinase gamma in the neuro-inflammatory response and cognitive impairments induced by beta-amyloid 1-40 peptide in mice. Brain Behav Immun, 24(3), 493-501. doi:10.1016/ j.bbi.2009.12.003.
Peterson, P. K., Hu, S., Salak-Johnson, J., Molitor, T. W., & Chao, C. C. (1997). Differential production of and migratory response to beta chemokines by human microglia and astrocytes. Journal of Infectious Diseases, 175(2), 478-481.
Renner, N. A., Ivey, N. S., Redmann, R. K., Lackner, A. A., & MacLean, A. G. (2011). MCP-3/CCL7 production by astrocytes: implications for SIV neuroinvasion and AIDS encephalitis. Journal of Neurovirology, 17(2), 146-152. doi:10.1007/s13365-010-0017-y.
Rivera, S., Gold, S. J., & Gall, C. M. (1994). Interleukin-1 beta increases basic fibroblast growth factor mRNA expression in adult rat brain and organotypic hippocampal cultures. Brain Research. Molecular Brain Research, 27(1), 12-26.
Rossi, S., Mancino, R., Bergami, A., Mori, F., Castelli, M., De Chiara, V., . . . Centonze, D. (2011). Potential role of IL-13 in neuroprotection and cortical excitability regulation in multiple sclerosis. Mult Scler, 17(11), 1301-1312. doi:10.1177/ 1352458511410342.
Ryu, J. K., Cho, T., Choi, H. B., Wang, Y. T., & McLarnon, J. G. (2009). Microglial VEGF receptor response is an integral chemotactic component in Alzheimer's disease pathology. Journal of Neuroscience, 29(1), 3-13. doi:10.1523/JNEUROSCI.2888-08.2009.
Sanchez, A., Wadhwani, S., & Grammas, P. (2010). Multiple neurotrophic effects of VEGF on cultured neurons. Neuropeptides, 44(4), 323-331. doi:10.1016/j.npep.2010.04.002.
Schabitz, W. R., Kollmar, R., Schwaninger, M., Juettler, E., Bardutzky, J., Scholzke, M. N., . . . Schwab, S. (2003). Neuroprotective effect of granulocyte colony-stimulating factor after focal cerebral ischemia. Stroke, 34(3), 745-751. doi:10.1161/01.STR.0000057814. 70180.17.
Schabitz, W. R., Kruger, C., Pitzer, C., Weber, D., Laage, R., Gassler, N., . . . Schneider, A. (2008). A neuroprotective function for the hematopoietic protein granulocyte-macrophage colony stimulating factor (GM-CSF). Journal of Cerebral Blood Flow and Metabolism, 28(1), 29-43. doi:10.1038/sj.jcbfm.9600496.
Schneider, A., Kruger, C., Steigleder, T., Weber, D., Pitzer, C., Laage, R., . . . Schabitz, W. R. (2005). The hematopoietic factor G-CSF is a neuronal ligand that counteracts programmed cell death and drives neurogenesis. Journal of Clinical Investigation, 115(8), 2083-2098. doi:10.1172/JCI23559.
Schneider, A., Kuhn, H.-G., & Schäbitz, W.-R. (2005). Review a role for G-CSF (granulocyte-Colony stimulating factor) in the central nervous system. Cell cycle, 4(12), 1753-1757.
Schwieler, L., Larsson, M. K., Skogh, E., Kegel, M. E., Orhan, F., Abdelmoaty, S., . . . Engberg, G. (2015). Increased levels of IL-6 in the cerebrospinal fluid of patients with chronic schizophrenia—significance for activation of the kynurenine pathway. J Psychiatry Neurosci, 40(2), 126-133.
Sgadari, C., Farber, J. M., Angiolillo, A. L., Liao, F., Teruya-Feldstein, J., Burd, P. R., . . . Tosato, G. (1997). Mig, the monokine induced by interferon-gamma, promotes tumor necrosis in vivo. Blood, 89(8), 2635-2643.
Shaafi, S., Sharifipour, E., Rahmanifar, R., Hejazi, S., Andalib, S., Nikanfar, M., . . . Mehdizadeh, R. (2014). Interleukin-6, a reliable prognostic factor for ischemic stroke. Iran J Neurol, 13(2), 70-76.
Sharma, S., Yang, B., Xi, X., Grotta, J. C., Aronowski, J., & Savitz, S. I. (2011). IL-10 directly protects cortical neurons by activating PI-3 kinase and STAT-3 pathways. Brain Research, 1373, 189-194. doi:10.1016/j.brainres.2010.11.096.
Shelton, R. C., Claiborne, J., Sidoryk-Wegrzynowicz, M., Reddy, R., Aschner, M., Lewis, D. A., & Mirnics, K. (2011). Altered expression of genes involved in inflammation and apoptosis in frontal cortex in major depression. Mol Psychiatry, 16(7), 751-762. doi:10.1038/mp.2010.52.

(56) References Cited

OTHER PUBLICATIONS

Shin, W. H., Lee, D. Y., Park, K. W., Kim, S. U., Yang, M. S., Joe, E. H., & Jin, B. K. (2004). Microglia expressing interleukin-13 undergo cell death and contribute to neuronal survival in vivo. Glia, 46(2), 142-152. doi:10.1002/glia.10357.

Si, Q., Cosenza, M., Zhao, M. L., Goldstein, H., & Lee, S. C. (2002). GM-CSF and M-CSF modulate beta-chemokine and HIV-1 expression in microglia. Glia, 39(2), 174-183. doi:10.1002/glia.10095.

Simi, A., Tsakiri, N., Wang, P., & Rothwell, N. J. (2007). Interleukin-1 and inflammatory neurodegeneration. Biochemical Society Transactions, 35(Pt 5), 1122-1126. doi:10.1042/BST0351122.

Smith, A. M., Gibbons, H. M., Oldfield, R. L., Bergin, P. M., Mee, E. W., Curtis, M. A., . . . Dragunow, M. (2013). M-CSF increases proliferation and phagocytosis while modulating receptor and transcription factor expression in adult human microglia. J Neuroinflammation, 10, 85. doi:10.1186/1742-2094-10-85.

Sorce, S., Bonnefont, J., Julien, S., Marq-Lin, N., Rodriguez, I., Dubois-Dauphin, M., & Krause, K. H. (2010). Increased brain damage after ischaemic stroke in mice lacking the chemokine receptor CCR5. Br J Pharmacol, 160(2), 311-321. doi:10.1111/j.1476-5381.2010.00697.x.

Szczepanik, A. M., Funes, S., Petko, W., & Ringheim, G. E. (2001). IL-4, IL-10 and IL-13 modulate A beta(1-42)-induced cytokine and chemokine production in primary murine microglia and a human monocyte cell line. Journal of Neuroimmunology, 113(1), 49-62.

Taoufik, Y., de Goer de Herve, M. G., Giron-Michel, J., Durali, D., Cazes, E., Tardieu, M., . . . Delfraissy, J. F. (2001). Human microglial cells express a functional IL-12 receptor and produce IL-12 following IL-12 stimulation. European Journal of Immunology, 31(11), 3228-3239. doi: 10.1002/1521-4141(200111)31:11<3228::AID-IMMU3228>3.0.CO;2-7.

Tarkowski, E., Wallin, A., Regland, B., Blennow, K., & Tarkowski, A. (2001). Local and systemic GM-CSF increase in Alzheimer's disease and vascular dementia. Acta Neurol Scand, 103(3), 166-174.

Teixeira, A. L., Gama, C. S., Rocha, N. P., & Teixeira, M. M. (2018). Revisiting the Role of Eotaxin-1/CCL11 in Psychiatric Disorders. Front Psychiatry, 9, 241. doi:10.3389/fpsyt.2018.00241.

Thompson, W. L., & Van Eldik, L. J. (2009). Inflammatory cytokines stimulate the chemokines CCL2/MCP-1 and CCL7/MCP-3 through NFkB and MAPK dependent pathways in rat astrocytes [corrected]. Brain Research, 1287, 47-57. doi:10.1016/j.brainres.2009.06.081.

Tripathy, D., Thirumangalakudi, L., & Grammas, P. (2010). RANTES upregulation in the Alzheimer's disease brain: a possible neuroprotective role. Neurobiology of Aging, 31(1), 8-16. doi:10.1016/j.neurobiolaging.2008.03.009.

Vezzani, A., Balosso, S., & Ravizza, T. (2008). The role of cytokines in the pathophysiology of epilepsy. Brain Behav Immun, 22(6), 797-803. doi:10.1016/j.bbi.2008.03.009.

Villeda, S. A., Luo, J., Mosher, K. I., Zou, B., Britschgi, M., Bieri, G., . . . Wyss-Coray, T. (2011). The ageing systemic milieu negatively regulates neurogenesis and cognitive function. Nature, 477(7362), 90-94. doi:10.1038/nature10357.

Wainwright, D. A., Xin, J., Sanders, V. M., & Jones, K. J. (2008). Differential actions of pituitary adenylyl cyclase-activating polypeptide and interferon gamma on Th2- and Th1-associated chemokine expression in cultured murine microglia. Journal of neurodegeneration & regeneration, 1(1), 31-34.

Warner-Schmidt, J. L., & Duman, R. S. (2007). VEGF is an essential mediator of the neurogenic and behavioral actions of antidepressants. Proceedings of the National Academy of Sciences, 104(11), 4647-4652.

Wiesemann, E., Klatt, J., Wenzel, C., Heidenreich, F., & Windhagen, A. (2003). Correlation of serum IL-13 and IL-5 levels with clinical response to Glatiramer acetate in patients with multiple sclerosis. Clin Exp Immunol, 133(3), 454-460.

Wu, Y. Y., & Bradshaw, R. A. (1996). Synergistic induction of neurite outgrowth by nerve growth factor or epidermal growth factor and interleukin-6 in PC12 cells. Journal of Biological Chemistry, 271(22), 13033-13039.

Xia, M., & Hyman, B. T. (2002). GROalpha/KC, a chemokine receptor CXCR2 ligand, can be a potent trigger for neuronal ERK1/2 and PI-3 kinase pathways and for tau hyperphosphorylation—a role in Alzheimer's disease? Journal of Neuroimmunology, 122(1-2), 55-64.

Xiu, M. H., Lin, C. G., Tian, L., Tan, Y. L., Chen, J., Chen, S., . . . Zhang, X. Y. (2015). Increased IL-3 serum levels in chronic patients with schizophrenia: Associated with psychopathology. Psychiatry Res, 229(1-2), 225-229. doi:10.1016/j.psychres.2015.07.029.

Yamada, M., & Hatanaka, H. (1994). Interleukin-6 protects cultured rat hippocampal neurons against glutamate-induced cell death. Brain Research, 643(1-2), 173-180.

Yang, X., Gao, L., Wu, X., Zhang, Y., & Zang, D. (2016). Increased levels of MIP-1alpha in CSF and serum of ALS. Acta Neurol Scand, 134(2), 94-100. doi:10.1111/ane.12513.

Zakharyan, R., Boyajyan, A., Arakelyan, A., Melkumova, M., Mrazek, F., & Petrek, M. (2012). Monocyte chemoattractant protein-1 in schizophrenia:—2518A/G genetic variant and protein levels in Armenian population. Cytokine, 58(3), 351-354. doi:10.1016/j.cyto.2012.02.013.

Zhang, X. Y., Zhou, D. F., Cao, L. Y., Zhang, P. Y., Wu, G. Y., & Shen, Y. C. (2004). Changes in serum interleukin-2,-6, and -8 levels before and during treatment with risperidone and haloperidol: relationship to outcome in schizophrenia. The Journal of clinical psychiatry, 65(7), 940-947.

Zhao, W., Xie, W., Xiao, Q., Beers, D. R., & Appel, S. H. (2006). Protective effects of an anti-inflammatory cytokine, interleukin-4, on motoneuron toxicity induced by activated microglia. J Neurochem, 99(4), 1176-1187. doi:10.1111/j.1471-4159.2006.04172.x.

Zhou, Y., Sonobe, Y., Akahori, T., Jin, S., Kawanokuchi, J., Noda, M., . . . Suzumura, A. (2011). IL-9 promotes Th17 cell migration into the central nervous system via CC chemokine ligand-20 produced by astrocytes. Journal of Immunology, 186(7), 4415-4421. doi:10.4049/jimmunol.1003307.

Zychowska, M., Rojewska, E., Pilat, D., & Mika, J. (2015). The role of some chemokines from the CXC subfamily in a mouse model of diabetic neuropathy. Journal of diabetes research, 2015.

International Search Report and Written Opinion dated Jul. 29, 2019, from International Application No. PCT/US2019/021701, 15 pages.

Brunoni, AR et al. "Cytokines plasma levels during antidepressant treatment with sertraline and transcranial direct current stimulatin ((DCS): results from a factorial, randomized, controlled trial", Psychopharmacology (Berl). Apr. 2014; 231(7): 1315-1323.

Shin, J-A et al. "Effects of strobe light stimulation on postnatal developing rat retina", Article in Experimental Brain Research, Nov. 2013.

Extended Search Report dated, Jan. 7, 2022, received in corresponding EP Patent Application No. 19765143.3.

Office Action issued in corresponding JP 2020-571346 dated Mar. 7, 2023 with English-language translation.

Office Action issued in corresponding JP 2020-571346 dated Sep. 26, 2023 with English-language translation.

Office Action issued in corresponding KR 10-2020-7028998 dated Oct. 30, 2023 with English-language translation.

* cited by examiner

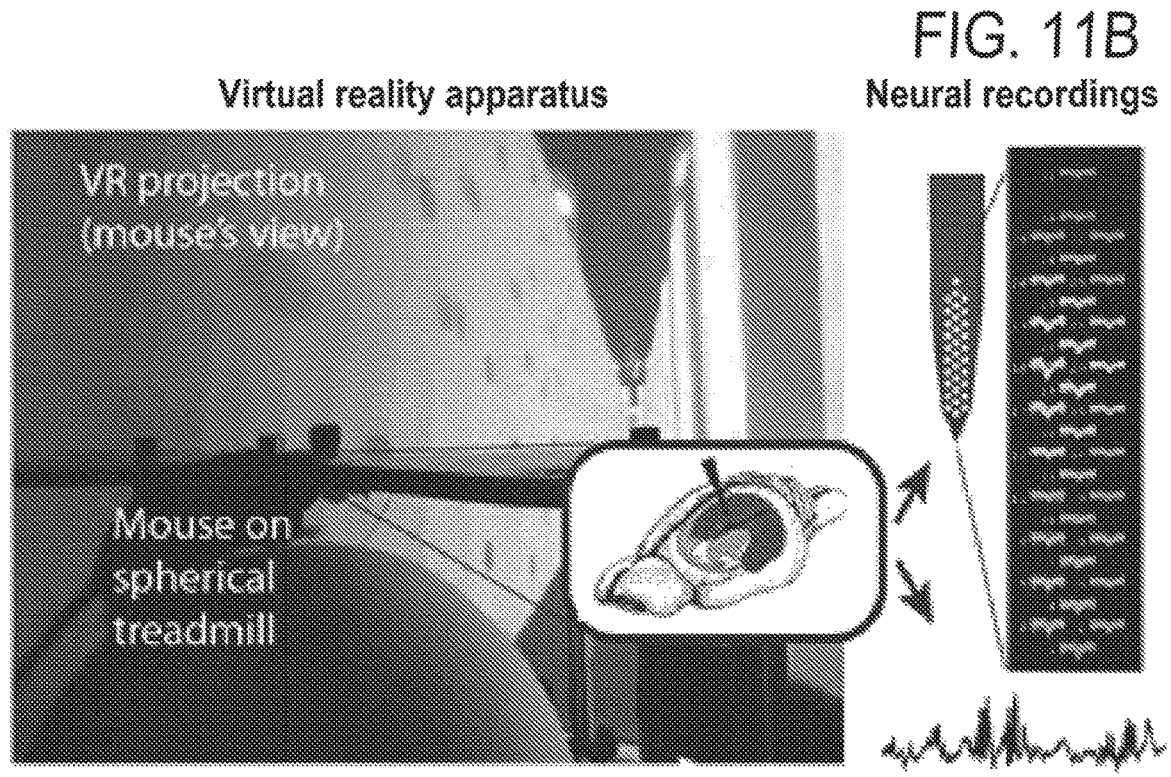
FIG. 11B
FIG. 11A
FIG. 11C
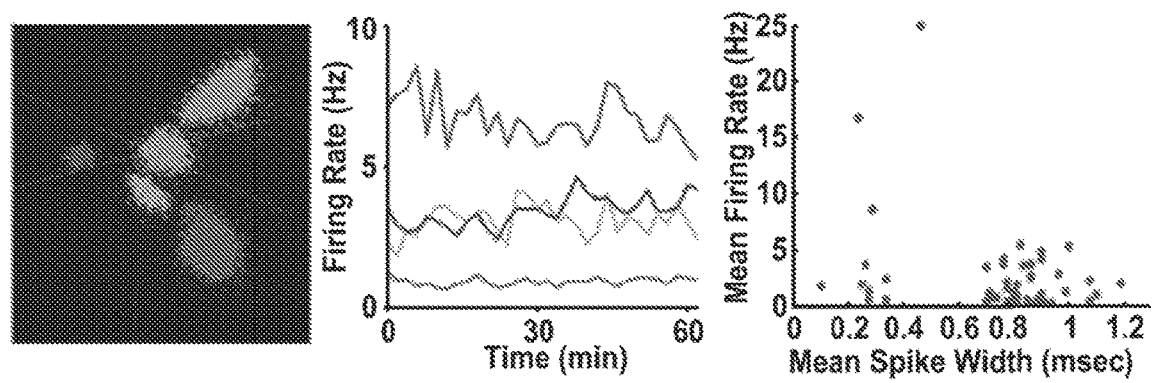
FIG. 12A
FIG. 12B
FIG. 12C

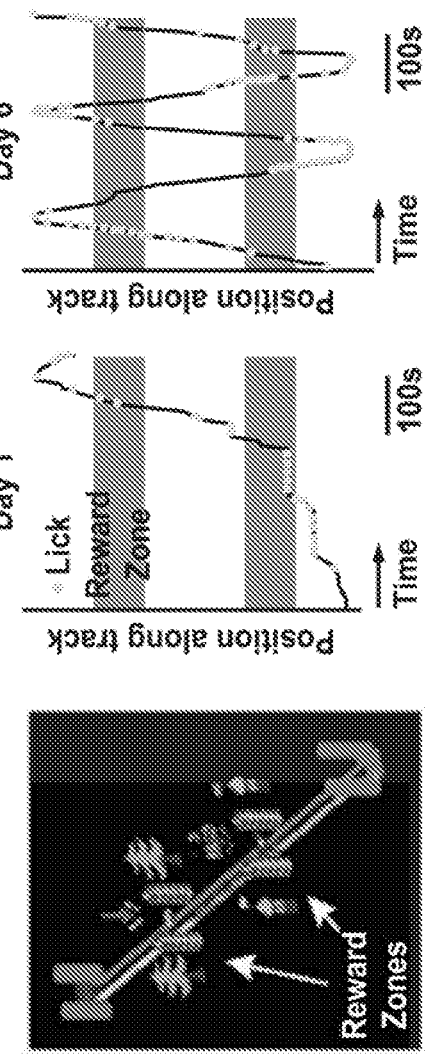
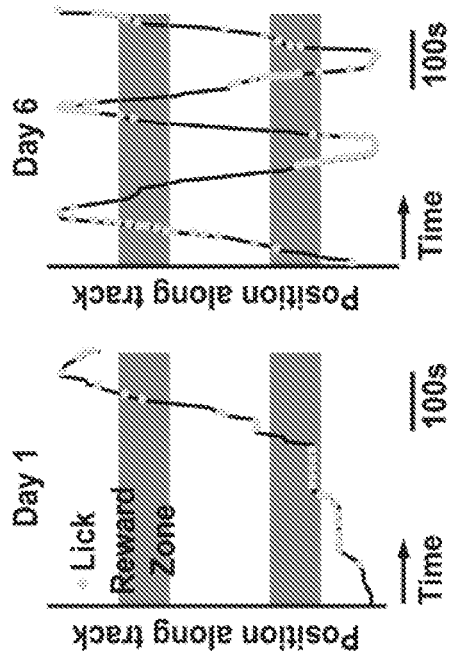
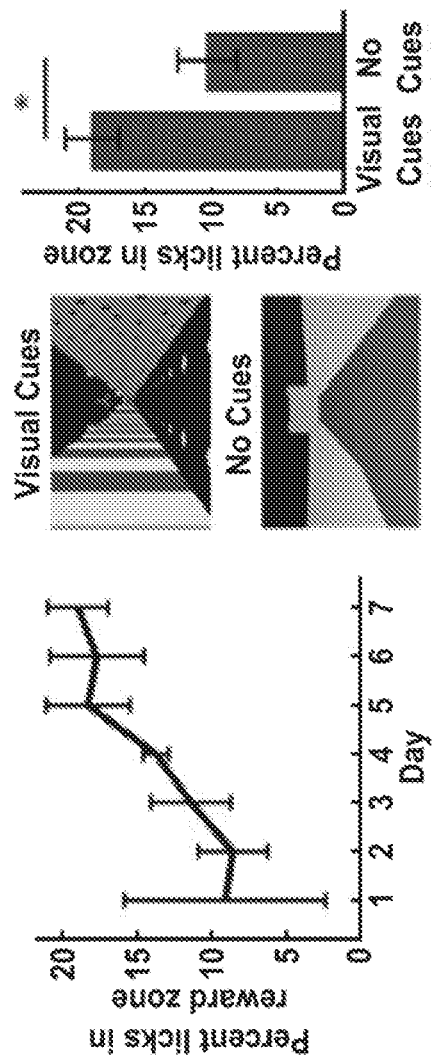
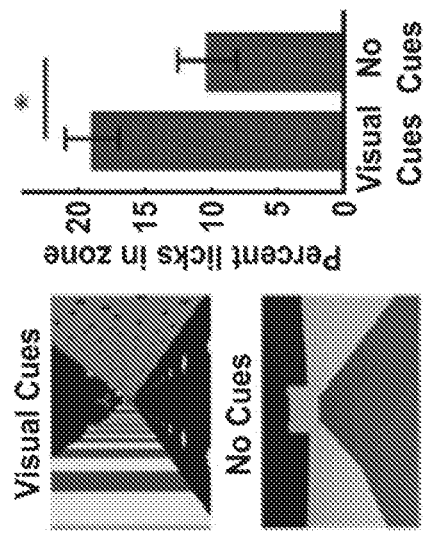
FIG. 15A
FIG. 15B
FIG. 15C
FIG. 15D

Prefontal Cortex

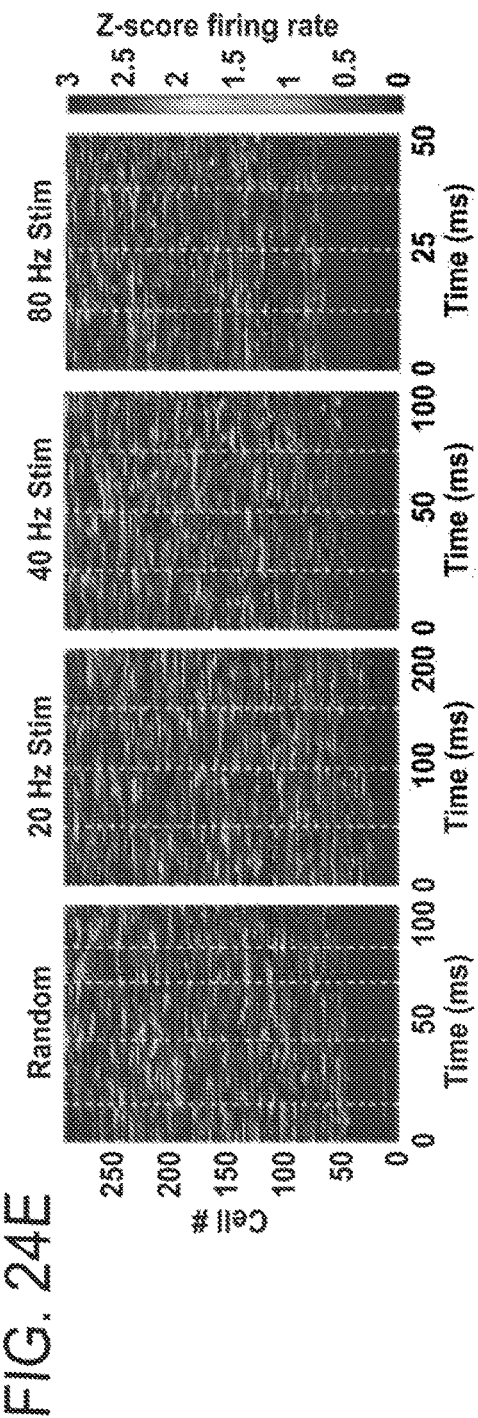
FIG. 24E
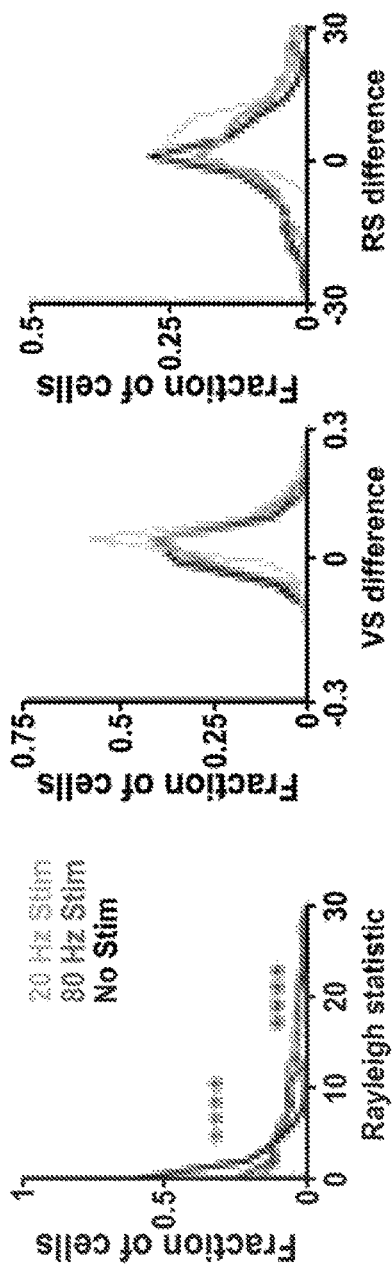
FIG. 24G
FIG. 24F

Hippocampus

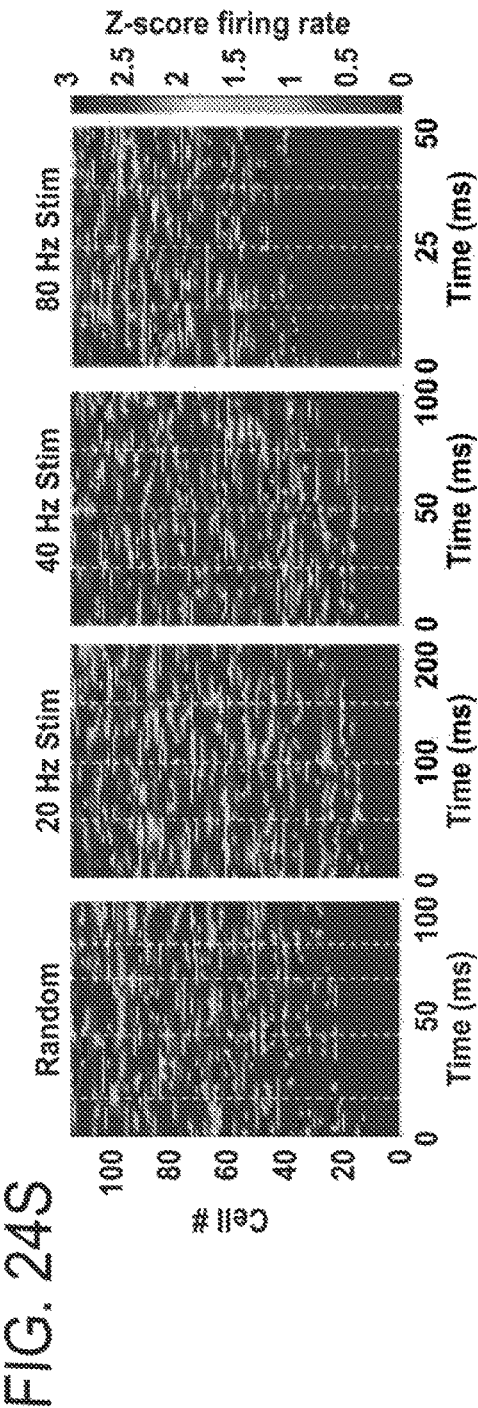
FIG. 24S
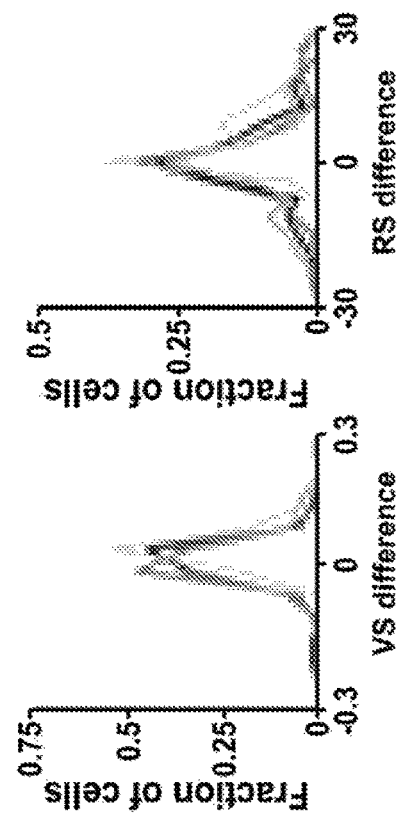
FIG. 24U
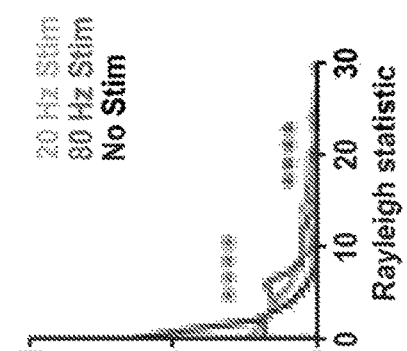
FIG. 24T
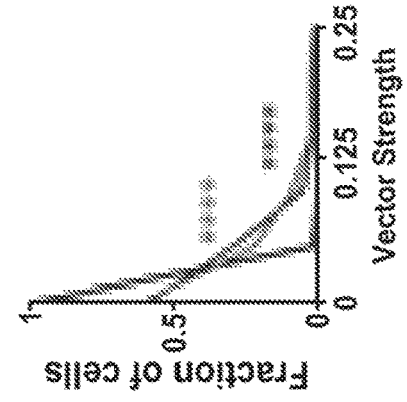

Auditory Cortex

Hippocampus

Prefrontal Cortex

FIG. 26A  Auditory Cortex
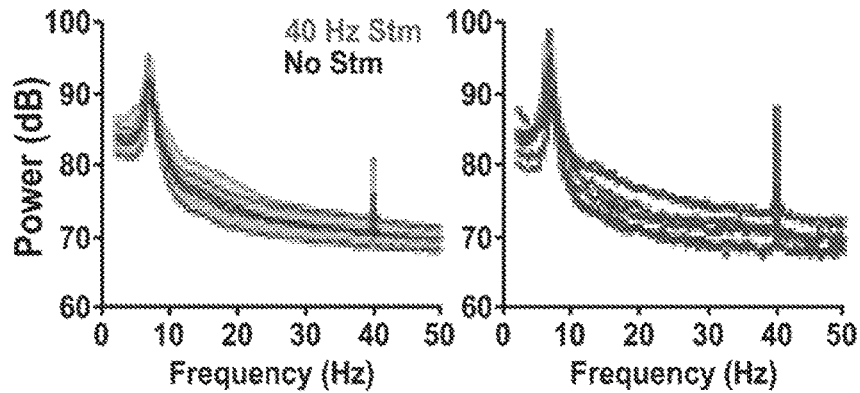
FIG. 26B
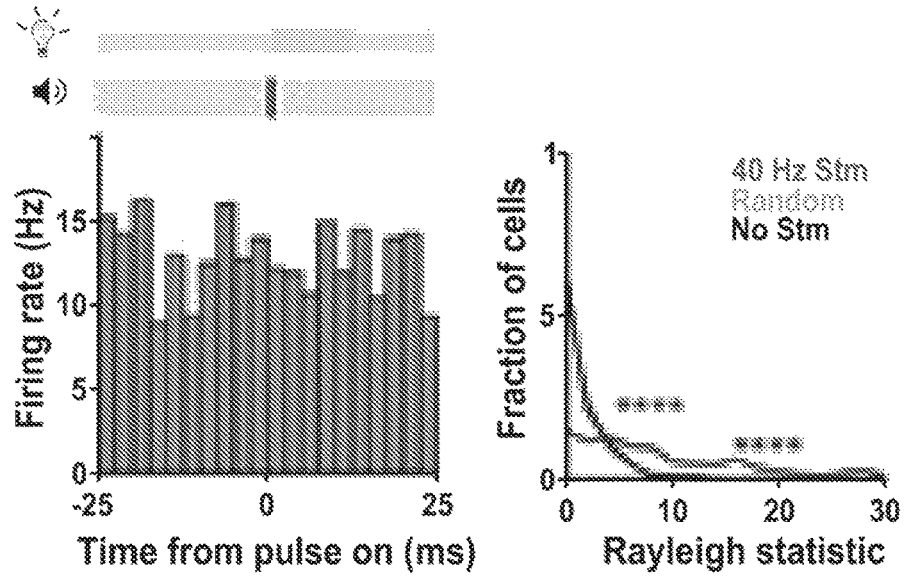
FIG. 26C
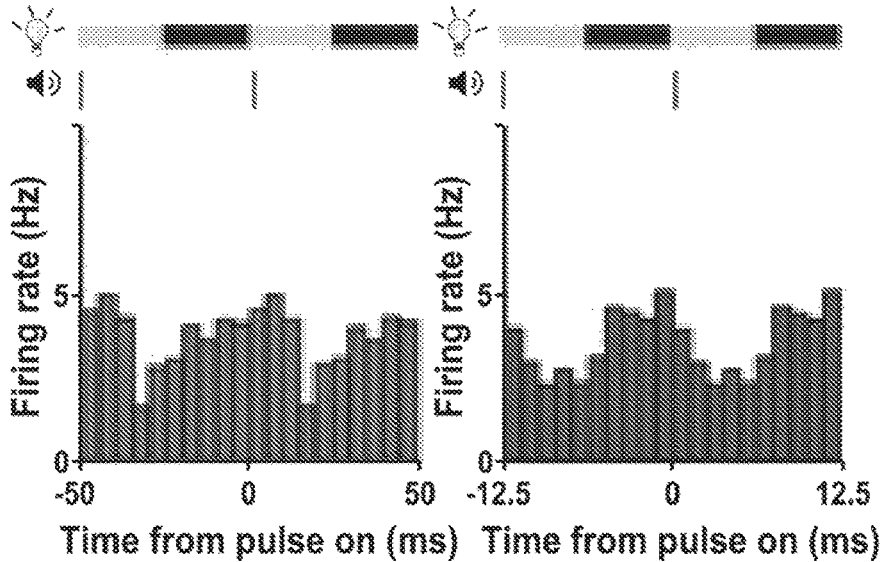

Hippocampus

FIG. 26O Prefrontal Cortex
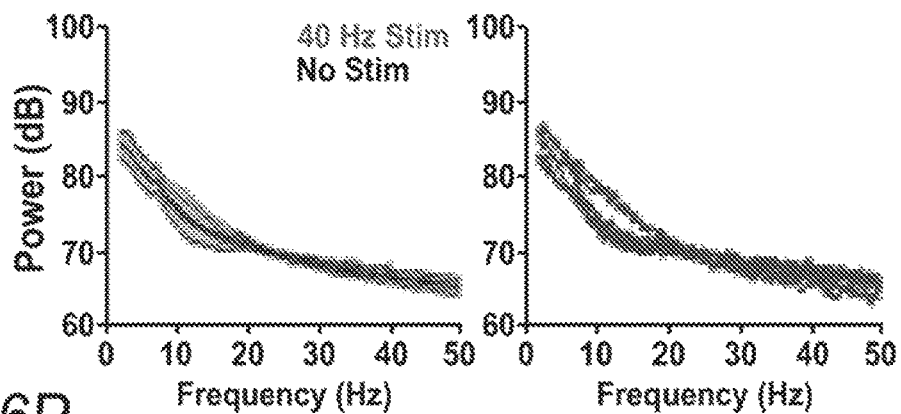
FIG. 26P
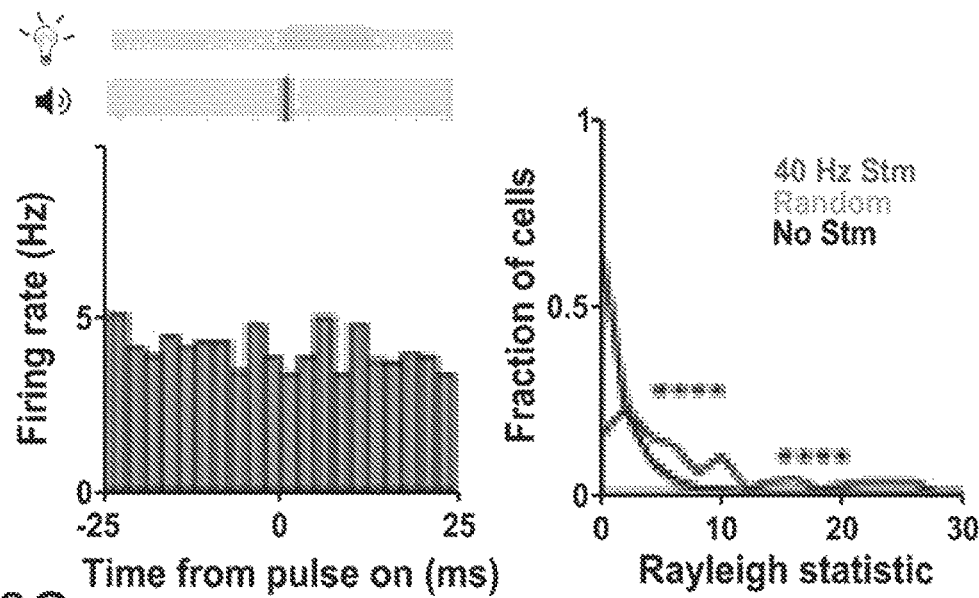
FIG. 26Q
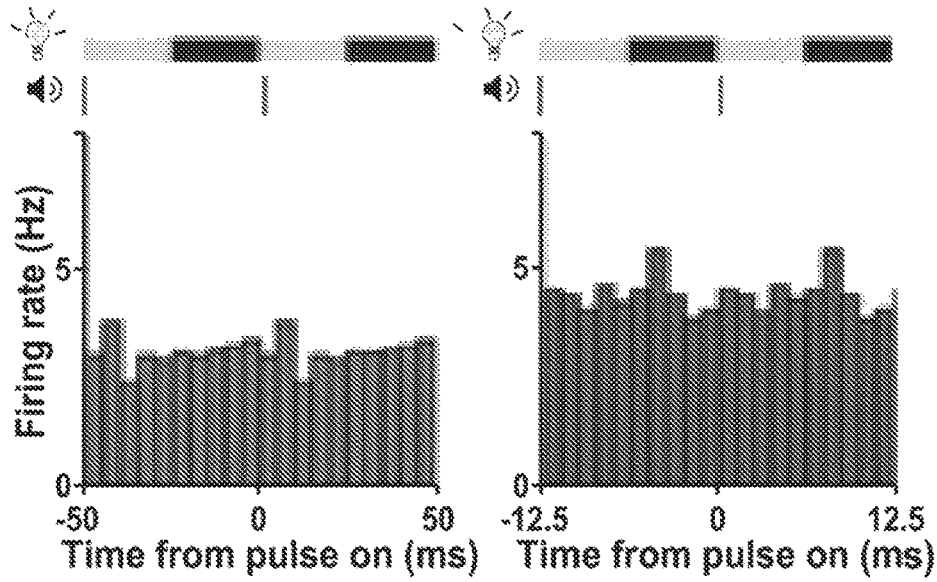

SYSTEMS AND METHODS FOR DRIVING NEURAL ACTIVITY TO CONTROL BRAIN SIGNALING AND GENE EXPRESSION

CROSS-REFERENCE TO RELATED APPLICATIONS

This application is a national stage application filed under 35 U.S.C. § 371 of PCT/US2019/021701 filed Mar. 11, 2019, which claims the benefit of U.S. provisional patent application No. 62/640,736, filed on Mar. 9, 2018, and entitled "SYSTEMS AND METHODS FOR DRIVING NEURAL ACTIVITY TO CONTROL BRAIN IMMUNO-MODULATORY SIGNALING," and U.S. provisional patent application No. 62/648,472, filed on Mar. 27, 2018, and entitled "Sensory Stimulation to Entrain Brain Rhythms in Deep Brain Regions," the disclosures of which are expressly incorporated herein by reference in their entireties.

STATEMENT REGARDING FEDERALLY FUNDED RESEARCH

This invention was made with government support under Grant no. 2T32 NS 007480-18 awarded by the National Institutes of Health. The government has certain rights in the invention.

BACKGROUND

Brain inflammation is thought to play a critical role in multiple diseases including neurodegenerative disease, traumatic brain injury (TBI), normal aging, and development disorders like Schizophrenia and autism, among others. Identification of new methods to precisely, and non-invasively, modulate brain inflammation and gene and protein expression would radically transform the ability to treat diseases, study inflammation and immunomodulatory signaling in brain function, and promote healthy aging.

Gamma activity (e.g., 20-80 Hz neural activity) has long been theorized to facilitate neural communication, synaptic plasticity, coding of information across many neurons (neural codes) by driving cells to fire together on short timescales. Recently, a surprising new role for gamma activity was discovered: driving gamma frequency activity recruits microglial engulfment and clearance of amyloid beta (Aβ) in an Alzheimer's disease (AD) mouse models.[1] Importantly, gamma attenuation was found prior to behavioral deficits, cell death and significant plaque buildup in an Alzheimer's mouse model, suggesting that gamma deficits are an integral component of AD patholgy.[1] Until this time, gamma activity's influence on immune cells was unknown. The discovery that driving gamma activity recruits the brain's immune cells, microglia, therefore revealed a bridge between neural electrical activity and the brain's immune system. This prior work, however, showed no change in immunomodulatory signaling as a result of driving gamma activity. Additionally, this prior work did not show the activity occurring at the intracellular level.

SUMMARY

In one aspect disclosed herein are methods for controlling brain activity in a subject, comprising: delivering a stimulus to the subject, wherein the stimulus induces neural activity in the subject's brain and modulates expression of at least one soluble mediator of cellular activity (such as, for example, a cytokine, chemokine, and/or growth factor) within the subject, and the stimulus is delivered to the subject for less than one hour. In one aspect, the stimulus can be delivered to the subject for less than 30, 10, or 5 minutes.

Also disclosed herein are methods for controlling brain activity of any preceding aspect, wherein the stimulus is a non-invasive stimulus (such as, for example, a 20 Hz sensory flicker stimulus, a 40 Hz sensory flicker stimulus, a random sensory flicker stimulus, a constant sensory stimulus, or any combination thereof). In one aspect, the non-invasive stimulus can be a visual or auditory stimulus.

In one aspect, disclosed herein are methods for controlling brain activity of any preceding aspect, further comprising: selecting a protein to modulate; and selecting one of the 20 Hz sensory flicker stimulus, the 40 Hz sensory flicker stimulus, the random sensory flicker stimulus, or the constant sensory stimulus that modulates the selected protein.

Also disclosed herein are methods for controlling brain activity of any preceding aspect, wherein stimulus comprises a 40 Hz sensory flicker stimulus, and wherein the soluble mediator of cellular activity comprises Interleukin-4 (IL-4), Interleukin-7 (IL-7), Granulocyte-macrophage colony-stimulating factor (GM-CSF), Interleukin-12 p70 (IL-12p70), Interleukin-12 p40 (IL-12p40), Interferon-γ (IFN-γ), LIF, Tumor necrosis factor-α (TNF-α), Macrophage inflammatory protein 1β (MIP-1β) and/or Eotaxin.

Also disclosed herein are methods for controlling brain activity of any preceding aspect, wherein stimulus comprises a random sensory flicker stimulus, and wherein the soluble mediator of cellular activity comprises Interleukin-10 (IL-10).

Also disclosed herein are methods for controlling brain activity of any preceding aspect, wherein stimulus comprises a constant sensory stimulus, and wherein the soluble mediator of cellular activity comprises vascular endothelial growth factor (VEGF), Interleukin-2 (IL-2), Interleukin-5 (IL-5), Interleukin-9 (IL-9), and/or Macrophage inflammatory protein 1α (MIP-1α).

Also disclosed herein are methods for controlling brain activity of any preceding aspect, wherein stimulus comprises a 40 Hz sensory flicker stimulus and a random sensory flicker stimulus, and wherein the soluble mediator of cellular activity comprises monokine induced by gamma interferon (MIG), growth-regulated oncogene-α (GRO-α), LIX (CXCL5), granulocyte colony-stimulating factor (G-CSF), Interleukin-1β (IL-1β) Interleukin-3 (IL-3), Interleukin-6 (IL-6), Interleukin-15 (IL-15), Regulated upon Activation, Normal T cell Expressed, and Secreted (RANTES), and/or macrophage colony-stimulating factor (M-CSF).

Also disclosed herein are methods for controlling brain activity of any preceding aspect, wherein stimulus comprises a 40 Hz sensory flicker stimulus and a constant sensory stimulus, and wherein the soluble mediator of cellular activity comprises Interleukin-13 (IL-13), monocyte chemoattractant protein 1 (MCP-1), and/or Interleukin-1α (IL-1α).

Also disclosed herein are methods for controlling brain activity of any preceding aspect, wherein stimulus comprises a 20 Hz sensory flicker stimulus, and wherein the soluble mediator of cellular activity comprises Interleukin-4 (IL-4), Interleukin-7 (IL-7), Granulocyte-macrophage colony-stimulating factor (GM-CSF), Interleukin-12 p70 (IL-12p70), Interleukin-12 p40 (IL-12p40), Interferon-γ (IFN-γ), LIF, Tumor necrosis factor-α (TNF-α), Macrophage inflammatory protein 1β (MIP-1β) Eotaxin, Interleukin-10 (IL-10), vascular endothelial growth factor (VEGF), Interleukin-2 (IL-2), Interleukin-5 (IL-5), Interleukin-9 (IL-9), Macrophage inflammatory protein 1α

(MIP-1α), monokine induced by gamma interferon (MIG), growth-regulated oncogene-α (GRO-α), LIX (CXCL5), granulocyte colony-stimulating factor (G-CSF), Interleukin-1β (IL-1β) Interleukin-3 (IL-3), Interleukin-6 (IL-6), Interleukin-15 (IL-15), Regulated upon Activation, Normal T cell Expressed, and Secreted (RANTES), macrophage colony-stimulating factor (M-CSF), Interleukin-13 (IL-13), monocyte chemoattractant protein 1 (MCP-1), and/or Interleukin-1α (IL-1α).

Also disclosed herein are methods for controlling brain activity of any preceding aspect, wherein the stimulus is a sensory flicker stimulus.

Also disclosed herein are methods for controlling brain activity of any preceding aspect, wherein the sensory flicker stimulus is at least one of a visual flicker stimulus or an auditory flicker stimulus.

Also disclosed herein are methods for controlling brain activity of any preceding aspect, wherein the sensory flicker stimulus is a combined visual and auditory flicker stimulus.

Also disclosed herein are methods for controlling brain activity of any preceding aspect, wherein the stimulus is transcranial electrical stimulation or transcranial magnetic stimulation.

Also disclosed herein are methods for controlling brain activity of any preceding aspect, wherein the brain activity is induced in at least one of the sensory cortices or deep brain structures (such as, for example, one of the hippocampus, medial temporal lobes, or frontal lobes).

In one aspect, disclosed herein are methods for controlling brain activity of any preceding aspect, wherein the stimulus drives neural activity in the subject's brain (such as, for example, gamma neural activity and/or neural activity in a range between about 20 and 80 Hz).

In one aspect, disclosed herein are methods for controlling brain activity of any preceding aspect, further comprising treating at least one of disease, injury, condition, infection, or normal aging in the subject's brain using the stimulus delivered to the subject. In one aspect, the disease can comprise a neurodegenerative disease (such as, for example, Schizophrenia, Epilepsy, Frontotemporal dementia, vascular dementia, Bipolar disorder, Parkinson's disease, Alzheimer's disease, Autism, Amyotrophic Lateral Sclerosis, Stroke, Traumatic brain injury, bipolar disorder, ischemia reperfusion injury, Multiple sclerosis, and/or Depression). In one aspect, the injury due to inflammation as a result of a neurodegenerative disease. In one aspect, it is understood and herein contemplated that the method further comprises treating a condition (such as, for example, epilepsy, schizophrenia, autism, traumatic brain injury (TBI), bipolar disorder, stroke, or depression) in the subject by modulating the at least one of immunomodulatory signaling or cell survival signaling within the subject.

Also disclosed herein are methods for controlling brain activity of any preceding aspect, wherein the method comprises inducing neuroplasticity of the subject's brain using the stimulus delivered to the subject. In some aspects, delivery of the stimulus such that modulation of the at least one protein is transient.

In one aspect, disclosed herein are methods for controlling brain activity of any preceding aspect, wherein the stimulus upregulates at least one intracellular signaling pathway (such as, for example, a canonical kinase pathway including, but not limited to mitogen activated protein kinase (MAPK) pathway, nuclear factor kappa-light-chain-enhancer of activated B cells (NFκB) pathway, Cyclooxygenase-2 (COX-2) pathway, Nuclear factor (erythroid-derived 2)-like 2 (Nrf2) pathway, Phosphatidylinositol-4,5-bisphosphate 3-kinase (PI3K)/Akt pathway, and/or Janus kinase (JAK)-Signal Transducer and Activator of Transcription (STAT) pathway). In one aspect, the stimulus effects on intracellular signaling modulate (e.g., upregulate or decrease) expression or activity of at least one immediate early gene (such as, for example activity-regulated cytoskeleton-associated protein (ARC) or Fos proto-oncogene (C-Fos)).

In one aspect, disclosed herein are methods of treating a neurological disease, injury, condition, or infection (such as, for example, Schizophrenia, Epilepsy, Frontotemporal dementia, vascular dementia, Bipolar disorder, Parkinson's disease, Alzheimer's disease, Autism, Amyotrophic Lateral Sclerosis, Stroke, Traumatic brain injury, bipolar disorder, ischemia reperfusion injury, Multiple sclerosis, and/or Depression) including inflammatory injury due to the neurological disease, injury, condition, or infection in a subject, comprising exposing the subject to a stimulus; the stimulus induces neural activity in the subject's brain and modulates expression of at least one soluble mediator of cellular activity within the subject, and the stimulus is delivered to the subject for less than one hour.

In one aspect, disclosed herein are methods of treating a neurological disease, injury, condition, or infection of any preceding aspect, wherein the stimulus comprises a 20 Hz sensory flicker stimulus, a 40 Hz sensory flicker stimulus, a random sensory flicker stimulus, a constant sensory stimulus, or any combination thereof. For example, in one aspect, disclosed herein are methods of treating a neurological disease, injury, condition, or infection of any preceding aspect, wherein the stimulus comprises a 40 Hz sensory flicker stimulus or a random sensory flicker stimulus and wherein the neurological condition comprises inflammatory damage resulting from aging, traumatic brain injury, stress, schizophrenia, and/or depression. In one aspect, disclosed herein are methods of treating a neurological disease, injury, condition, or infection of any preceding aspect, wherein the stimulus comprises a 20 Hz sensory flicker stimulus or a random sensory flicker stimulus.

Also disclosed herein are methods of upregulating the expression of a soluble mediator of cellular activity in the brain of a subject comprising exposing a subject to a 40 Hz sensory flicker stimulus, a random sensory flicker stimulus, a constant sensory stimulus, or a combination thereof. In one aspect, disclosed herein are methods of upregulating the expression of a soluble mediator of cellular activity in the brain of a subject of any preceding aspect, wherein the method comprises exposing the cell to 40 Hz sensory flicker stimulus, and wherein the soluble mediator of cellular activity comprises IL-4, IL-7, GM-CSF, IL-12p70, IL-12p40, IFN-γ, LIF, TNF-α, MIP-1β, Eotaxin, MIG, GRO-α, IL-13, MCP-1, IL-1α, LIX, G-CSF, IL-1β, IL-3, IL-6, IL-15, RANTES, and/or M-CSF. In one aspect, disclosed herein are methods of upregulating the expression of a soluble mediator of cellular activity in the brain of a subject of any preceding aspect, wherein the method comprises exposing the cell to random sensory flicker stimulus, and wherein the soluble mediator of cellular activity comprises IL-10, MIG, GRO-α, LIX, G-CSF, IL-1β, IL-3, IL-6, IL-15, RANTES, and/or M-CSF. In one aspect, disclosed herein are methods of upregulating the expression of a soluble mediator of cellular activity in the brain of a subject of any preceding aspect, wherein the method comprises exposing the cell to a constant sensory stimulus, and wherein the soluble mediator of cellular activity comprises VEGF, IL-2, IL-5, IL-9, IL-13, MCP-1, IL-1α, and/or MIP-1α. In one aspect, disclosed herein are methods of upregulating the expression of a soluble mediator of cellular activity in the brain of a subject of any preceding aspect, wherein the method comprises exposing the cell to 40 Hz sensory flicker stimulus or a random sensory flicker stimulus, and wherein the soluble mediator of cellular activity comprises MIG, GRO-α, LIX, G-CSF, IL-1β, IL-3, IL-6, IL-15, RANTES, and/or M-CSF. In one aspect, disclosed herein are methods of upregulating the expression of a soluble mediator of cellular activity in the brain of a subject of any preceding aspect, wherein the method comprises exposing the cell to 40 Hz sensory flicker stimulus or a constant sensory stimulus, and wherein the soluble mediator of cellular activity comprises IL-13, MCP-1, and/or IL-1α.

Also disclosed herein are methods of suppressing the expression of a soluble mediator of cellular activity in the brain of a subject comprising exposing a subject to constant or flickering light at 20 Hz.

Another example method for controlling brain immunomodulatory signaling in a subject is described herein. The method can include delivering a stimulus to the subject. The stimulus can induce neural activity in the subject's brain. Additionally, the stimulus can modulate at least one of immunomodulatory signaling or cell survival signaling within the subject. Optionally, the stimulus can also modulate intracellular signaling that regulates differentiation.

In some implementations, the stimulus is a non-invasive stimulus. Alternatively or additionally, the stimulus is non-pharmacological. Alternatively or additionally, the stimulus drives neural activity in the subject's brain. The neural activity in the subject's brain can be induced in at least one of the sensory cortices. Alternatively or additionally, the neural activity in the subject's brain can be induced in a deep brain structure such as at least one of the hippocampus, medial temporal lobes, frontal lobes, subcortical structures, thalamus, hypothalamus, or brainstem. Alternatively or additionally, the neural activity can be gamma neural activity. Alternatively or additionally, the neural activity in the subject's brain can be neural activity in a range between about 20 and 80 Hz. Optionally, the neural activity in the subject's brain is neural activity at about 40 Hz.

Alternatively or additionally, the method can include treating at least one of disease, injury, infection, or normal aging in the subject's brain using the stimulus delivered to the subject.

Alternatively or additionally, the method can include treating a neurodegenerative disease using the stimulus delivered to the subject. Neurodegenerative diseases include, but are not limited to, Alzheimer's disease, Parkinson's disease, dementia, frontotemporal dementia, vascular dementia, Amyotrophic lateral sclerosis (ALS), and multiple sclerosis (MS).

Alternatively or additionally, the method can include treating a condition in the subject by modulating at least one of immunomodulatory signaling or cell survival signaling within the subject. The condition can include, but is not limited to, epilepsy, schizophrenia, autism, traumatic brain injury (TBI), or normal aging.

Alternatively or additionally, the method can include inducing neuroplasticity of the subject's brain using the stimulus delivered to the subject.

Alternatively or additionally, the stimulus can invoke a response in immunomodulatory signaling within the subject in about 1 hour or less. For example, the stimulus can invoke the response in immunomodulatory signaling within the subject in about 60 minutes or less, 30 minutes or less, or 5 minutes or less.

Alternatively or additionally, the method can include controlling delivery of the stimulus such that immunomodulatory signaling or cell survival signaling modulation is transient.

In some implementations, the stimulus can be a sensory flicker stimulus. Optionally, a frequency of the sensory flicker stimulus is about 40 hertz (Hz). The sensory flicker stimulus can be a visual flicker stimulus. Alternatively or additionally, the sensory flicker stimulus can be an auditory flicker stimulus. Alternatively or additionally, the sensory flicker stimulus can be a combined visual and auditory flicker stimulus.

Alternatively, in some implementations, the stimulus can be transcranial electrical stimulation or transcranial magnetic stimulation.

Alternatively or additionally, the stimulus can upregulate at least one intracellular signaling pathway. In some implementations, the at least one intracellular signaling pathway is a canonical kinase pathway. In some implementations, the at least one intracellular signaling pathway is mitogen activated protein kinase (MAPK) pathway, nuclear factor kappa-light-chain-enhancer of activated B cells (NFκB) pathway, Cyclooxygenase-2 (COX-2) pathway, Nuclear factor (erythroid-derived 2)-like 2 (Nrf2) pathway, Phosphatidylinositol-4,5-bisphosphate 3-kinase (PI3K)/Akt pathway, or Janus kinase (JAK)-Signal Transducer and Activator of Transcription (STAT) pathway.

Alternatively or additionally, the stimulus can alter expression of at least one immunomodulatory cytokine, chemokine, or growth factor. The at least one immunomodulatory cytokine, chemokine, or growth factor can include, but is not limited to monocyte inflammatory protein 2 (MIP-2, chemokine (C—X—C motif) ligand 2, CXCL2), granulocyte colony-stimulating factor (G-CSF, colony-stimulating factor 3, CSF3), regulated on activation, normal T cell expressed and secreted (RANTES, chemokine (C—C motif) ligand 5, CCL5), or interferon gamma (IFN-γ).

Alternatively or additionally, the stimulus effects on intracellular signaling can modulate (e.g., upregulate or decrease) expression or activity of at least one immediate early gene. The at least one immediate early gene can include, but is not limited to, activity-regulated cytoskeleton-associated protein (ARC) or Fos proto-oncogene (C-Fos).

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A illustrates a test group (top) and a control group (bottom) of mice. FIG. 1B illustrates the example experimental protocol.

FIG. 3A illustrates results for mice exposed to flicker for 5-10 minutes. This diagram shows enhanced phosphorylation of Atf-2 and Jnk (Jun kinase) with in the MAPK pathway and of NFκB in the visual cortex, but not in the hippocampus. Moreover, MAPK pathway signaling was suppressed after 60 minutes (min) of flicker as shown in FIG. 3B. All data are z-scored. Each row represents one mouse and each column represents one analyte. FIGS. 3C and 3D illustrate results for mice exposed to flicker for 30 min (FIG. 3C) or 60 min (FIG. 3D), which showed increased expression of multiple immunomodulatory cytokines, including MIP-2, and RANTES, among others. After 60 minutes of flicker MAPK intracellular signaling is decreased and cytokine expression is increased. All data are z-scored. Each row represents one mouse and each column represents one analyte.

FIG. 5 illustrates mice exposed to lights flickering at 40 Hz, which drove neural spiking in visual cortex to increase and decrease at 40 hertz (Hz) as lights turned off and on.

FIG. 6A shows fraction of spikes as a function of auditory flicker in CA1 with spiking rate peaks indicated with asterisks (FIG. 6A, left side), percent recording sites with periodic responses to no stimulation or flicker stimulation (FIG. 6A, center), and distribution of depth of modulation for periodic recording sites during stimulation (FIG. 6A, right side, n=772). FIG. 6B shows spike modulation by auditory and light flicker stimulus in CA1 with spiking rate peaks indicated with asterisks (FIG. 6B, left side), percent recording sites with periodic responses to no stimulation or flicker stimulation (FIG. 6B, center), and distribution of depth of modulation for periodic recording sites during stimulation (FIG. 6B, right side, n=928). Recording sites were determined to have either a periodic or a non-periodic response, where periodic recording sites were defined as those for which all intervals between spiking rate peaks (left plots) fell between 22.5-27.5 ms. **** $p<0.0001$, Wilcoxon ranksum test. Data recorded from 12 recording depths in CA1 from 9 sessions in 4 mice.

FIG. 7A is a heatmap of 32 cytokines quantified in the visual cortex from mice that had been exposed to either 60 min of visual flicker or dark (data are z-scored). FIG. 7B is a plot of multivariate discriminant partial least squares regression (D-PLSR), which was able to identify an axis of cytokines, LV1, which distinguished between visual flicker and dark animals. FIG. 7C illustrates the axis, LV1, distinguishing dark from flicker animals consists of a profile of cytokines that correlate with visual flicker or dark. The larger the magnitude of each bar, the greater the correlation.

As shown in FIG. 8A, after 5 min of visual sensory flicker, increased signaling within the MAPK and NFκB pathways is observed in the visual cortex, but not the hippocampus. FIG. 8B a plot of multivariate discriminant partial least squares regression (D-PLSR). D-PLSR identifies an LV1 signaling axis that distinguishes 5 min flicker in the visual cortex from the HPC. The axis consisted of MAPK and NFκB signals correlated with visual flicker. By 10 min, signaling in LV1 was reduced to be similar to that in the HPC. FIG. 8C shows an immunohistochemistry (IHC) analysis. IHC revealed that phospho-NFκB localized to NeuN labeled neurons (blue: Dapi, green: NeuN, red: NFκB).

In FIG. 9A animals are exposed to different forms of sensory flicker while performing neural recordings of many cells to optimize sensory flicker methods to drive neural activity in hippocampus. In FIG. 9B shows that it is determined how prolonged sensory flicker alters microglia, functional connections between neurons, neural codes, and deficits in AD mice.

FIG. 10A shows SWRs per time for 5XFAD mice (green) and WT littermates (black), FIG. 10B shows the average SWR-triggered spectrograms showing gamma during SWRs is stronger in 5XFAD (yellow area, left) than WT (blue area, right), (10C), Gamma power during SWRs, (10D), Above: fraction of spikes during SWRs as a function of gamma phase (mean+/−s.e.m.). Below: depth of gamma spiking modulation during SWRs. All statistical tests were Wilcoxon rank sum tests.

FIGS. 11A-11C show head-fixed recording and behavior methods. FIG. 11A shows in the virtual reality (VR) behavior paradigm, a head-fixed mouse runs on a spherical treadmill while a virtual environment is projected on the screen around him and is updated based on his movement. The head-fixed approach facilitates high throughput neural recordings. FIG. 11B shows single shank 32 channel silicone probe (left) with recorded spikes from each channel (right) and different single cells shown in different colors. FIG. 11C shows a typical LFP trace. Using this approach, local field potentials have been recorded (to detect SWRs, gamma, and other oscillations), spiking of many single cells simultaneously and combined these recordings with optogenetic stimulation.

FIGS. 12A-12C show electrophysiological recordings of spiking activity in single neurons. FIG. 12A shows typical clusters of spikes (dots) from one HPC recording using a 32-channel silicone probe. This recording yielded 54 well-isolated clusters. Five example clusters, each a different color, are shown. FIG. 12B shows firing rate over time, shown here for 4 example clusters, is stable over a 60 min recording. FIG. 12C shows putative interneurons and pyramidal cells can be distinguished on the basis of their spike waveform widths and average firing rates. Putative pyramidal cells have a wider spike width and lower firing rate (dots in bottom right of plot), while putative interneurons have narrow spike width and a wide range of firing rates (dots on left of plot). The plot shows two clearly distinct distributions of putative interneurons and pyramidal cells. Putative PV interneurons are fast-spiking and this recording yielded only two putative PV-interneurons (two dots on top left). Neuron types are confirmed with optogenetic tagging.

FIGS. 15A-15D show VR learning paradigm. A new VR behavioral paradigm is developed in which animals must lick in the right location, or reward zone, in the track to receive the reward (15A and 15B). Animals are found to learn the correct place to seek reward over training (lick more in reward zones, (15C), and use visual cues to solve the task (perform worse without visual cues, (15D). FIG. 15A shows the track with reward zones marked with white arrows. FIG. 15B shows an animal's position over time on the first (left) and sixth (right) day of training showing that the animal performed more trials per time and licked more often in the reward zones on the sixth day. FIG. 15C shows the percent licks in the reward zones over 7 days of training (n=5 mice). FIG. 15D shows the track with (above) and without (below) visual cues (left). Percent licks in the reward zones were significantly higher in the track with visual cues than without (right, n=5 mice, p<0.05). Error bars, mean+/−s.e.m.

FIG. 17A shows protein expression of 32 cytokines in the visual cortex after 1 hr of sensory flicker (z-scored). FIG. 17B shows 40 Hz flicker promotes expression of certain cytokines (e.g, MIG), while random flicker promotes expression of IL-10 and constant light promotes VEGF (arrows in 17A).

FIG. 19 shows GSEA identified 31 significantly enriched gene sets (of 492) after 1 hr of 40 Hz flicker.

FIG. 20A shows that it is shown that gamma activity in neurons stimulates MAPK and NFκB signaling that together regulate synaptic connections and microglial transformation. FIG. 20B shows Luminex multiplexed immunoassays revealed increased signaling within the MAPK and NFκB pathways in the visual cortex after 5 min of 40 Hz flicker compared to random stimulation or mice kept in the dark (data are z-scored). FIG. 20C shows 40 Hz flicker significantly increased Erk phosphorylation, which was suppressed by upstream inhibition of Mek using a blood-brain barrier penetrant small molecule (100 mg/kg SL327) (one way ANOVA with post-hoc correction). FIG. 20D shows IHC showed phospho-NFκB localized to NeuN labeled neurons after 5 min of 40 Hz flicker (blue: Dapi, green: NeuN, red: NFκB)

FIG. 21 shows Luminex analysis was used to quantify 32 cytokines in the visual cortex from mice that had been exposed to either 60 min of visual 40 Hz flicker, random flicker, 20 Hz flicker, or constant light. Bar plots show selected significant selected cytokines.

FIG. 23A show the example putative single unit spiking response to 40 Hz auditory stimulation with many 10 second stimulation blocks shown wrapped every 100 ms, left. Examples of spiking response to four consecutive pulses, right.

40 Hz vs. No Stim, 40 Hz vs. Random; Kolmogorov-Smirnov test; 2 units had 40 Hz stim RS values >30). FIG. 23R shows the same as (23F) for mPFC.

FIGS. 24A-24U shows 20 Hz and 80 Hz auditory stimulation modulates activity in AC, CA1, and mPFC. FIG. 24A shows mean LFP response to auditory mapping tones used to detect auditory cortex (left). The blue region indicates when the 50 ms mapping tone played. Example of a clustered putative single unit (right). FIG. 24E shows the firing rate response of all isolated single units in AC to Random, 20 Hz, 40 Hz, and 80 Hz auditory stimulation. Z-scored response to four consecutive stimulus cycles is shown. Units are ordered by their average stimulus phase preference in the analyzed four cycles. White dashed lines indicate auditory pulse timing. FIG. 24F shows vector strength distribution of 20 Hz and 80 Hz auditory stimulation vs. no stimulation condition (left, $P < 0.00005$ 20 Hz vs. No Stim, 80 Hz vs. No Stim; Kolmogorov-Smirnov test; 11 units had 20 Hz stim VS values greater than 0.25; 6 units had 80 Hz stim VS values greater than 0.25) and Rayleigh statistic distribution of 20 Hz and 80 Hz auditory stimulation vs. no stimulation (right, $P < 0.00005$ 20 Hz vs. No Stim, 80 Hz vs. No Stim; Kolmogorov-Smirnov test; 74 units had 20 Hz stim RS values greater than 30; 41 units had 80 Hz stim RS values greater than 30). FIG. 24G shows dstribution of within cell differences in vector strength values between all frequencies of auditory stimulation (left, $P < 0.000025$ 20 Hz-80 Hz, 20 Hz-40 Hz, 40 Hz—Random; 40 Hz-80 Hz n.s.; Wilcoxon signed rank test for zero median). Within cell differences in Rayleigh statistic values between all frequencies of auditory stimulation (right, $P < 0.000025$ 20 Hz-80 Hz, 20 Hz-40 Hz, 40 Hz—Random; 40 Hz-80 Hz n.s.; Wilcoxon signed rank test for zero median). FIG. 24S shows the same as (24E) for mPFC. FIG. 24T shows the same as (24F) for mPFC (left, $P < 0.00005$ 20 Hz vs. No Stim, 80 Hz vs. No Stim; Kolmogorov-Smirnov test; 4 units had 20 Hz stim VS values greater than 0.25; right, $P < 0.00005$ 20 Hz vs. No Stim, 80 Hz vs. No Stim; Kolmogorov-Smirnov test; 5 units had 20 Hz stim RS values greater than 30; 3 units had 80 Hz stim RS values greater than 30). FIG. 24U shows the same as (24G) for mPFC (left, $P < 0.000025$ 40 Hz—random, all others n.s.; Wilcoxon signed rank test for zero median; right, **$P < 0.000025$ 40 Hz—Random, all others n.s.; Wilcoxon signed rank test for zero median).

FIG. 25A firing rate modulation of a single unit during 40 Hz audio-visual stimulation (left). Vector strength of responses to 40 Hz A+V stimulation, random A+V stimulation, and no stimulation periods (right, **$P < 0.00005$ 40 Hz vs. No Stim, 40 Hz vs. Random; Kolmogorov-Smirnov test; 9 units had 40 Hz stim VS values greater than 0.25; 3 units had random stim VS values greater than 0.25. In all statistical tests for panels A-C, results are significant after controlling for multiple comparisons using the Bonferroni correction unless otherwise stated). FIG. 25B shows the same as A for CA1 (right, $P < 0.00005$ 40 Hz vs. No Stim, 40 Hz vs. Random; Kolmogorov-Smirnov test; 8 units and 3 units had VS values >0.25 for 40 Hz or random stim, respectively). FIG. 25C shows same as A for mPFC (right, **$P < 0.00005$ 40 Hz vs. No Stim, 40 Hz vs. Random; Kolmogorov-Smirnov test; 5 units had 40 Hz stim VS values >0.25).

FIGS. 26A-26U. 40 Hz combined auditory and visual stimulation modulates spiking activity in AC, CA1, and mPFC. FIG. 26A shows power spectral density (PSD) response to 40 Hz audio-visual flicker stimuli and no stimulation periods, with mean and standard deviation across recording days (left), power spectrum LFP response to audio-visual flicker stimulation of all recording days in AC (recording site with largest 40 Hz peak during 40 Hz audio-visual flicker per recording depth is shown, Methods) (right). FIG. 26B shows the firing rate modulation of putative single unit shown in FIG. 6A to audio-visual random stimulation, Rayleigh statistic distribution of single unit response to 40 Hz audio-visual stimulation (right, **$P < 0.00005$ 40 Hz vs. No Stim, 40 Hz vs. Random; Kolmogorov-Smirnov test; 40 units had 45 Hz stim RS values greater than 30; 5 units had random stim RS values greater than 30. In all statistical tests, significance remains after controlling for multiple comparisons using the Bonferroni correction, unless otherwise stated). FIG. 26C shows the firing rate modulation of a putative single unit in response to 20 Hz audio-visual flicker stimulation (left, green) and 80 Hz audio-visual flicker stimulation (right, purple). FIG. 26O shows the same as (26A) for mPFC. FIG. 26P shows the same as (26B) for mPFC (right, $P<0.00005$ 40 Hz vs. No Stim, 40 Hz vs. Random; Kolmogorov-Smirnov test; 1 unit had a 40 Hz stim RS value greater than 30). FIG. 26Q shows the same as (26C) for mPFC. FIG. 26U shows the same as (26G) for mPFC (left, $P<0.000025$ 40 Hz—random; all others n.s.; Wilcoxon signed rank test for zero median; right, **$P<0.000025$ 40 Hz—Random; all others n.s.; Wilcoxon signed rank test for zero median).

DETAILED DESCRIPTION

Figure 1:
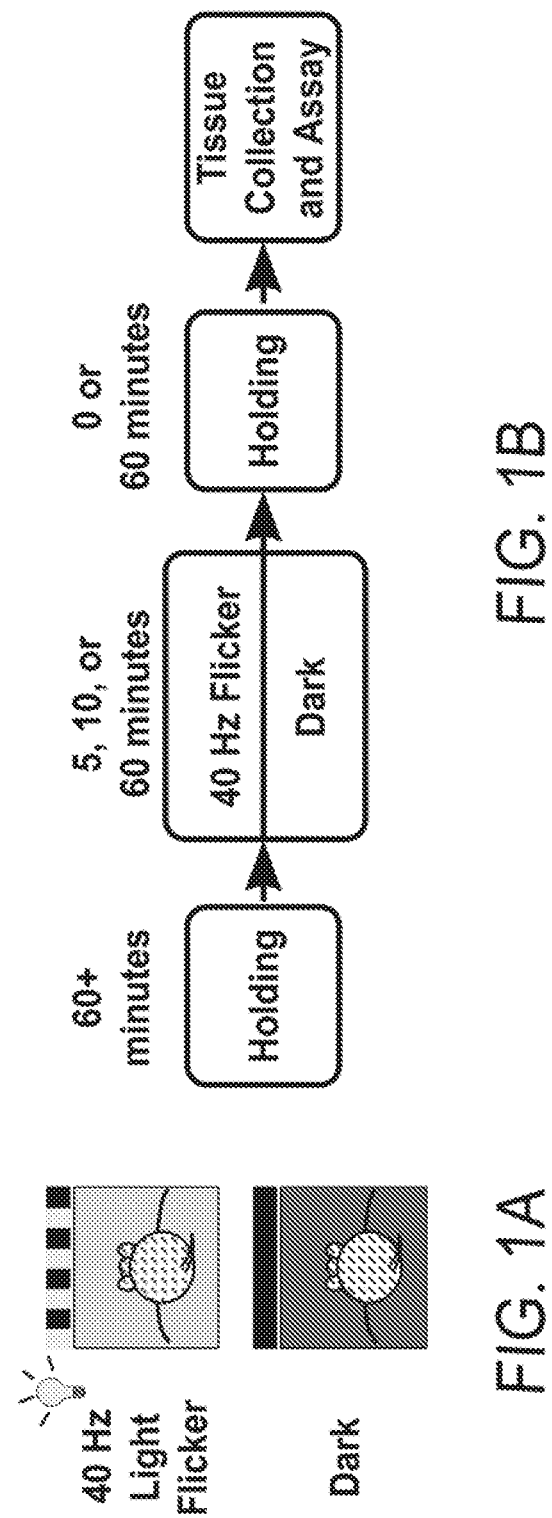
FIGS. 1A-1B illustrate an example experimental protocol according to an implementation described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise.

The term "comprising" and variations thereof as used herein is used synonymously with the term "including" and variations thereof and are open, non-limiting terms.

The terms "optional" or "optionally" used herein mean that the subsequently described feature, event or circumstance may or may not occur, and that the description includes instances where said feature, event or circumstance occurs and instances where it does not.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

An "increase" can refer to any change that results in a smaller gene expression, protein expression, amount of a symptom, disease, composition, condition, or activity. A substance is also understood to increase the genetic output of a gene when the genetic output of the gene product with the substance is less relative to the output of the gene product without the substance. Also, for example, an increase can be a change in the symptoms of a disorder such that the symptoms are less than previously observed. An increase can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

In this specification and in the claims which follow, reference will be made to a number of terms which shall be defined to have the following meanings:

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

As described above, driving gamma frequency activity recruits microglial engulfment and clearance of Aβ in Alzheimer's disease (AD) mouse models. And gamma deficits may be an integral component of AD pathology. These findings indicate that gamma oscillations play important dual roles in promoting and coordinating neural activity and neural immune function. However, the mechanism by which gamma activity can play this dual role in neural coding and neural immunity was previously completely unknown. In addition, the prior study showed no change in immunomodulatory signaling as a result of driving gamma frequency activity. As described herein, molecular mechanisms by which gamma oscillations regulate both immune activity and synaptic plasticity have been identified. There is an unmet need to understand the roles and mechanisms of gamma activity because gamma activity is dysfunctional both in humans and animal models of AD.1-4

Figure 4:
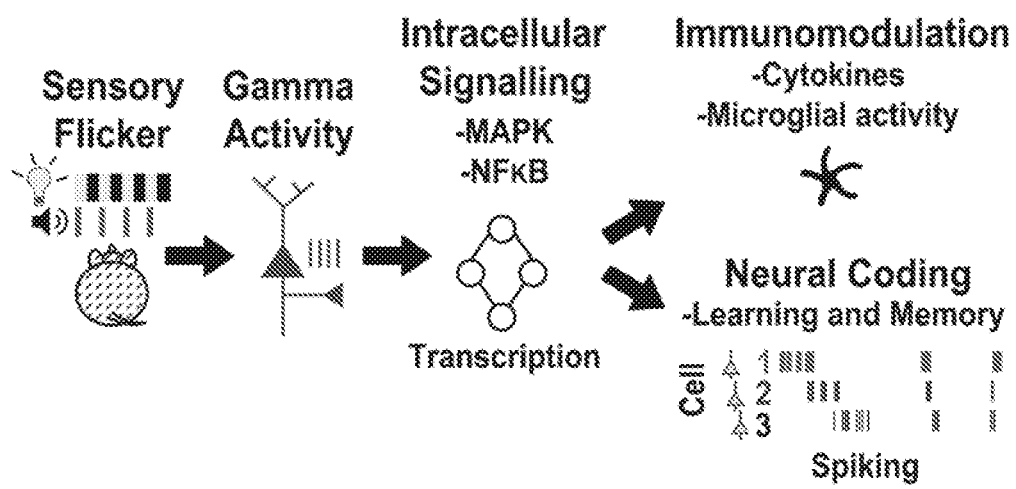
FIG. 4 is a diagram illustrating how gamma oscillations trigger common intracellular pathways (e.g., MAPK and NFκB pathways) that induce genes governing diverse functions, including cell survival, microglial recruitment and neural codes essential for learning and memory.

In an example described below, gamma activity can be driven non-invasively by presenting animals (e.g., mice) with 40 Hz sensory flicker (rapid strobe light) stimulation.1 Sensory flicker stimulation is paired with techniques to profile intra- and extracellular signaling proteins that regulate neuronal and immune function and characterize neural electrical activity in response to gamma stimulation. For example, intracellular signaling pathways and immunomodulatory cytokines in the visual cortex have been profiled after exposing animals to light flicker. Sensory flicker triggers a rapid spike (e.g., in <5 min) in a subset of pathways (e.g., MAPK, NFκB) followed by increased production of cytokines known to regulate microglia within an hour. Over a similar time course of sensory flicker exposure, neural electrical activity dramatically increases, suggesting neural circuits are undergoing plasticity.1 These data suggest that gamma oscillations trigger common intracellular pathways that induce genes which govern both immune function and synaptic plasticity (see e.g., FIG. 4).

An example for driving electrical activity of neurons to alter signaling that governs inflammation, cell survival, plasticity and other cell functions is now described. Flickering light technology was used to induce gamma neural activity in the visual cortex of a mouse's brain, and its effects on inflammatory signals were assessed. Using a systems analysis of visual cortical tissues, the effects of flicker on numerous intracellular inflammatory signals were examined. Flicker at 40 Hz was discovered to trigger a rapid spike (<5 min) in a subset of inflammatory pathways followed by increased production of inflammatory cytokines known to regulate microglia within an hour. These data show that driving neural activity (and in some implementations driving neural activity non-invasively) can be used as a method to manipulate molecular signaling in the brain that controls inflammation. Moreover, these inflammatory pathways and the downstream genes they regulate control diverse beneficial cellular functions, including survival, proliferation, differentiation, plasticity, and neurogenesis, among others. Therefore, this approach to modulate brain inflammation can be used to treat many brain diseases, brain injury, infection, and the effects of normal brain aging. These discoveries have wide-ranging impact at both clinical and basic science levels. For example, driving neural activity to modulate inflammatory signaling can be used to treat neurodegenerative diseases (e.g., Alzheimer's disease). In addition, driving neural activity to modulate inflammatory signaling can be used to treat disorders that involve inflammatory signaling (e.g., schizophrenia), the brain's immune responses, and/or neural activity.

The data collected by the studies described herein shows, for the first time, that sensory stimulation causes changes in intracellular signaling that regulates inflammation and cell survival, proliferation, and differentiation. Furthermore, this data yields that the first evidence that sensory flicker induces a rapid immune response (starting within a few minutes), significantly faster than standard pharmaceutical methods can manipulate inflammatory signaling. In other words, this data shows how inflammatory signals and downstream inflammatory proteins respond to flicker over time.

Flickering lights at gamma frequencies were used to drives strong rhythmic neural activity in visual cortex. Using light flicker to drive gamma in the visual cortex, wild-type C57Bl/6 mice were exposed to light flicker at different frequencies (i.e., test group) or to constant light or a dark chamber (i.e., control group) for different periods of time to characterize the inflammatory signaling response to gamma neural activity. In an example of FIG. 1A, the mice were exposed to flicker or darkness for 5, 10, 30, or 60 minutes, and then the brains were rapidly removed from the mice and the visual cortex and hippocampus were micro-dissected and lysed to extract protein. This is shown in FIG. 1B. The visual cortex is known to be highly sensitive to light flicker, whereas the hippocampus is not and thus served as an internal control.

Figure 2:
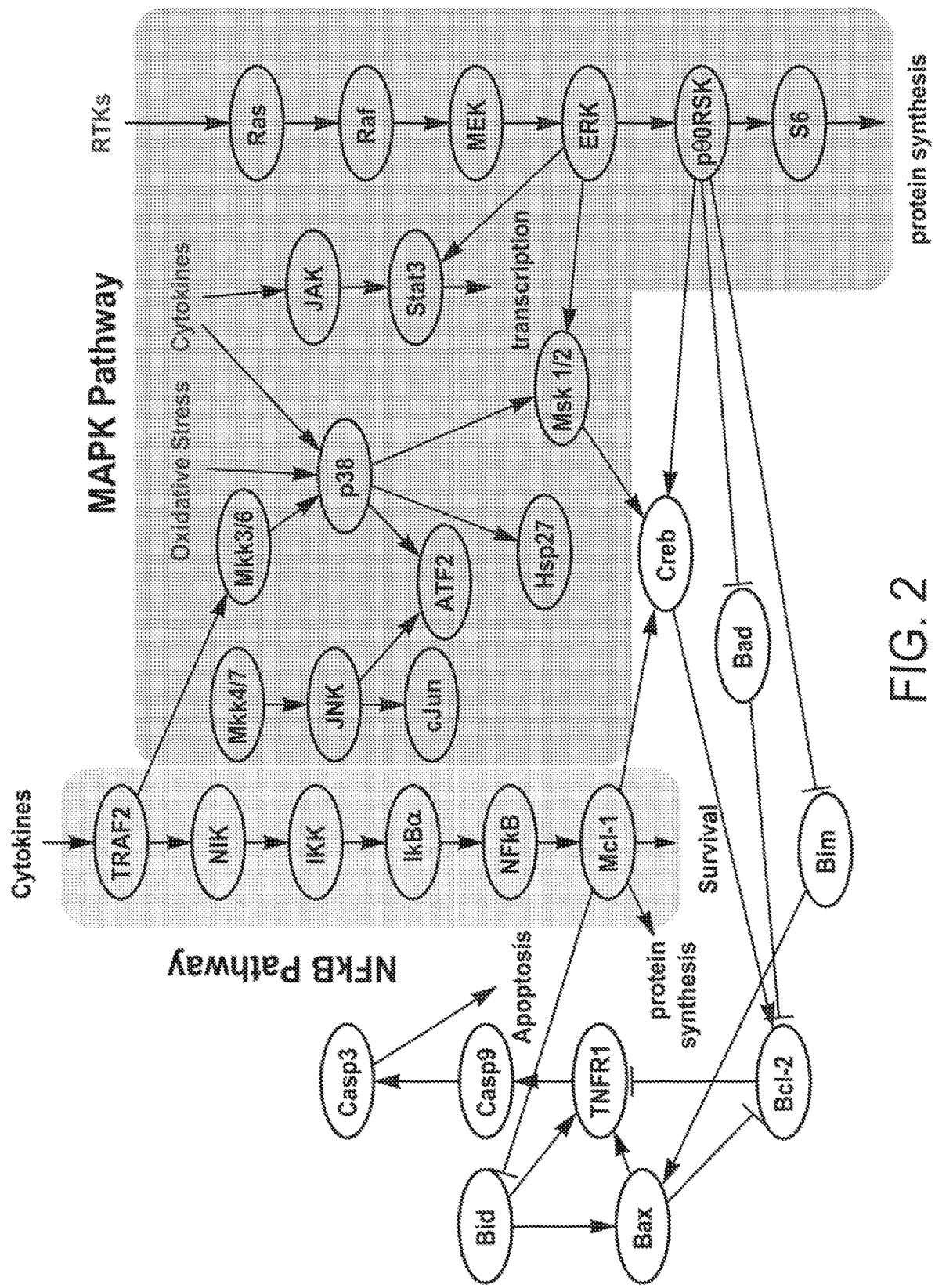
FIG. 2 is a diagram illustrating MAPK and NFκB pathways. These pathways regulate cell survival and protein synthesis, including proteins that regulate inflammation and cell behaviors, such as cytokines and growth factors.

Changes in the mitogen activated protein kinase (MAPK) and nuclear factor kappa-light-chain-enhancer of activated B cells (NFκB) pathways were observed. These intracellular pathways strongly modulate inflammation by regulating gene expression and protein synthesis. This is shown in FIG. 2. Moreover, the MAPK and NFκB pathways also have functions that promote cell survival, proliferation, and cell differentiation. Using multiplexed immunoassays (e.g., using multiplexed assay systems from LUMINEX CORP. of Austin, Texas and EMD MILLIPORE), protein phosphorylation within the MAPK and NFκB pathways following flicker or control conditions were quantified.

Figure 3A:
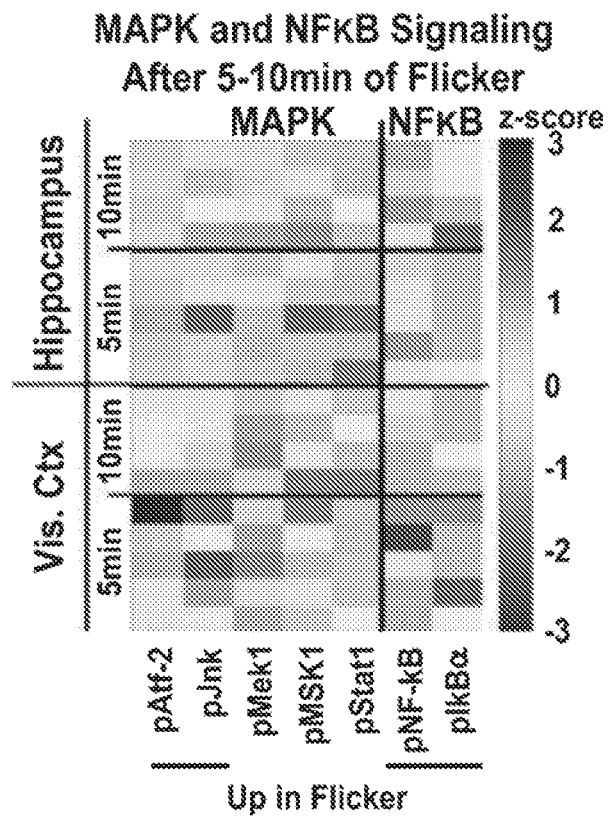
FIGS. 3A-3D are diagrams illustrating how sensory flicker initially stimulates and then suppresses intracellular signaling, leading to expression of cytokines and growth factors.
Figure 3B:
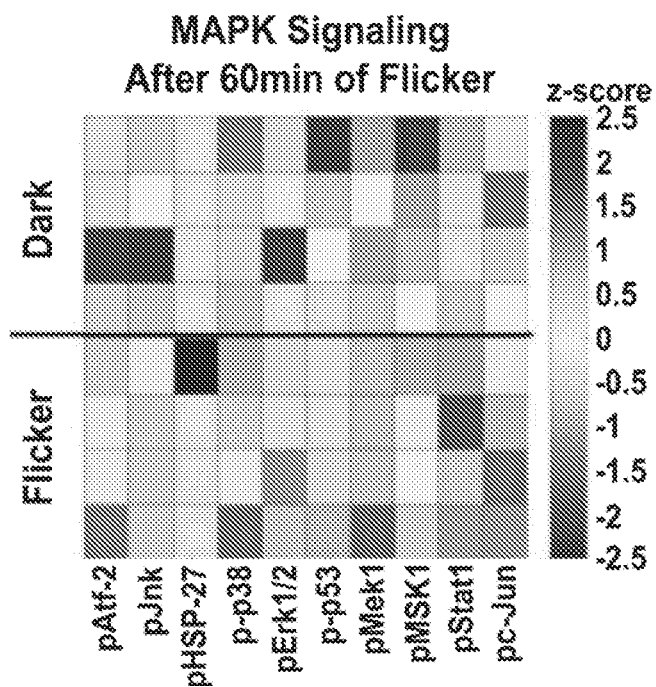
Figure 3C:
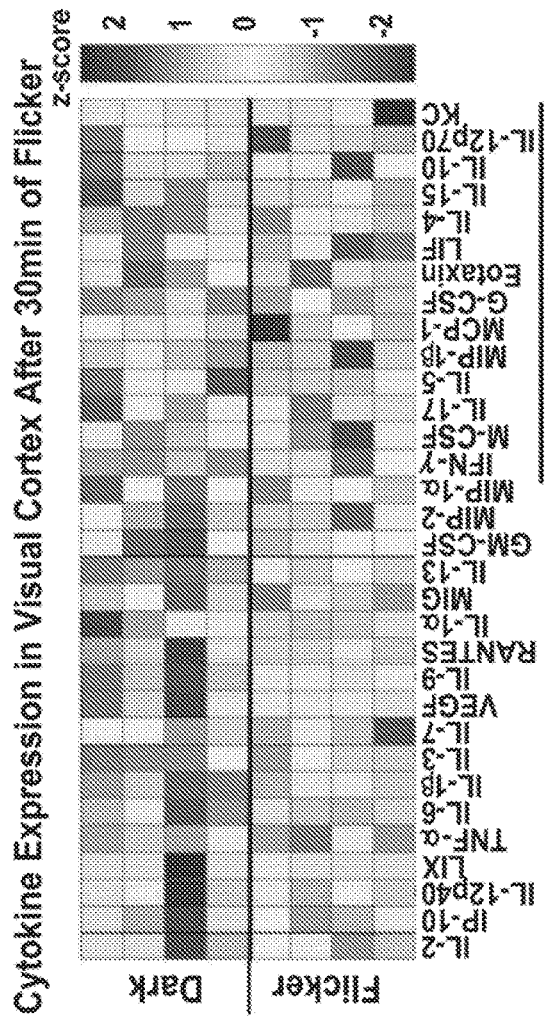
Figure 3D:
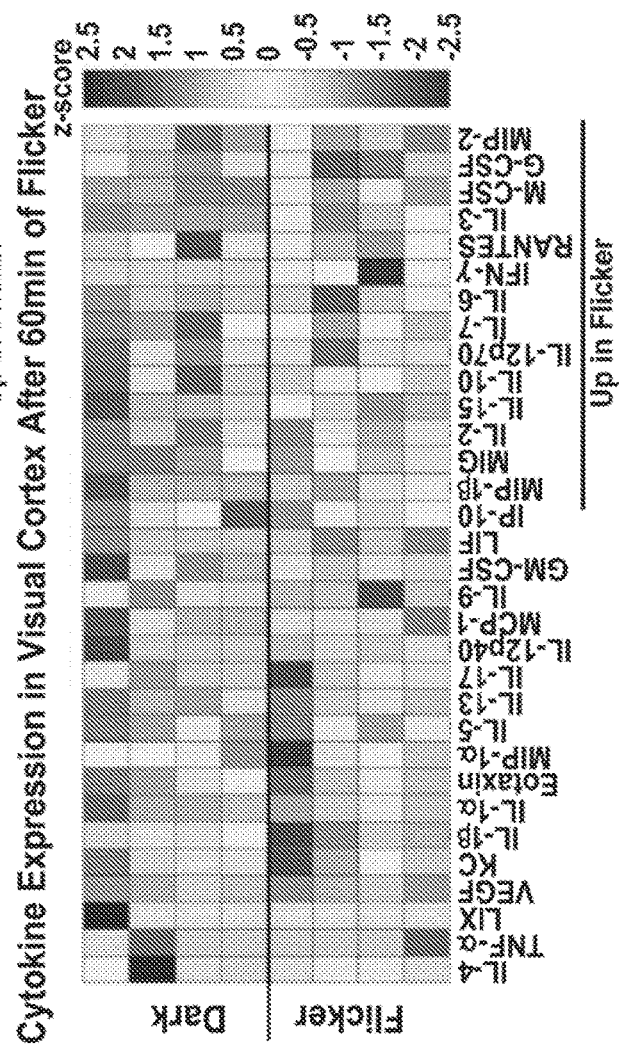

As a result, multiple key effects of flicker stimulation on inflammatory signals were discovered. First, following flicker pro-inflammatory signaling undergoes a rapid transient (~5 min) increase in phosphorylation of Atf-2 and Jnk (Jun kinase) followed by a sustained decrease in signaling. These effects are shown in FIGS. 3A and 3B. FIG. 3B shows the apparent sustained decrease in the MAPK pathway after 60 min of stimulation. Second, inflammatory cytokines increase within about 30 min of flicker exposure and continue to be increased for 2 hr after the start of flicker). These effects are shown in FIGS. 3C and 3D. Signaling within the MAPK and NFκB pathways precedes cytokine expression and is known to regulate immune responses. Therefore, these early intracellular signals are the likely mechanisms that promote cytokine expression and regulate subsequent neuroinflammation.

The cytokines expressed in response to flicker (e.g., RANTES, MIP-2, etc.), are immunomodulatory regulators. Moreover, other factors that increase in response to flicker, such as G-CSF, are neurotrophic. Thus, these results show sensory flicker induces a cascade of signaling involved in brain immune responses, as well as cell survival, proliferation, differentiation, plasticity, and neurogenesis, among others.

Gamma flicker stimulates intracellular signaling that governs neuroinflammation, cell survival, and plasticity. These functions are critical in normal brain function and are dysregulated in neurological conditions associated with injury and disease. Thus, gamma-stimulated modulation of these pathways represents a powerful tool to intervene in numerous conditions and promote brain health.

Example Embodiments

As described above, driving gamma frequency activity recruits microglial engulfment and clearance of Aβ in Alzheimer's disease (AD) mouse models. And gamma deficits may be an integral component of AD pathology. These findings indicate that gamma oscillations play important dual roles in promoting and coordinating neural activity and neural immune function. However, the mechanism by which gamma activity can play this dual role in neural coding and neural immunity was previously completely unknown. In addition, the prior study showed no change in immunomodulatory signaling as a result of driving gamma frequency activity. As described herein, molecular mechanisms by which gamma oscillations regulate both immune activity and synaptic plasticity have been identified. There is an unmet need to understand the roles and mechanisms of gamma activity because gamma activity is dysfunctional both in humans and animal models of AD.

In an example described below, gamma activity can be driven non-invasively by presenting animals (e.g., mice) with 40 Hz sensory flicker (rapid strobe light) stimulation.[1] Sensory flicker stimulation is paired with techniques to profile intra- and extracellular signaling proteins that regulate neuronal and immune function and characterize neural electrical activity in response to gamma stimulation. For example intracellular signaling pathways and immunomodulatory cytokines in the visual cortex have been profiled after exposing animals to light flicker. Sensory flicker triggers a rapid spike (e.g., in <5 min) in a subset of pathways (e.g., MAPK, NFκB) followed by increased production of cytokines known to regulate microglia within an hour. Over a similar time course of sensory flicker exposure, neural electrical activity dramatically increases, suggesting neural circuits are undergoing plasticity. These data suggest that gamma oscillations trigger common intracellular pathways that induce genes which govern both immune function and synaptic plasticity (see e.g., FIG. 4).

An example for driving electrical activity of neurons to alter signaling that governs inflammation and other cell functions, such as survival and plasticity, is now described. Flickering light technology was used to induce gamma neural activity in the visual cortex of a mouse's brain, and its effects on inflammatory signals were assessed. Using a systems analysis of visual cortical tissues, the effects of flicker on numerous intracellular inflammatory signals were examined. Flicker was discovered to trigger a rapid spike (<5 min) in a subset of inflammatory pathways followed by increased production of inflammatory cytokines known to regulate microglia within an hour. These data show that driving neural activity (and in some implementations driving neural activity non-invasively) can be used as a method to manipulate molecular signaling in the brain that controls inflammation. Moreover, these inflammatory pathways and the downstream genes they regulate control diverse beneficial cellular functions, including survival, proliferation, differentiation, plasticity, and neurogenesis, among others. Therefore, this approach to modulate brain inflammation can be used to treat many brain diseases, brain injury, infection, and the effects of normal brain aging. These discoveries have wide-ranging impact at both clinical and basic science levels. For example, driving neural activity to modulate inflammatory signaling can be used to treat neurodegenerative diseases (e.g., Alzheimer's disease). In addition, driving neural activity to modulate inflammatory signaling can be used to treat disorders that involve inflammatory signaling (e.g., schizophrenia), the brain's immune responses, and/or neural activity.

The data collected by the studies described herein shows, for the first time, that sensory stimulation causes changes in intracellular signaling that broadly regulates expression of genes involved in inflammation and cell survival, proliferation, and differentiation. Furthermore, this data yields that the first evidence that sensory flicker induces a rapid immune response (starting within a few minutes), significantly faster than standard pharmaceutical methods can manipulate inflammatory signaling. In other words, this data shows how inflammatory signals and downstream inflammatory proteins respond to flicker over time.

Flickering lights at gamma frequencies were used to drives strong gamma oscillations in visual cortex. Using light flicker to drive gamma in the visual cortex, wild-type C57BI/6 mice were exposed to light flicker (i.e., test group) or to a dark chamber (i.e., control group) for different periods of time to characterize the inflammatory signaling response to gamma neural activity. This is shown in FIG. 1A. The mice were exposed to flicker or darkness for 5, 10, 30, or 60 minutes, and then the brains were rapidly removed from the mice and the visual cortex and hippocampus were micro-dissected and lysed to extract protein. This is shown in FIG. 1B. The visual cortex is known to be highly sensitive to light flicker, whereas the hippocampus is not and thus served as an internal control.

Changes in the mitogen activated protein kinase (MAPK) and nuclear factor kappa-light-chain-enhancer of activated B cells (NFκB) pathways were observed. These intracellular pathways strongly modulate inflammation by regulating gene expression and protein synthesis. This is shown in FIG. 2. Moreover, the MAPK and NFκB pathways also have functions that promote cell survival, proliferation, and cell differentiation. Using multiplexed immunoassays (e.g., using multiplexed assay systems from LUMINEX CORP. of Austin, Texas and EMD MILLIPORE), protein phosphorylation within the MAPK and NFκB pathways following flicker or control conditions were quantified.

As a result, multiple key effects of flicker stimulation on inflammatory signals were discovered. First, following flicker pro-inflammatory signaling undergoes a rapid transient (~5 min) increase in phosphorylation of Atf-2 and Jnk (Jun kinase) followed by a sustained decrease in signaling. These effects are shown in FIGS. 3A and 3B. FIG. 3B shows the apparent sustained decrease in the MAPK pathway after 60 min of stimulation. Second, inflammatory cytokines increase within about 30 min of flicker exposure and continue to be increased for 2 hr after the start of flicker). These effects are shown in FIGS. 3C and 3D. Signaling within the MAPK and NFκB pathways precedes cytokine expression and is known to regulate immune responses. Therefore, these early intracellular signals are the likely mechanisms that promote cytokine expression and regulate subsequent neuroinflammation.

The cytokines expressed in response to flicker (e.g., RANTES, MIP-2, etc.), are immunomodulatory regulators. Moreover, other factors that increase in response to flicker, such as G-CSF, are neurotrophic. Thus, these results show sensory flicker induces a cascade of signaling involved in brain immune responses, as well as cell survival, proliferation, differentiation, plasticity, and neurogenesis, among others.

Gamma flicker stimulates intracellular signaling that governs neuroinflammation, cell survival, and plasticity. These functions are critical in normal brain function and are dysregulated in neurological conditions associated with injury and disease. Thus, gamma-stimulated modulation of these pathways represents a powerful tool to intervene in numerous conditions and promote brain health.

An example method for controlling brain immunomodulatory signaling in a subject is described below. The method can include delivering a stimulus to the subject. Optionally, the stimulus is a non-invasive stimulus such as a sensory stimulus, which is described in detail below. Additionally, the stimulus can be non-pharmacological. The stimulus drives neural activity in the subject's brain. In particular, the stimulus can induce gamma activity in the subject's brain. Gamma activity is neural oscillation with a frequency between 20 Hz and 100 Hz. In some implementations, the gamma activity is neural oscillation in a range between 20 Hz and 80 Hz. Optionally, the gamma activity is neural oscillation at about 40 Hz. Gamma activity is known in the art and is therefore not described in further detail herein. The gamma activity can be induced in the sensory cortices of the subject's brain. Alternatively or additionally, the gamma activity can be induced in a deep brain region such as the hippocampus, medial temporal lobes, frontal lobes, subcortical structures, thalamus, hypothalamus, or brainstem. This disclosure contemplates that the gamma activity can be induced in other brain regions or parts of the nervous system. In other words, inducing gamma activity in the sensory cortices, hippocampus, medial temporal lobes, and/or frontal lobes are provided only as examples.

As described above, the stimulus can optionally be a sensory flicker stimulus (sometimes referred to herein as "sensory flicker"). Sensory flicker (e.g., visual, auditory, etc.) is used to induce gamma activity (e.g., about 40 Hz neural oscillations). In some implementations, the sensory flicker stimulus is visual flicker. Flickering light at gamma frequencies is known to drive gamma oscillations in the visual cortex of the brain. And, although the effects are weaker, flickering light at gamma frequencies is known to drive gamma oscillations in the hippocampus (HPC). For example, a visual flicker stimulus can optionally be produced by flashing a light (e.g., white light) for 12.5 millisecond (ms) every 25 ms. It should be understood that the color and/or parameters (e.g., frequency, period, duty cycle, etc.) of the visual flicker stimulus are provided only as examples and can have other characteristics/values while still inducing gamma activity. In other implementations, the sensory flicker stimulus is auditory flicker. Auditory sensory flicker can drive gamma oscillations in the HPC. For example, an auditory flicker stimulus can optionally be produced by sounding a 1 ms long 10 kHz tone every 25 ms. It should be understood that the tonal frequency and/or parameters (e.g., frequency, period, duty cycle, etc.) of the auditory flicker stimulus are provided only as examples and can have other characteristics/values while still inducing gamma activity. In yet other implementations, the sensory flicker can be combined visual and auditory flicker. For example, a combined visual and auditory flicker stimulus can optionally be produced by flashing a light and sounding a tone every 25 ms.

Alternatively, the stimulus can be transcranial electrical stimulation (TES). TES delivers electrical currents to the brain via one or more electrodes. The electrical currents are supplied by a stimulator. The electrical currents generate an electrical field that drives neural activity in the brain. TES is known in the art and is therefore not described in detail below. Alternatively, the stimulus can be transcranial magnetic stimulation (TMS). TMS uses varying magnetic fields to drive electrical activity in the brain via electromagnetic induction. TMS is provided by placing a magnetic field generator (e.g., coil) near the subject's head. A varying electric current is supplied to the coil by a stimulator. TMS is known in the art and is therefore not described in detail below. It should be understood that sensory stimuli (e.g., audio and/or visual flicker), TES, and TMS are provided only as example stimulation techniques. This disclosure contemplates using other techniques for delivering stimulation to the subject including, but not limited to, optogenetic stimulation, magnogenetic stimulation, invasive electrical stimulation, mechanical stimulation, focused ultrasound, or peripheral nerve stimulation.

Additionally, the stimulus can modulate at least one of immunomodulatory signaling or cell survival signaling within the subject. Immunomodulatory signaling can include pro-inflammatory or anti-inflammatory signaling. The stimulus may also modulate intracellular signaling that regulates differentiation. As described herein, the stimulus modulates intracellular signaling, which regulates one or more cellular functions including, but not limited to, neuroinflammation (e.g., pro- or anti-inflammatory), cell survival, and differentiation. Neuroinflammation, cell survival, and differentiation are only provided as examples of cellular functions regulated by the intracellular signaling modulated by the stimulus described herein. Optionally, delivery of the stimulus can be controlled such that immunomodulatory signaling and/or cell survival signaling modulation is transient. In other words, the stimulus is controlled such that immunomodulatory signaling and/or cell survival signaling is turned on and turned off. It should be understood that a chronically activated immune response would be undesirable in most cases. The stimulus can upregulate at least one intracellular signaling pathway. This is shown by FIGS. 2, 3A, and 3B, which illustrate MAPK and NFκB signaling response to sensory flicker. In some implementations, the intracellular signaling pathway can be a canonical kinase pathway. In some implementations, the intracellular signaling pathway can be mitogen activated protein kinase (MAPK) pathway, nuclear factor kappa-light-chain-enhancer of activated B cells (NFκB) pathway, Cyclooxygenase-2 (COX-2) pathway, Nuclear factor (erythroid-derived 2)-like 2 (Nrf2) pathway, Phosphatidylinositol-4,5-bisphosphate 3-kinase (PI3K)/Akt pathway, or Janus kinase (JAK)-Signal Transducer and Activator of Transcription (STAT) pathway. It should be understood that the intracellular signaling pathways described herein are provided only as examples.

Alternatively or additionally, the stimulus can alter expression of at least one immunomodulatory cytokine, chemokine, or growth factor. This is shown by FIGS. 3C and 3D, which illustrate increased expression of cytokines that regulate inflammation in response to sensory flicker. For example, the at least one immunomodulatory cytokine, chemokine, or growth factor is MIP-2, G-CSF, RANTES, or IFN-γ. It should be understood that the immunomodulatory cytokines, chemokines, or growth factors described herein are provided only as examples.

Alternatively or additionally, the stimulus effects on intracellular signaling can modulate (e.g., upregulate or decrease) expression or activity of at least one immediate early gene. For example, the at least one immediate early gene can include, but is not limited to, activity-regulated cytoskeleton-associated protein (ARC) or Fos proto-oncogene (C-Fos). It should be understood that the immediate early genes described herein are provided only as examples.

As described herein, the stimulus can invoke a more rapid immunomodulatory response as compared to conventional methods. For example, pharmacological agents (i.e., drugs) used to alter inflammatory signaling, e.g., via injection, may take hours to reach the brain and alter immunomodulatory signaling. Moreover, the stimulation method described herein is not limited by the blood-brain barrier as are many pharmacologic agents. In some implementations, the sensory stimulus described herein can invoke a response in immunomodulatory signaling within the subject in about 1 hour or less (e.g., sustained decrease in MAPK pathway in FIG. 3B; increased cytokine expression in FIG. 3D). In some cases, the stimulus can invoke the response in immunomodulatory signaling within the subject in about 30 minutes or less (e.g., increased cytokine expression in FIG. 3C). In yet other cases, the stimulus can invoke the response in immunomodulatory signaling within the subject in about 5 minutes or less (e.g., rapid transient increase in phosphorylation of Atf-2 and Jnk in FIG. 3A).

The method described herein can be used to modulate, by driving neural activity, intracellular signaling that regulates neuroinflammation and also cell survival, proliferation, and differentiation. Accordingly, the method can include treating at least one of disease, injury, infection, or normal aging in the subject's brain using the stimulus delivered to the subject. For example, the method can include treating a neurodegenerative disease. Neurodegenerative diseases include, but are not limited to, Alzheimer's disease, Parkinson's disease, dementia, frontotemporal dementia, vascular dementia, Amyotrophic lateral sclerosis (ALS), and multiple sclerosis (MS). Alternatively or additionally, a new class of conditions can be treated since the stimulus can modulate inflammatory signaling within the subject. In particular, the method described herein can include treating conditions that involve inflammatory signaling including, but not limited to, epilepsy, schizophrenia, autism, traumatic brain injury (TBI), or normal aging. Alternatively or additionally, the method can include inducing neuroplasticity of the subject's brain using the stimulus delivered to the subject. The MAPK pathway, which is one of the intracellular pathways shown to be upregulated with the method described herein, is known to be a key regulator of synaptic plasticity.

Additional methods for controlling brain activity are described below. As described herein, a stimulus (e.g., visual and/or auditory sensory stimulus) can be delivered to a subject. In some implementations, the stimulus is optionally a sensory flicker stimulus. The sensory flicker stimulus (e.g., 40 Hz flicker stimulus) can trigger intracellular signaling (e.g., MAPK, mitogen-activated protein kinase, and NFκB, nuclear factor kappa-light-chain-enhancer of activated B cells, pathways) that controls the expression of genes responsible for many brain functions including synaptic plasticity, metabolism, proliferation, gene expression, differentiation, mitosis, cell survival, and/or apoptosis. The sensory flicker stimulus modulates these pathways within neurons, causing neuronal expression of key secreted factors, such as cytokines, which affect all other cell types in the brain, including endothelial cells, oligodendrocytes, astrocytes, and microglia. Thus, sensory flicker stimulation drives neural activity to control MAPK and NFκB pathways, ultimately driving changes in a diversity of functions implicated in neurodegenerative and neurological diseases, including, but not limited to, lysosomal dysfunction, myelination, activation and glucose metabolic regulation of astrocytes, blood-brain barrier function, cerebrovascular growth, and lipid and metal metabolism. Given the specific cytokines expressed in response to sensory flicker stimuli (e.g., VEGF, MIG), cells outside of the central nervous system, for example peripheral immune cell infiltration, can be controlled.

Figure 17A:
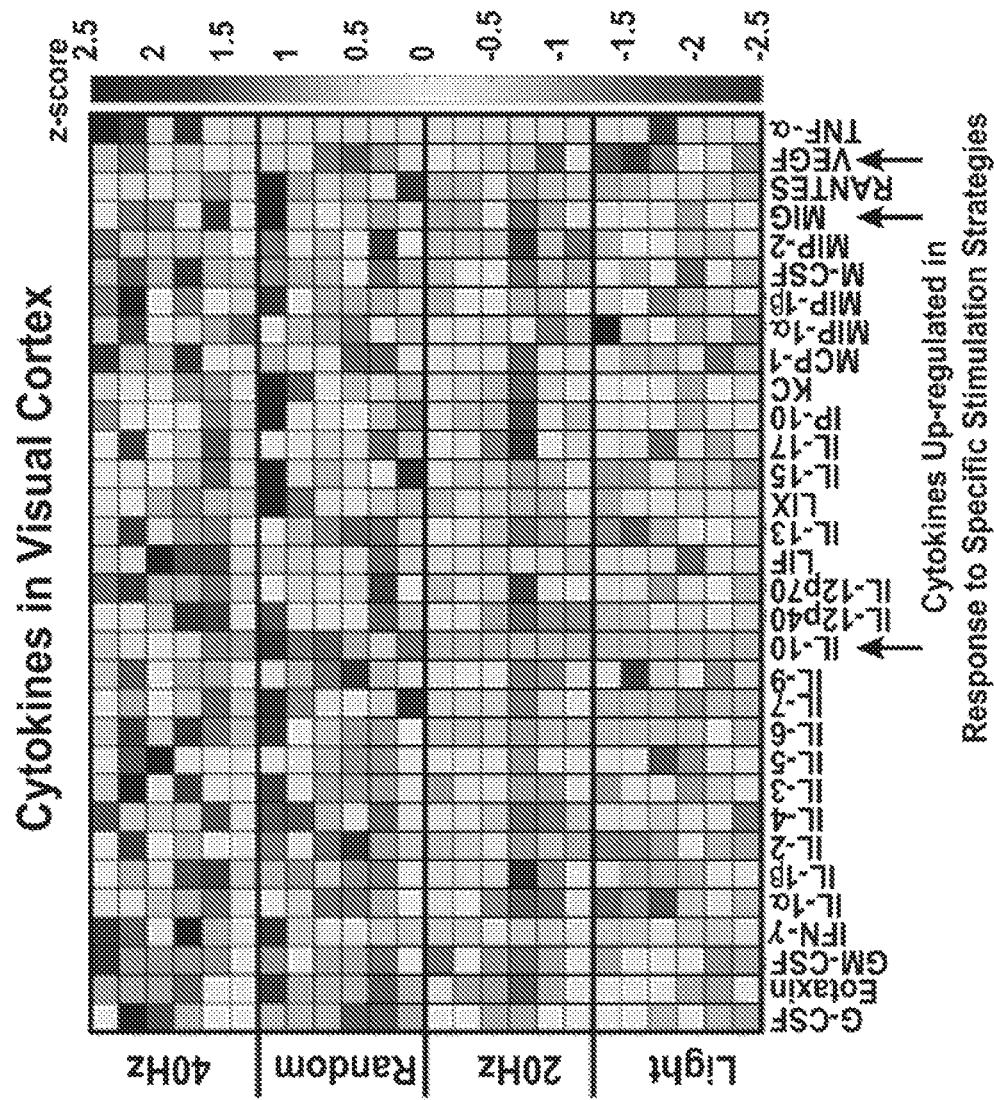
FIGS. 17A and 17B show visual flicker stimulates cytokine expression in visual cortex.
Figure 17B:
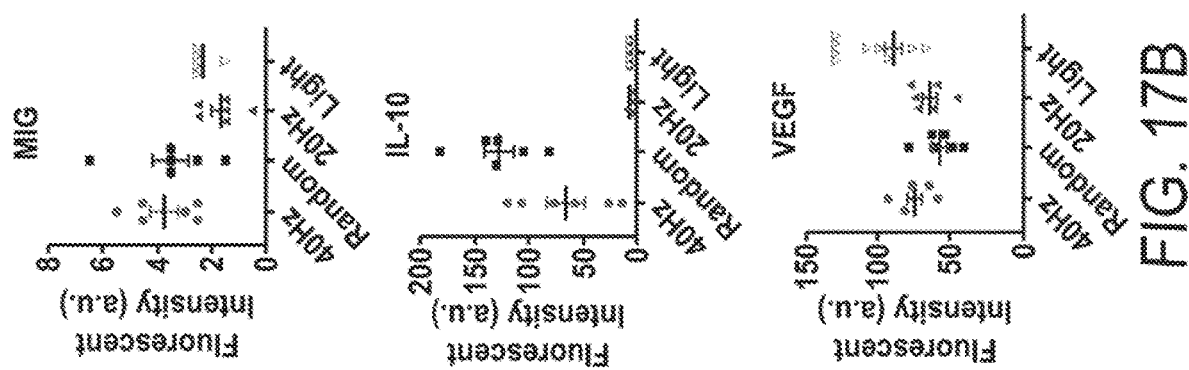
Figure 27:
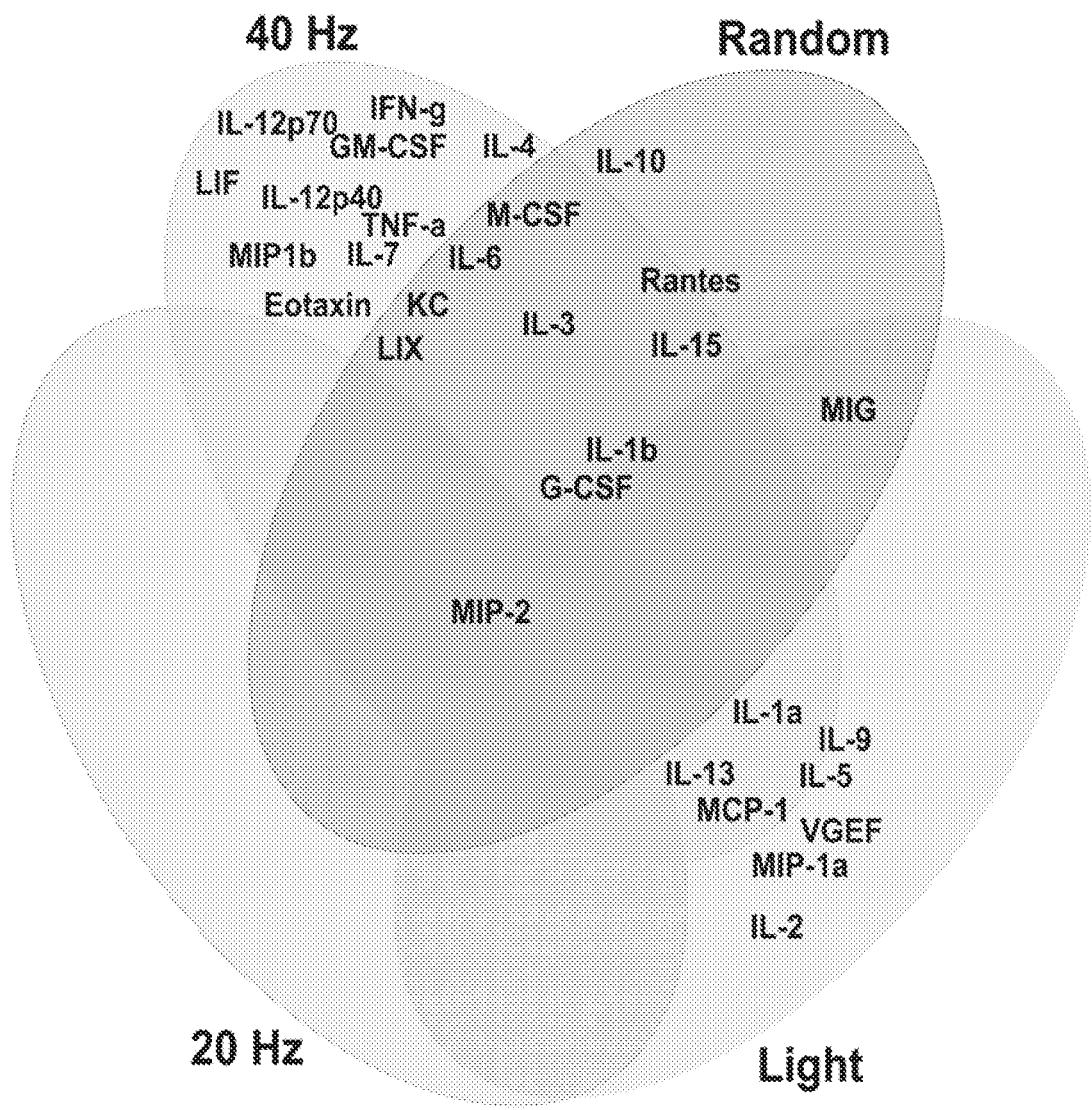
FIG. 27 illustrates a Venn diagram showing which cytokines are elevated in which conditions, illustrating how different stimulation frequencies increase or decrease specific cytokines or groups of cytokines. Cytokines listed in a particular part of the Venn diagram, mean those cytokines are elevated in those conditions. Using a Venn diagram like this (or a stimulation to phosphoprotein or stimulation to gene map), a therapy would be targeted to specific condition or patient based on which cytokines would be most desirable to increase.

In some implementations described below, different stimulation parameters (e.g., stimulation frequency and/or stimulation duration) are used to differentially effect expression of proteins (e.g., cytokines, chemokines, growth factors, etc.) regulated by these pathways. In other words, parameters such as duration and/or frequency of stimulation can be used to tune the effects of stimulation. For example, 5 minutes of 40 Hz flicker leads to increases in ERK phosphorylation, a protein in the MAPK pathway, while 30 or more minutes of 40 Hz flicker leads to decreases in ERK phosphorylation. Additionally, 1 hour of 20 Hz flicker leads to lowered cytokine levels, while 40 Hz flicker leads to elevated cytokine levels, and constant light stimulation results in cytokine levels in between the two. These are provided only as two examples. Other example differential effects are shown in FIGS. 17 and 27.

In some implementations, these relationships between stimulation parameters (e.g., duration, frequency, etc.) and protein expression can be used to individualize therapies for specific patients or disease conditions. This relationship can be called a stimulation-to-gene expression (StG) Map. Stimulation can thus be used to produce differing effects across individuals, depending on need. For example, in one disease or individual, it may be desirable to reduce TNF-alpha (a specific cytokine) while increasing RANTES (a different cytokine). To achieve this effect, one can look up the specific stimulation conditions that produce these effects and then apply to them to the patient and read-out the effects in the cerebral spinal fluid. The stimulation parameters can then be fine-tuned based on the patients' response or individual variation over time.

An example method for controlling brain activity in a subject is described. According to this method, the stimulus is delivered for a short duration. In a first step, a stimulus is delivered to the subject, where the stimulus induces neural activity in the subject's brain and modulates expression of at least one soluble mediator of cellular activity within the subject. As described herein, the at least one soluble mediator of cellular activity within the subject can be a cytokine, chemokine, or growth factor. Additionally, the stimulus can be delivered to the subject for less than one hour. Optionally, the stimulus can be delivered to the subject for less than about 30 minutes (for example, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 minutes). Optionally, the stimulus can be delivered to the subject for less than about 10 minutes (for example, 10, 9, 8, 7, 6, 5, 4, 3, 2, 1 minutes). Optionally, the stimulus can be delivered to the subject for less than about 5 minutes (for example, 5, 4, 3, 2, 1 minutes). Conventionally, techniques to manipulate immune function take greater than 1 hour to see an effect. In contrast, and as described herein, MAPK and NFκB pathways were found to turn ON/OFF quickly (e.g., up at 5 min and decreasing at 10 min) using the methods described herein. Additionally, transient immune response is often desirable, which is in contrast to chronic immune response which may be undesirable or maladaptive. Further, sustained pathway activation, which occurs using conventional techniques, can lead to negative regulation via feedback, regulated by gene expression and other mechanisms. Thus, the short duration stimulation techniques described herein can lead to pathway activation that enables the ability to "precisely" regulate expression of diverse genes. Accordingly, the methods described herein have advantages including, but not limited to, those listed above as compared to conventional techniques for controlling brain activity.

In some implementations, the stimulus can be a non-invasive stimulus. In some implementations, the stimulus can be transcranial electrical stimulation or transcranial magnetic stimulation. In other implementations, the stimulus can be a visual stimulus, an auditory stimulus, or combinations thereof. As described above, a visual stimulus can be produced with light (e.g., white light), and an auditory stimulus can be produced with sound. Optionally, the stimulus can be sensory flicker used to induce gamma activity. For example, the stimulus can be a 20 Hz sensory flicker stimulus. Alternatively, the stimulus can be a 40 Hz sensory flicker stimulus. Visual flicker stimulus can be produced by flashing a light at a desired frequency (e.g., 12.5 millisecond (ms) ON every 25 ms for 40 Hz, 25 ms ON every 50 ms for 20 Hz). This disclosure contemplates that duty cycles between 4-50% can be used for the visual flicker stimulus. It should be understood that the color and/or parameters (e.g., frequency, period, duty cycle, etc.) of the visual flicker stimulus are provided only as examples and can have other characteristics/values while still inducing gamma activity. Auditory flicker stimulus can be produced by sounding a 1 ms long 10 kHz tone every 25 ms. It should be understood that the tonal frequency and/or parameters (e.g., frequency, period, duty cycle, etc.) of the auditory flicker stimulus are provided only as examples and can have other characteristics/values while still inducing gamma activity. In some implementations, the stimulus can be a random sensory flicker stimulus. A random sensory flicker can be achieved with variable inter-pulse (e.g., light or sound) intervals, e.g., varying the time between when the light or sound pulse goes OFF before the next light or sound pulse goes ON. Alternatively, the stimulus can be a constant sensory stimulus (as opposed to a flicker stimulus), e.g., a constant light stimulus.

By delivering the stimulus, brain activity can be induced in at least one of the sensory cortices. Alternatively or additionally, brain activity can be induced in a deep brain region such as at least one of the hippocampus, medial temporal lobes, or frontal lobes. Optionally, in some implementations, the stimulus drives gamma neural activity in the subject's brain.

Optionally, in a next step, a disease or condition in the subject is treated using the stimulus delivered to the subject. In some implementations, a disease, injury, infection, or normal aging in the subject's brain is treated. In other implementations, a neurodegenerative disease is treated. Neurodegenerative disease can include, but are not limited to, Alzheimer's disease, Parkinson's disease, dementia, frontotemporal dementia, vascular dementia, amyotrophic lateral sclerosis (ALS), and multiple sclerosis (MS). In yet other implementations, a condition in the subject is treated by modulating the at least one of immunomodulatory signaling or cell survival signaling within the subject. The condition can include, but is not limited to, epilepsy, schizophrenia, autism, traumatic brain injury (TBI), bipolar disorder, stroke, or depression.

In one aspect, it is understood and herein contemplated that the stimulus can be delivered for less than one hour in the disclosed methods. In one aspect, the less than one hour stimulus can be delivered as a single exposure or in 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 150 or more dosed exposures per day. Additionally, it is understood and herein contemplated that stimulus treatment can be administered at least once every 6, 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months. In one aspect, the treatment can be administered a single time or as needed to treat the neurological disease or condition. Thus, in one aspect, the treatment can occur for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 60 days, 3, 4, 5, 6, 7, 8, 9, 10, 11, 12, 13, 14, 15, 16, 17, 18, 19, 20, 21, 22, 23, 24 months, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or more years. In one aspect, the treatment continues for the remainder of the life of the subject.

Another example method for controlling brain activity in a subject is described. According to this method, the relationships between stimulation parameters and protein expression are used to individualize therapies for specific patients and/or disease conditions. In a first step, at least one soluble mediator of cellular activity within the subject (e.g., a cytokine, chemokine, or growth factor) to modulate is selected. This can be accomplished, for example, by selecting a protein relevant to treatment of the specific subject and/or disease.

In a next step, a type of stimulus that modulates the selected at least one soluble mediator of cellular activity can be selected. The stimulus parameters (e.g., type, frequency, durations, etc.) can be varied or selected depending on which soluble mediator of cellular activity is to be modulated. For example, one of a 20 Hz sensory flicker stimulus, a 40 Hz sensory flicker stimulus, a random sensory flicker stimulus, or a constant sensory stimulus can be selected. The stimulus that modulates the selected soluble mediator of cellular activity can be chosen, for example, by looking up the specific stimulation conditions that produce the desired effects. In some implementations, different stimulation frequencies produce different effects. In some implementations, different stimulation durations produce different effects in ways that are not a simple dose dependent curve (e.g., longer stimulation=bigger effect), For example MAPK is up at 5 minutes of 40 Hz and down at 30 min, whereas cytokines are up at 1 hr of 40 Hz. Other example differential effects of different stimulation parameters are shown in FIGS. 17 and 27. Example 20 Hz sensory flicker stimulus, 40 Hz sensory flicker stimulus, random sensory flicker stimulus, and constant sensory stimulus are described above. It should be understood that the frequencies (e.g., 20 Hz and 40 Hz) of the sensory flicker provided above are only provided as examples and that other frequencies may be used with the techniques described herein.

The 20 Hz sensory flicker stimulus can modulate soluble mediators of cellular activity. In one aspect, a 20 Hz sensory flicker stimulus can modulate Interleukin-4 (IL-4), Interleukin-7 (IL-7), Granulocyte-macrophage colony-stimulating factor (GM-CSF), Interleukin-12 p70 (IL-12p70), Interleukin-12 p40 (IL-12p40), Interferon-γ (IFN-γ), LIF, Tumor necrosis factor-α (TNF-α), Macrophage inflammatory protein 1β (MIP-1β), Eotaxin, Interleukin-10 (IL-10), vascular endothelial growth factor (VEGF), Interleukin-2 (IL-2), Interleukin-5 (IL-5), Interleukin-9 (IL-9), Macrophage inflammatory protein 1α (MIP-1α), monokine induced by gamma interferon (MIG), growth-regulated oncogene-α (GRO-α), LIX (also known as CXCL5), granulocyte colony-stimulating factor (G-CSF), Interleukin-1β (IL-1β), Interleukin-3 (IL-3), Interleukin-6 (IL-6), Interleukin-15 (IL-15), Regulated upon Activation, Normal T cell Expressed, and Secreted (RANTES), macrophage colony-stimulating factor (M-CSF), Interleukin-13 (IL-13), monocyte chemoattractant protein 1 (MCP-1), and/or Interleukin-1α (IL-1α). The 40 Hz sensory flicker stimulus can modulate Interleukin-4 (IL-4), Interleukin-7 (IL-7), Granulocyte-macrophage colony-stimulating factor (GM-CSF), Interleukin-12 p70 (IL-12p70), Interleukin-12 p40 (IL-12p40), Interferon-γ (IFN-γ), LIF, Tumor necrosis factor-α (TNF-α), Macrophage inflammatory protein 1β (MIP-1β), and/or Eotaxin. The random sensory flicker stimulus can modulate IL-10. The constant sensory stimulus can modulate vascular endothelial growth factor (VEGF), Interleukin-2 (IL-2), Interleukin-5 (IL-5), Interleukin-9 (IL-9), and/or Macrophage inflammatory protein 1α (MIP-1α). In one aspect, the stimulus can be a 40 Hz sensory flicker stimulus or a random sensory flicker. When the stimulus is a 40 Hz sensory flicker stimulus or a random sensory flicker, the stimulus can modulate oncogene-α (GRO-α), LIX (CXCL5), granulocyte colony-stimulating factor (G-CSF), Interleukin-1β (IL-1β), Interleukin-3 (IL-3), Interleukin-6 (IL-6), Interleukin-15 (IL-15), Regulated upon Activation, Normal T cell Expressed, and Secreted (RANTES), and/or macrophage colony-stimulating factor (M-CSF). In another aspect, the stimulus can be a 40 Hz sensory flicker stimulus or a constant sensory stimulus. When the stimulus is a 40 Hz sensory flicker stimulus or a constant sensory stimulus, the stimulus can can modulate Interleukin-13 (IL-13), monocyte chemoattractant protein 1 (MCP-1), and/or Interleukin-1α (IL-1α).

In a next step, the selected sensory stimulus is delivered to the subject, where the sensory stimulus induces neural activity in the subject's brain.

Optionally, in a next step, a disease or condition in the subject is treated using the stimulus delivered to the subject. In some implementations, a disease, injury, infection, or normal aging in the subject's brain is treated. In other implementations, a neurodegenerative disease is treated. Neurodegenerative disease can include, but are not limited to, Alzheimer's disease, Parkinson's disease, dementia, frontotemporal dementia, vascular dementia, amyotrophic lateral sclerosis (ALS), and multiple sclerosis (MS). In yet other implementations, a condition in the subject is treated by modulating the at least one of immunomodulatory signaling or cell survival signaling within the subject. The condition can include, but is not limited to, epilepsy, schizophrenia, autism, traumatic brain injury (TBI), bipolar disorder, stroke, or depression.

EXAMPLES

Example 1

The examples below provide insight into the mechanisms by which gamma oscillations modulate brain immune activity in Alzheimer's disease. The data show that neural activity in the form of gamma oscillations are able to promote neural immune activity by rapidly stimulating signaling within the MAPK and NFκB pathways. The activity stimulated induces expression of multiple cytokines, chemokines, and growth factors, which are known to recruit microglia as well as control diverse beneficial cellular functions, including survival, proliferation, differentiation, plasticity, and neurogenesis, among others.

Methods.

A protocol was developed to induce gamma oscillations in multiple parts of the mouse brain by presenting visual or auditory 40 Hz sensory flicker to mice. In addition, an integrated systems analysis was used to profile intracellular signaling pathways and identify candidate signals and pathways that are closely correlated with gamma induction. This interdisciplinary approach provides an unprecedented opportunity to characterize the complex relationship between gamma activity, neural function, and immune activity. Given reported deficits in gamma activity in patients with AD, this work contributes an important new understanding of the implications of this loss in AD.

Figure 5:
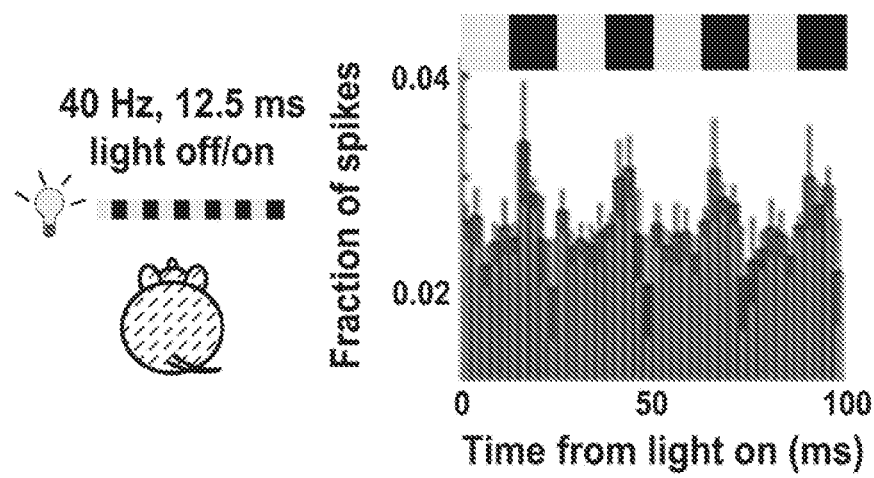
FIG. 5 is a diagram illustrating gamma visual flicker transforming microglia and reducing amyloid beta in visual cortex.

Auditory Flicker and Combined Auditory and Visual Flicker Drives Gamma in Hippocampus It was recently discovered that driving neural activity at gamma frequency (e.g., about 40 Hz) morphologically transformed microglia and mobilized them to increase engulfment of amyloid beta, a protein whose aggregation is thought to initiate neurotoxic events in AD (FIG. 5). Driving 40 Hz neural activity for 1 hour resulted in a 40% reduction in amyloid beta. Initially invasive optogenetics was used to drive gamma. Invasive optogenetics requires virus infection and fiber implants to drive neural activity with laser light. A method to drive gamma non-invasively was then developed: flickering lights at 40 Hz. Flickering lights at gamma frequencies drives strong gamma oscillations in visual cortex, however the effects are weaker in hippocampus (HPC), the brain region essential for spatial and experiential memory.

Figure 6A:
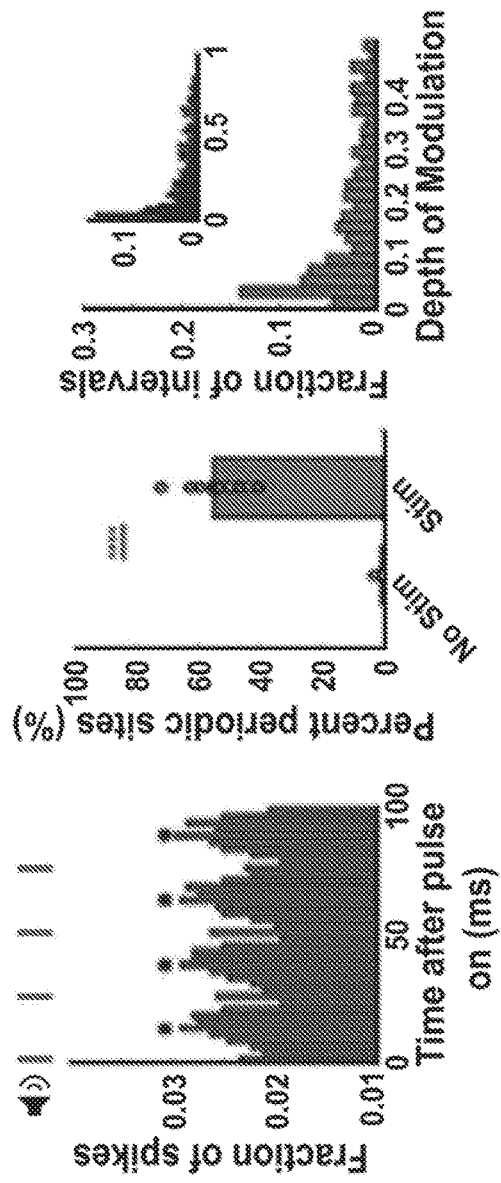
FIGS. 6A-6B are diagrams illustrating sensory flicker entraining neural activity in the hippocampus (HPC) of the brain.
Figure 6B:
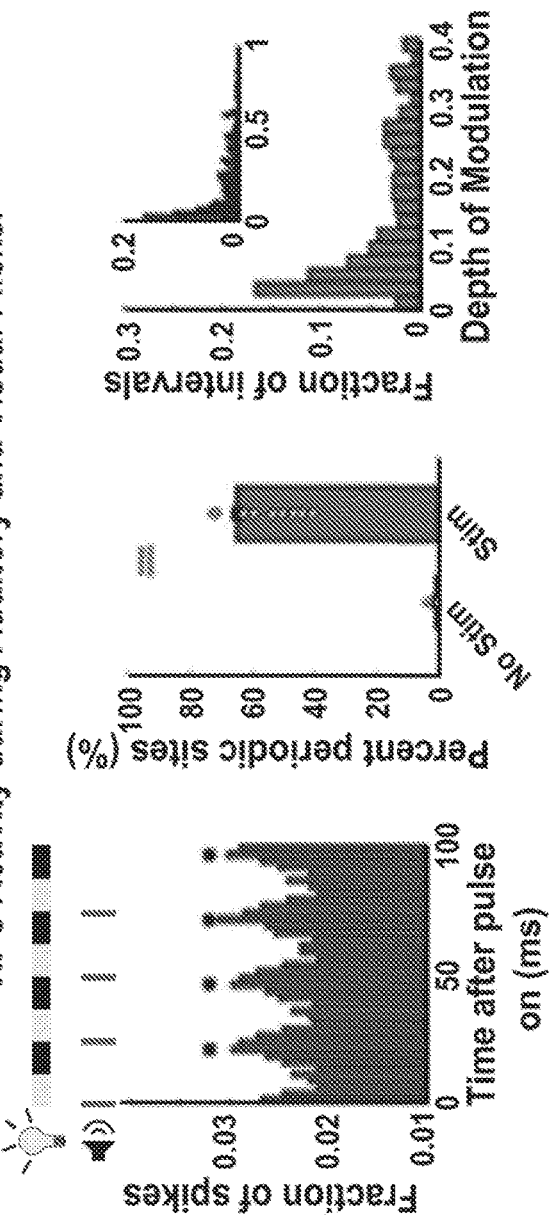

Auditory sensory flicker at 40 Hz also drives 40 Hz neural activity in HPC (FIG. 6A-6B). This discovery makes it possible to study the effects of driving gamma non-invasively on hippocampal neural codes essential for learning and memory. Electrophysiological recordings were performed using 32-channel silicone probes in hippocampal CA1 subregion (HPC) of wild-type (C57BL6J) mice running or resting on a spherical treadmill. While neural activity was recorded, animals were presented with interleaved periods of (1) quiet darkness, (2) tones that turned on and off at 40 Hz (1 ms long 10 kHz tones played every 25 ms, referred to below as auditory flicker stimuli), and (3) tones and lights that turned on and off at 40 Hz (1 ms long 10 kHz tones and 12.5 ms long white lights on every 25 ms, referred to below as multimodal flicker stimuli). The visual flicker, auditory flicker, and multimodal flicker stimuli are also sometimes referred to herein as visual flicker, auditory flicker, and combined visual and auditory flicker, respectively. Additionally, these stimuli are examples of sensory flicker as described herein. In response to sensory stimulation, spiking increased and decreased periodically with the tones, thus neural activity entrained to 40 Hz during 40 Hz auditory or multimodal flicker stimulation (FIG. 6A-6B). The interval between peaks in spiking rate during 40 Hz auditory flicker was around 25 ms (equivalent to 40 Hz) for the majority of recording sites. During auditory stimulation, on average 55% of recording sites had periodic spiking responses and during auditory plus visual stimulation, 61% of CA1 recording sites had periodic spiking compared to 1% of recording sites during baseline periods (FIG. 6A-6B). Thus, 40 Hz auditory or auditory and visual flicker stimulation induced robust 40 Hz entrainment in CAL Furthermore, it was found that exposing animals to auditory flicker or combined auditory and visual flicker for 1 hr/day for 7 days recruits microglia and reduces amyloid beta load in HPC. The combined auditory and visual flicker method to drive gamma non-invasively was used below to identify the mechanisms by which gamma modulates microglial activity and neural coding, and also show how gamma treatment may be effective to treat AD mice.

Figure 7A:
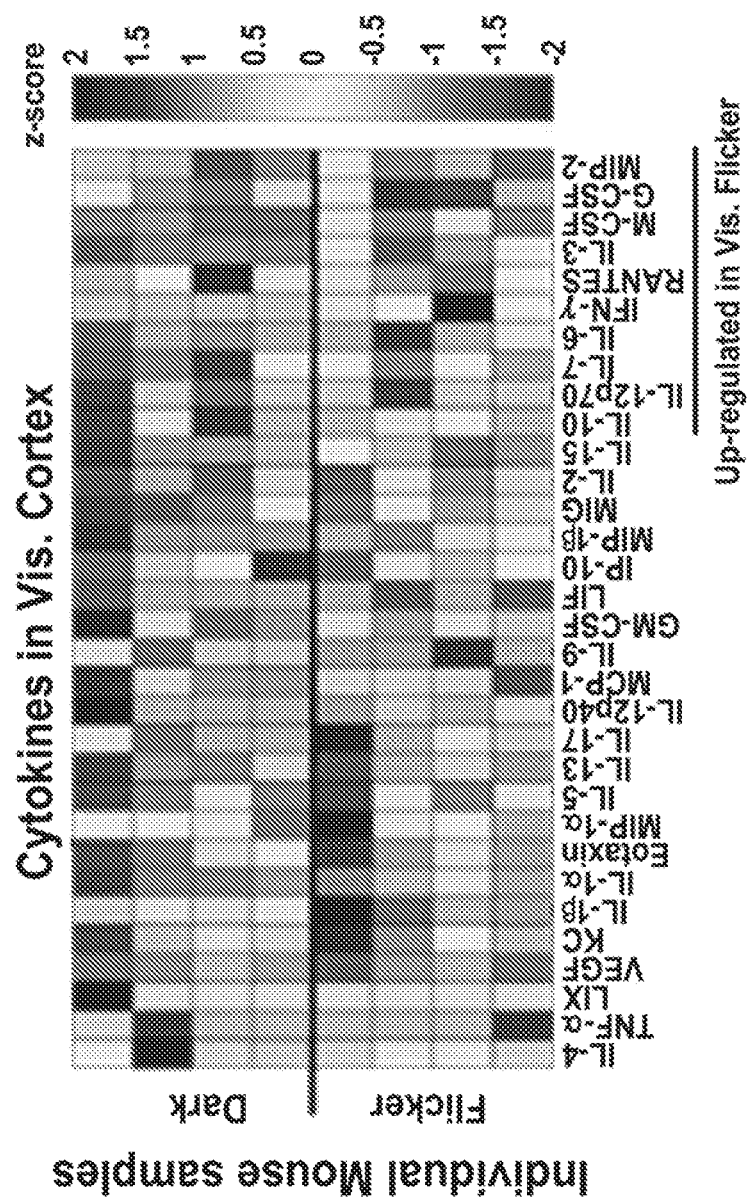
FIGS. 7A-7C are diagrams illustrating that cytokine protein expression is up-regulated after exposure of mice to sensory visual flicker.
Figures 7B, 7C:
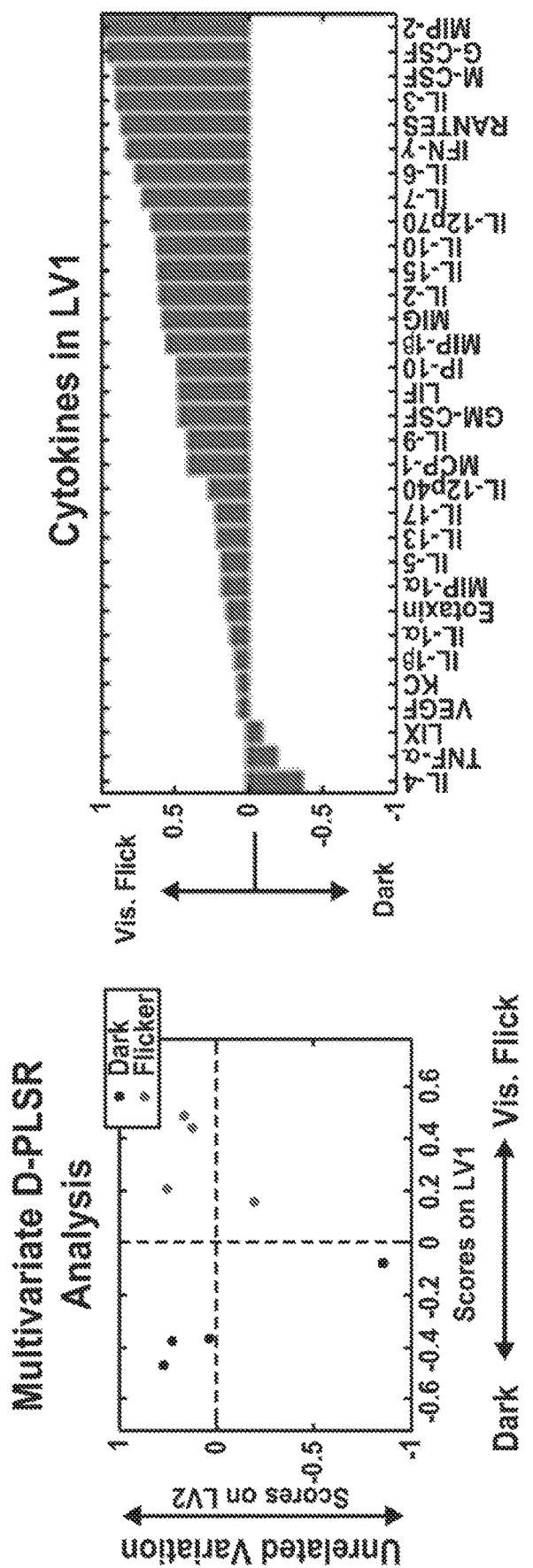

Sensory Flicker Up-Regulates Expression of Pro-Inflammatory Cytokines in the Visual Cortex To identify immune signaling activated by flicker, a multiplexed immunoassay (e.g., a multiplexed assay systems from LUMINEX CORP. of Austin, Texas and EMD MILLIPORE) was used to quantify expression of 32 cytokines and growth factor proteins within the visual cortex after mice were presented with visual flicker for either 30 or 60 min. The analysis revealed a subtle increase in certain cytokines by 30 minutes (data not shown), and a pronounced increased in cytokines involved in microglial recruitment and activation by 60 min (FIG. 7A). To account for the multidimensional nature of the data, a discriminant partial least squares regression (D-PLSR) was used as an unbiased strategy to identify cytokines that were most strongly correlated with flicker. D-PLSR is similar to a principal component analysis, but identifies maximal differences between groups. The analysis identified a profile of cytokines, LV1, which best distinguished flicker from dark mice (FIG. 7B). The axis, LV1, consisted of a profile of cytokines (FIG. 7C) that correlated with flicker or dark animals in the visual cortex. Importantly, top correlates with flicker were MIP-2, IL-3, RANTES, and IFN-γ, which are involved in microglial recruitment and activation/polarization. These data suggest that extracellular cytokine/chemokine signaling may be responsible for microglial activity in response to flicker.

Figure 8A:
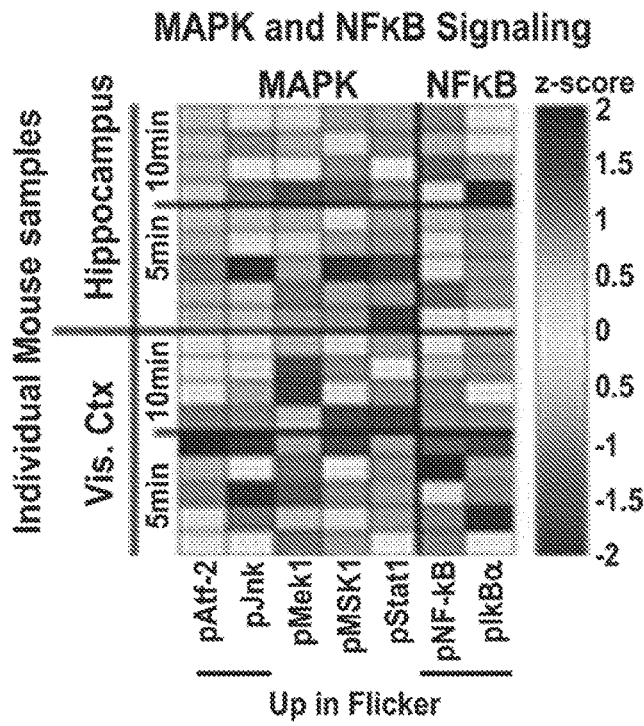
FIGS. 8A-8C are diagrams illustrating pro-inflammatory intra cellular signaling up-regulation after exposure of mice to sensory visual flicker.
Figure 8B:
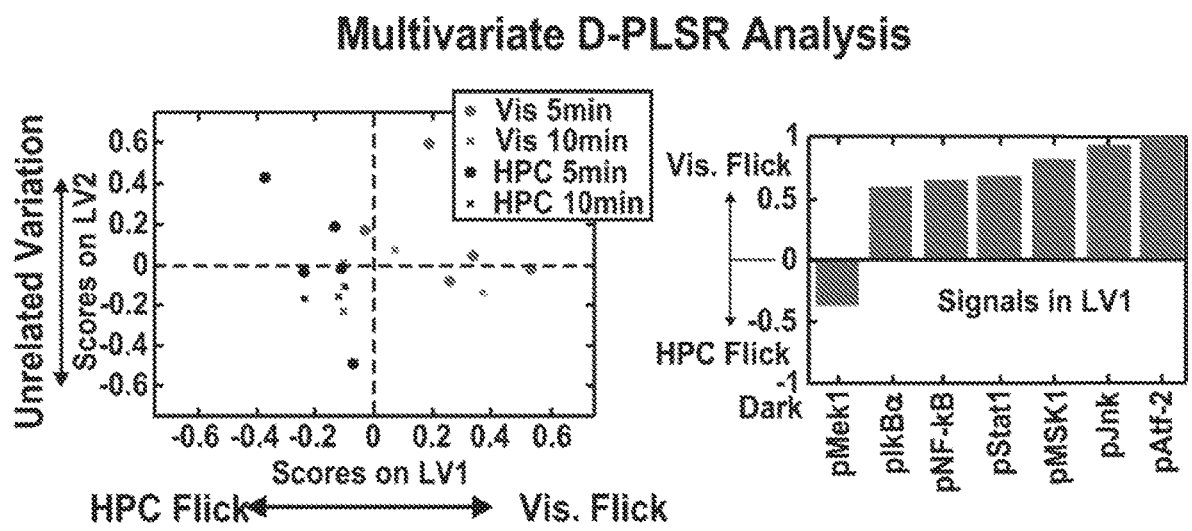
Figure 8C:
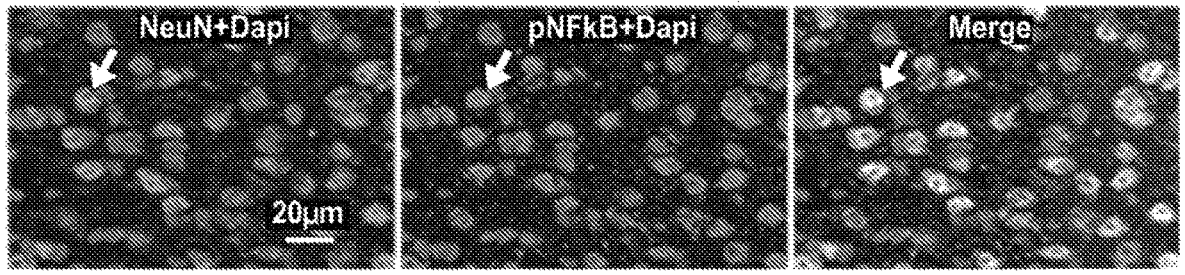

Sensory Flicker Up-Regulates Intracellular MAPK and NFκB Signaling in the Visual Cortex Immune activity is centrally regulated by intracellular signaling within several canonical kinase pathways, including the mitogen activated protein kinase (MAPK) and nuclear factor kappa-light-chain-enhancer of activated B cells (NFκB) pathways. These pathways regulate downstream expression of numerous factors, including cytokines, which are involved in recruitment and activation of microglia. Moreover, these pathways regulate expression and activity of immediate early genes, including Arc and C-Fos that regulate neural activity. These pathways also regulate and promote survival signaling within neurons and other cell types. Therefore, they represent a natural bridge between electrical gamma activity and broader immune responses like microglial and astrocyte recruitment and activation, and neuronal health and survival. Importantly cellular response phenotypes, such as microglial activation, occur on a much longer time scale (~hours-days) than intracellular signaling (~minutes).[8] Thus, the visual cortex was analyzed at a short time point after either 5 or 10 min of visual flicker. Mice were exposed to flicker, then immediately euthanized, with brain tissues collected and lysed within 3 minutes of euthanasia. Luminex analysis was again used, but this time to quantify 5 phospho-proteins within the MAPK pathway and 2 phospho-proteins within the NFκB pathway (FIG. 8A). Using a D-PLSR analysis, 5 min flicker samples in the visual cortex were separated from the HPC flicker samples (FIG. 8B), along an axis of phospho-proteins, LV1. In this case, LV1 consisted of a profile of phospho-proteins, including Atf-2, Jnk, IκB, and NFκB, which were up-regulated at the 5 min time point in the visual cortex, but not the hippocampus. Moreover, this increase in signaling was lost in the visual cortex by the 10 min time point (FIG. 8B). Interestingly, all of the up-regulated signals are relatively downstream in the pathway, suggesting that up-stream phosphorylation may occur at an earlier time point. Additionally, these pathways were not found to be up-regulated at 30 min or 60 min times points (not shown), consistent with the known transience of kinase signaling.[8,9] Finally, since the cytokine data suggest that extracellular cytokine signaling may be involved in microglial activity post-gamma, immunohistochemistry (IHC) was next used to determine which cell type NFκB signaling was occurring in. By co-labeling, it was found that NFκB was co-localized with the neuronal marker NeuN (FIG. 8C). Co-labeling of NFκB with Iba1+ microglia was not identified (data not shown). Combined with the cytokine data, these signaling data suggest gamma oscillations induce intraneuronal signaling, which stimulates downstream expression of immunomodulatory factors, such as cytokines, and stimulates microglial activity.

Gamma Deficits are Found in Alzheimer's Disease Mice

Deficits in gamma oscillations have been found in mouse models of Alzheimer's, including in the transgenic 5xFAD amyloid mouse model. In particular, deficits in the strength of gamma oscillations, as well as how well spikes are modulated by gamma oscillations, have been identified during sharp wave ripples (SWRs), activity that is essential for spatial learning and memory in healthy mice. These deficits begin early in the disease prior to behavior deficits (first detected at 3-months-old). Furthermore, it has been found that driving gamma activity significantly reduced amyloid beta levels and recruited microglia to increase engulfment of amyloid (FIG. 5). These results suggest that deficits in neural activity may not only lead to learning and memory deficits but also contribute to the molecular and cellular pathology of AD. The deficits found in 5xFAD mice are strikingly similar to those found in APOE4 mice, even though these animal models have very different underlying pathology. Furthermore, the deficits found in 5xFAD mice have some similarities to deficits reported in another mouse model, hAPP, and in humans with AD. These results show that SWRs and gamma are altered in multiple AD models suggesting that the cells and circuits that produce this activity may be especially susceptible to AD pathology. Thus, the sensory stimulation described herein has the potential to lead to new therapies for Alzheimer's disease, the most common dementia, or other diseases with deficits in rhythmic activity. As a result, the non-invasive methods to drive specific patterns of rhythmic activity described herein can have wide-ranging clinical applications to rescue neural activity and impact molecular pathology.

The data demonstrate that 5xFAD Alzheimer's mice suffer reduced gamma activity. Moreover, gamma oscillations have been found to induce intracellular signaling within the MAPK and NFκB pathways within minutes of stimulation, enhanced expression of numerous immunomodulatory cytokines within an hour, changes in microglial activation after an hour, and reduction of amyloid load over the course of a week.

Intracellular MAPK and NFκB Signaling Pathways Mediate the Effects of Gamma Activity on Microglial Phenotype The data suggests that flicker-induced gamma oscillations stimulate a rapid (<5 min) up-regulation of signaling within the MAPK and NFκB pathways (FIG. 8A-8C), followed by increased expression of pro-inflammatory cytokines (FIG. 7A-7C). Further, published data show that gamma promotes microglial activity and Aβ clearance in 5xFAD mice over a week.[1] Given the known pro-inflammatory roles for these pathways in the periphery and the brain, the temporal relationship in these data suggest that MAPK and NFκB pathways are regulators of gamma-induced neural immune activity (e.g., see FIG. 4).

Importantly, the 5xFAD mouse model, and patients with Alzheimer's disease, already possess a neuroinflammatory microenvironment, consisting of both Iba1+ activated microglia with thickened processes, numerous pro-inflammatory cytokines, reactive oxygen species, among others. Moreover, the chronic neuroinflammatory environment is now thought to promote pathogenesis. Nevertheless, the data suggests that gamma flicker induces immunomodulatory signaling and promotes microglial activity and Aβ clearance (FIG. 5). This data and other work suggests immunomodulatory activity cannot simply be classified as pro-versus anti-inflammatory or active versus passive. Both the AD microenvironment and flicker stimulate microglial activity, but potentially in different ways or into different functional phenotypes.

As discussed above, classical microglial activation markers cannot fully elucidate the effects of signaling inhibition on the neuroinflammatory microenvironment. Thus, protein quantification of 32 cytokine/chemokines via Luminex analysis can be relied upon.[6] To gain a broad view of microglia activity, both classical markers, such as Iba1 via immunohistochemistry (IHC) together with a broad RNAseq-based profiling of isolated microglia can be used.

A temporal analysis of immunomodulatory signaling and microglial activity in response to flicker is described below. Wild-type (WT) and 5xFAD littermate mice can be exposed to 40 Hz auditory and audio/visual flicker (40 Hz), random sensory flicker, or no flicker (Sham) for 2 hours, 1 hr/day for 1 week, or 1 hr/day for 1 month. Random and no flicker Sham groups can serve as controls. During random flicker, lights and sound can be presented at a randomized interval that averages 40 Hz. Random stimulation serves as a control because gamma frequency neural activity is not increased but the same number of stimuli are delivered on average over the exposure period.[1] Animals can be brought to the lab, sit in a quiet room for 1 hour, and then placed in a clean empty exposure box and exposed to flicker or no stimulation for the prescribed time. For animals exposed to flicker for multiple days, this procedure can be repeated at the same time each day and then animals can be returned to the animal facility. Following the final flicker exposure, animals can be sacrificed.

This analysis fully characterizes the temporal evolution of gamma flicker-induced immune activity and to determine whether or not there are differences in this activity between healthy WT and 5xFAD diseased mice.

Combined audio/visual flicker can be used on 5xFAD mice and wild-type littermate controls. Response can be assessed at 2 hr, 1 week, and 1 month time points in terms of Luminex protein expresion of 32 immunomodulatoy cytokines, via histologial analysis of microglial and astrocyte activation markers (Iba1 and GFAP), and via RNAseq analysis of microglia flow-sorted from tissues. Within each genotype, experimental groups consisting of 1) 40 Hz, 2) Sham, and 3) Random flicker that does not induce gamma can be used. Based on the differences in Iba1+ microglial cell size[1], the differences found in phospho-Atf2 between flicker stimulated and non-stimulated brain regions (FIGS. 8A-8C), and differences in MIP-2 between flickered and Sham dark animals (FIGS. 7A-7C), a power analysis (two-tailed, 80% power, α=0.05) shows that N=10 mice are needed per experimental group to see differences between the 40 Hz and two control groups. A total of 180 mice are needed to analyze protein differences (10 mice/group×3 groups×3 time points×2 genotpyes).

Quantification and Statistical Analysis of Neuroinflammatory Response

In all mice used for molecular analysis, mice can be anesthetized (isoflurane), euthanized, and the brains removed. The right hemisphere can be fixed in 10% formalin and the left hemisphere can be micro-dissected to isolate the visual cortex, hippocampus, and striatum. Each isolated tissue segment can be lysed in Bio-Plex lysis buffer (Bio-Rad), which is compatible with Luminex analysis and Western blotting. Luminex analysis (Millipore) can be used to quantify a panel of 32 cytokines expressed in each region (FIGS. 7A-7C) and phosphorylation of 7 proteins (FIGS. 8A-8C). Immunohistochemistry (IHC) of right brain slices can be used to quantify Aβ pathology in terms of number of Aβ plaques (6E10 antibody, Biolegend). IHC can also be used to quantify number of Iba-1+ microglia (Waco) and GFAP+(Novus Biologicals) astrocytes in each brain region. Differences in activation markers or individual phosphoproteins or cytokines between groups can be assessed using a one-way ANOVA with Schaffe post-hoc test. Luminex data can also be analyzed using a Discriminant Partial Least Squares Regression (D-PLSR). Statistical testing can be done in a two-dimensional space using an inverse $X^2$ distribution.

Transcriptome Microglial Phenotyping: Cytokine data and astrocyte and microglial marker analysis can give a detailed, but narrow view of inflammatory microglial response to flicker. In order to determine the effects of sensory flicker on microglial phenotype at 2 hr and 1 month, a Percol gradient approach following saline cardiac perfusion can be used, as previously described. Then CD11b+ cells can be sorted by FACS and collected directly into TRIzol (Thermo Fisher) for RNAseq analyses. mRNA can be prepared for analysis using a TruSeq Stranded RNA Library Prep Kit (Illumina) and sequenced in high output mode on Illumina NextSeq 500. Sequencing data can be aligned using TopHat software, and read counts are reported in terms of fragments per kilobase of exon per million (FPKM).

The data can be used to establish a detailed temporal evolution of molecular inflammatory signaling, and glial immune activity in mice exposed to sensory flicker. Moreover, the pathway inhibition studies can be used to show that the MAPK and/or NFκB pathways are responsible for gamma-induced immunomodulation and stimulation. In total, these data can be used to link sensory stimulation, neural activity, and immune cell activity. Moreover, the long term 1 month time point can be used to determine if sustain sensory flicker is able to maintain microglial activity and amyloid clearance in the 5xFAD mouse model.

Since both MAPK and NFκB pathways were up-regulated in response to visual flicker, it is possible that these pathways both contribute to a neuroinflammatory microenvironment. Thus, significant modulation of cytokines, glial activation markers, or the microglial transcriptome may not be found by inhibiting one pathway alone. If this is the case, both pathways can be inhibited simultaneously. Additionally, prior work shows that that targeted inhibition, e.g., within the MAPK pathway can cause responsive signaling within a different pathway, such as PI3K/Akt. Thus, if clear signs of immunomodulation are not seen, Luminex analysis and western blotting can be used to check for activation within other pathways. Finally, since the MAPK and NFκB pathways provide trophic support functions in neurons and other cell types, it is possible that neuronal death, synaptic loss, or other artifacts of daily administration of these drugs may be found. Although this is not likely, if unexplainable pathological artifacts of drugging are found, the drug dose can be reduced or gamma treatment paradigm can be changed to every other day.

The data establishes the molecular mechanisms by neural activity alters inflammatory signaling within the brain. These findings may lead to a rapidly translatable strategy to treat patients with Alzheimer's or other brain disease by exposing them to sensory flicker. The findings may also influence the fields of neuroscience and neuroinflammation/glial activity by demonstrating a causal molecular link between there functions, and providing a new tool to modulate the activities of multiple cell types within the brain via non-invasive stimulation. The inflammatory profiles quantified herein may also be tested in humans via analysis of cerebrospinal fluid and blood. Thus, this study lays the groundwork for clinically viable tests of the effects of prolonged sensory flicker on humans.

Example 2. Non-Invasive Methods to Drive Neural Activity with Millisecond Precision Background: It was recently discovered that flickering lights at gamma frequency (40 Hz) drives gamma frequency neural activity in visual cortex and recruits microglia to engulf pathogenic proteins in mouse models of Alzheimer's disease (AD). This non-invasive sensory stimulation can manipulate neural activity and recruit the brain's immune system to treat neurodegenerative disease. This novel stimulation approach also enables investigations of the causal effects of gamma activity in humans and the hypothesized role of microglia in disease progression. However, it is not yet known how to use sensory stimulation to drive gamma and recruit microglia outside of visual cortex. To treat AD, the most common form of dementia, new forms of sensory stimulation are developed to target deep brain structures like the hippocampus, which are unreachable by existing temporally precise non-invasive stimulation methods. The developed sensory flicker can be used as a tool to entrain neural activity, recruit immune cells, and alter functional connections between neurons in hippocampus, which is essential for learning and memory and is affected early in AD.

While previous sensory stimulation method, flickering lights, drove temporally precise neural activity in visual cortex, it only weakly affected hippocampus. It was found that auditory sensory flicker drives rhythmic neural activity in hippocampus and this approach is further developed. Further characterization determines the types of sensory stimulation (auditory, visual, or both) drive the strongest rhythmic activity in hippocampus and if rhythmic sensory stimulation drives neural cell-types in a manner similar to endogenous oscillatory activity. The data show that auditory stimulation recruits hippocampal microglia, morphologically transforming them to increase engulfment of proteins, a process linked to both clearance of pathogens in disease and to synaptic plasticity in healthy brains. Next, how driving gamma alters microglia, connections between neurons, and neural activity essential for memory in hippocampus is estimated. The data herein address three major unmet needs: (1) non-invasive methods to drive temporally precise neural activity in deep brain structures, (2) non-invasive methods to recruit microglia, immune cells in the brain that play an active role in shaping neural circuits and removing pathogens, and (3) novel approaches to treat AD.

Integrating innovative sensory stimulation and large-scale recordings, the proposed research provides, for the first time, non-invasive methods to drive rhythmic neural activity with millisecond precision and to recruit microglia in deep brain structures. Rhythmic brain activity and microglia are implicated in a range of neurological diseases, from Alzheimer's to epilepsy to schizophrenia and are hypothesized to play a key role in learning and memory. Thus, these results spur novel therapeutic approaches to multiple diseases and galvanize new basic science research with wide-ranging impact.

Figure 9A:
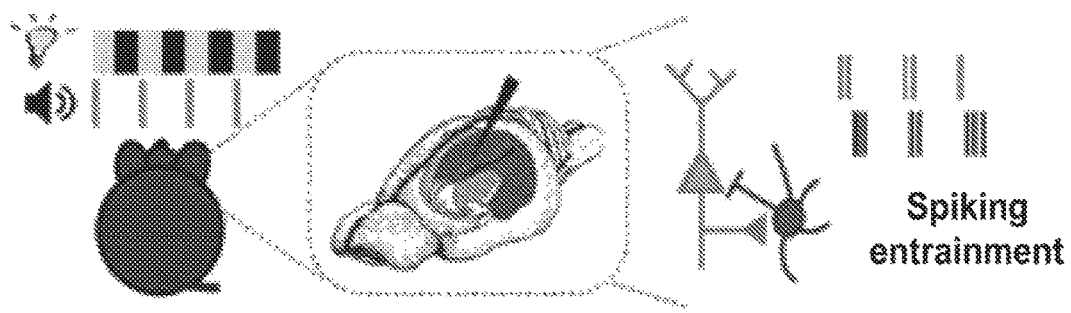
FIGS. 9A and 9B shows how to use sensory flicker stimulation to drive specific frequencies of rhythmic activity in hippocampus.
Figure 9B:
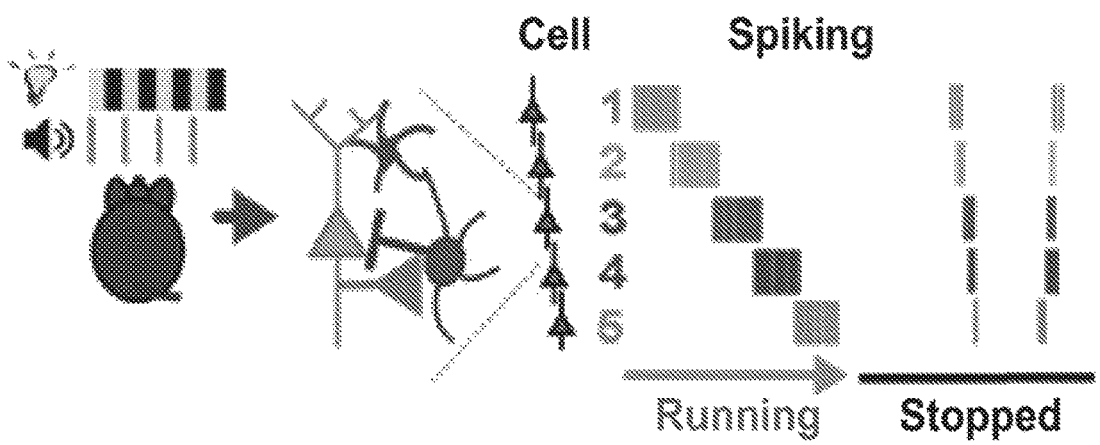
Figure 10A:
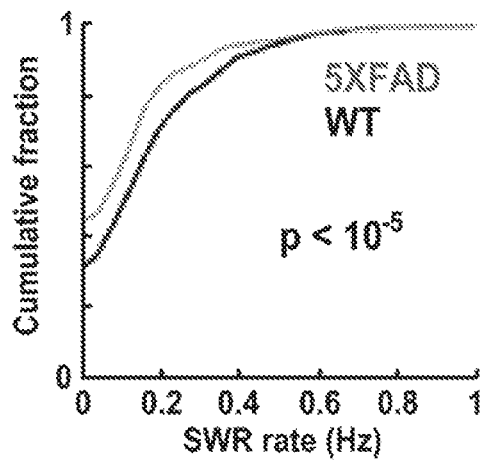
FIGS. 10A-10D show gamma deficits in 5XFAD mouse. Deficits in SWR and gamma activity in 5XFAD mice before evidence of cognitive deficits and the accumulation of plaques (3-months-old). These deficits are strikingly similar to deficits found in gamma during SWRs in APOE4 mouse compared to APOE3 mice, though spikes were not recorded in that study (Gillespie et al. 2016).
Figure 10B:
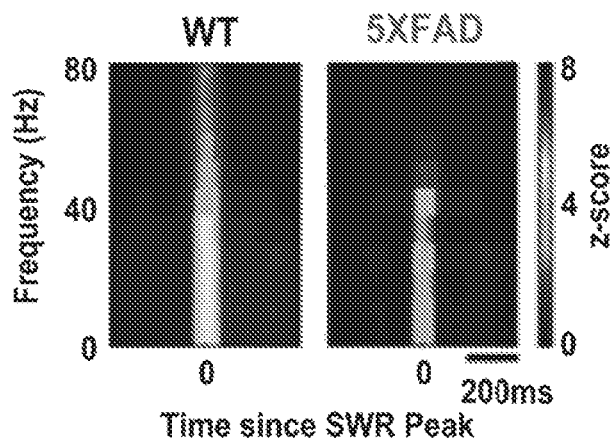
Figure 10C:
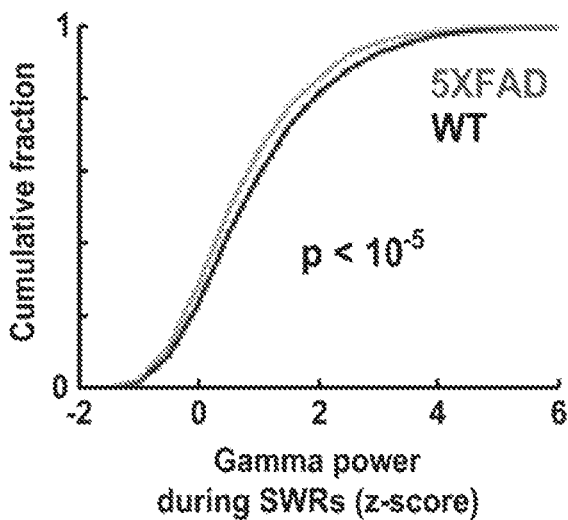
Figure 10D:
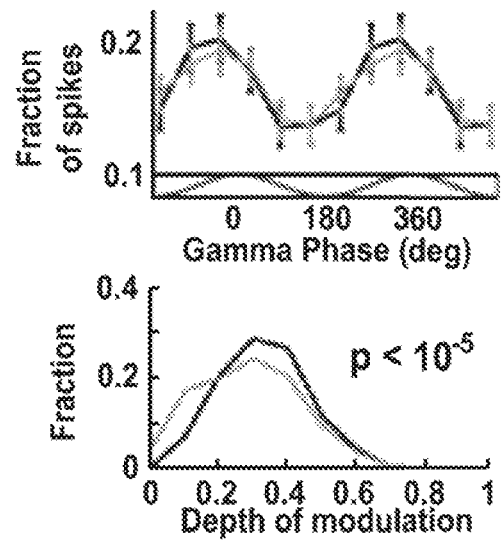

The work shows the development of sensory flicker to entrain neural activity, recruit immune cells, and alter functional connections between neurons in hippocampus (FIG. 9). This research focuses on the hippocampus (HPC) because it is a deep brain structure essential for learning and memory that is affected early in AD. Non-invasive methods to drive rhythmic neural activity in HPC are first developed and optimized. Then, how driving gamma activity non-invasively in HPC affects microglia and neural activity is determined, which is essential for learning and memory, including synaptic efficacy between neurons and neural activity deficits in mouse models of AD. These data result in easy-to-implement tools to drive rhythmic neural activity, recruit immune cells, and alter the strength of synaptic connections in deep brain regions. These data also provide the foundation to test sensory flicker as a therapeutic in humans with AD and other neurological and psychiatric diseases in future studies.

To assess sensory flicker as a method to target deep brain regions, hippocampal activity characterized for three reasons. First, because it is deep in the human brain, the hippocampus is especially hard to target with existing brain stimulation methods like transcranial magnetic stimulation. Thus, approaches that can manipulate hippocampal activity are sorely needed. Second, the HPC is essential for spatial and experiential memory and manipulation of hippocampal activity can enhance learning and memory. To understand the effects of gamma frequency sensory stimulation on neural activity, our research leverages extensive prior research in rodents that has established how hippocampal neural activity underlies spatial learning and memory. Third, the HPC is one of the brain regions affected early in AD, the most common form of dementia, and the HPC is implicated in multiple other diseases like epilepsy, depression, and anxiety disorders. Therefore, new methods to non-invasively manipulate neural activity in HPC leads to new therapies for multiple diseases.

The impact of this method derives from developing easy-to-implement, non-invasive methods to drive temporally precise neural activity, recruit microglia, alter the strength of connections between neurons in deep brain structures. While the initial sensory stimulation method, flickering lights at specific frequencies similar to a high-speed strobe light, drove temporally precise neural activity in visual cortex, it only weakly affected HPC. Thus, a new approach is needed. Therefore, the optimal types of sensory flicker to drive rhythmic neural activity in HPC is established first. Studies show that auditory sensory flicker (tones that turn on and off) drives HPC neural spiking at the same frequency as flicker, called entrainment of neural activity (FIG. 9). Next, the effects of auditory, visual, and combined auditory and visual flicker are tested. Many single cells of multiple types in awake, behaving animals are simultaneously record. Study also determines the form of sensory flicker produces the largest entrainment of neural activity and what flicker frequencies can entrain neural activity. In addition, a portable system to deliver these stimuli in multiple research and clinical environments is developed. Therefore, data show a simple non-invasive tool to entrain temporally precise neural activity in deep brain regions, which can be readily applied in humans.

Many single cells of multiple types in awake, behaving animals are simultaneously record. Study also determines the form of sensory flicker produces the largest entrainment of neural activity and what flicker frequencies can entrain neural activity. In addition, a portable system to deliver these stimuli in multiple research and clinical environments is developed. Therefore, data show a simple non-invasive tool to entrain temporally precise neural activity in deep brain regions, which can be readily applied in humans.

By driving neurons to fire together on short timescales, gamma oscillations are thought to strengthen synaptic connections between neurons and neural codes during a wide range of behaviors. Microglia also play an active role in synaptic plasticity by engulfing synapses. Because gamma sensory stimulation drives neurons to fire together and induces microglia engulfment, study focuses on understanding whether this sensory stimulation changes functional connections between neurons even after flicker is stopped, leading to changes in endogenous gamma activity and neural codes. Furthermore, because driving gamma reduces AD pathogens, it is shown that gamma sensory flicker ameliorates neural activity deficits in AD mice. Thus, this new discovery indicates that 40 Hz sensory flicker drives neural activity non-invasively in HPC to determine the functional effects of driving gamma on microglia, neural connections, and neural codes essential for learning and memory in healthy and AD mice. First, the effect of auditory or combined auditory and visual flicker on microglia is established. Data show that exposing animals to 7 days of auditory flicker for 1 hour per day induces a morphological transformation of microglia and microglia engulfment of amyloid beta in mouse HPC. Second, effects of prolonged 40 Hz flicker on functional connections between neurons in vivo are tested over the course of 2 hours of flicker. Measuring functional connections in vivo allows the examination of changes in synaptic efficacy between neurons in real-time over the course of flicker exposure. To examine functional connections during behavior, how well the firing of one neuron drives another on short timescales (<3 ms) is measured, an assay of monosynaptic strength. Previous data show that HPC neural responses change over about 10 minutes of flicker exposure, which can be due to changes in functional connections as a result of neurons firing together during flicker. It is shown that 40 Hz flicker changes functional connections between fast-spiking interneurons and pyramidal neurons because these cell-types are engaged by gamma rhythms. Finally, how flicker affects gamma during sharp-wave ripples (SWRs) and SWR replay is determined, which are neural codes that are essential for learning and memory. it is shown that prolonged flicker enhances endogenous gamma oscillations during SWRs and, as result, increases replay fidelity. And prolonged sensory flicker rescues SWR deficits as in mouse models of AD. Thus, it is shown that prolonged flicker affects microglia, the strength of synaptic connections, and neural deficits in HPC of AD mouse models.

Clinical Implications of Non-Invasively Driving Rhythmic Brain Activity in Deep Brain Regions The development of new methods to drive brain rhythms non-invasively can to lead to new therapies for human diseases by both driving neural activity that is lacking in disease and recruiting microglia to clear pathogens. Altered rhythmic activity has been observed in many diseases including Alzheimer's disease, Parkinson's disease, schizophrenia, and epilepsy. Deficits in gamma in mouse models of AD and humans with AD have been shown. Deficits in gamma during SWRs in 5XFAD mice is then further determined, a well-established model of AD that carries five familial AD mutations. SWR activity plays a crucial role in spatial learning and memory: if SWRs are disrupted, animals perform significantly worse in spatial memory tasks. Because SWRs repeat sequences of activity many times after learning, they are well suited to drive synaptic plasticity. Gamma oscillations during SWRs coordinate this replay across many neurons. 5XFAD mice had fewer SWRs per time and weaker gamma during SWRs both before (3-months-old) and after (6-months-old) cognitive deficits have been reported in these mice (FIG. 10). Furthermore, it is shown that driving gamma oscillations significantly recruited microglia to increase engulfment of amyloid beta. Microglia have been implicated in multiple neurological diseases, however it has been difficult to establish the causal role of these immune cells in disease because there are currently no methods to recruit microglia without inducing neuronal damage. The methods from current invention to non-invasively recruit microglia allow scientists to test the disease causing or therapeutic potential of manipulating these cells. The non-invasive stimulation methods developed here can ameliorate deficits in neural activity and recruit microglia to clear pathogens forming a foundation for new therapies for Alzheimer's and other diseases. As a result, this new non-invasive method to drive rhythmic activity have widespread clinical uses to rescue neural activity and clear pathology.

Methods and Materials

Methodological: To observe and manipulate neural activity in mice, an innovative approach is used to record neural activity during behavior: brain activity is recorded as mice navigate a virtual reality environment. This paradigm, in which head-fixed mice navigate through a virtual environment (FIG. 11), enables doing several key experiments. First, it allows the examination of neural activity during behavior to characterize the effects of sensory stimulation on neural codes. It is important to note that there are differences between real reality and virtual reality, for example a lack of self-motion cues in virtual reality. However, in real and virtual reality, very similar hippocampal SWRs and gamma activity is found, thus providing strong support for the methods disclosed herein. Second, with this approach, many single cells of different cell-types are recorded to examine the effects of sensory stimulation on particular cell-types and interactions between neurons. Third, this approach is well suited to record from mice, the primary animal model of AD, because when animals are head-fixed recording devices do to not need to be small enough for mice to carry.

Choice of Model System:

The research investigates the effects of sensory flicker stimulation on neural activity, neural connections, and microglia in healthy and AD mice. Neural activity is recorded and microglia is assessed in the 5XFAD mouse model of AD and wild-type mice (WT) littermates at 3 months of age, when SWR deficits are detectable and gamma flicker is found to recruit microglia and reduce amyloid levels. Already, previous data reveal deficits in neural activity in the 5XFAD mouse model that have some similarities to deficits reported in the APOE4 and hAPP mouse models and in humans with AD. Importantly, gamma and SWRs and the circuits that produce this activity are preserved across species including mice, rats, non-human primates, and humans, thus gamma and SWR alterations discovered in animal models extend to humans.

Develop and Optimize Sensory Flicker Methods to Drive Specific Frequencies of Neural Activity in HPC.

The data show a novel non-invasive method to drive temporally precise neural activity in HPC. First, electrophysiological recordings were performed by using 32-channel silicone probes in the hippocampal CA1 subregion of wild-type (C57BL6J) mice running or resting on a spherical treadmill. While neural activity was recorded, animals were presented with interleaved periods of (1) quiet darkness, (2) tones that turned on and off at 40 Hz (1 ms long 10 kHz tones played every 25 ms, henceforward referred to as auditory flicker stimuli), and (3) tones and lights that turned on and off at 40 Hz (1 ms long 10 kHz tones and 12.5 ms long white lights on every 25 ms, henceforward referred to as multimodal flicker stimuli). Spiking increased and decreased periodically with the tones, thus neural activity entrained to 40 Hz during 40 Hz auditory or multimodal flicker stimulation (FIG. 12). The interval between peaks in spiking rate during 40 Hz auditory flicker was around 25 ms (equivalent to 40 Hz) for the majority of recording sites. During auditory stimulation, on average 55% of recording sites had periodic spiking responses and during auditory plus visual stimulation, 61% of CA1 recording sites had periodic spiking compared to 1% of recording sites during baseline periods (FIG. 12). The depth of modulation, a measure of the amplitude of spiking modulation and ranges from 0 (no modulation) to 1 (maximum modulation), during 40 Hz auditory flicker was 0.057-0.391 and during 40 Hz auditory plus visual stimulation was 0.049-0.333 (25th-75th percentile, FIG. 6). The local field potentials in CA1 displayed elevated power at 40 Hz during 40 Hz auditory stimulation, although the effects varied between recording locations and sessions. Thus 40 Hz auditory flicker stimulation induced robust 40 Hz entrainment in CA1. Second, many single units have been recorded by using silicone probes in awake behaving animals including putative pyramidal cells and interneurons. Typically, 30-50 well-isolated units are recorded on a 32-channel silicone probe and we will improve that yield by using 128-channel probes (FIG. 12). Cell-type classification is confirmed by using optogenetic stimulation in a subset of recordings. Optogenetic stimulation and neural recordings have been previously combined in mice (FIG. 12a, b).

Figure 13:
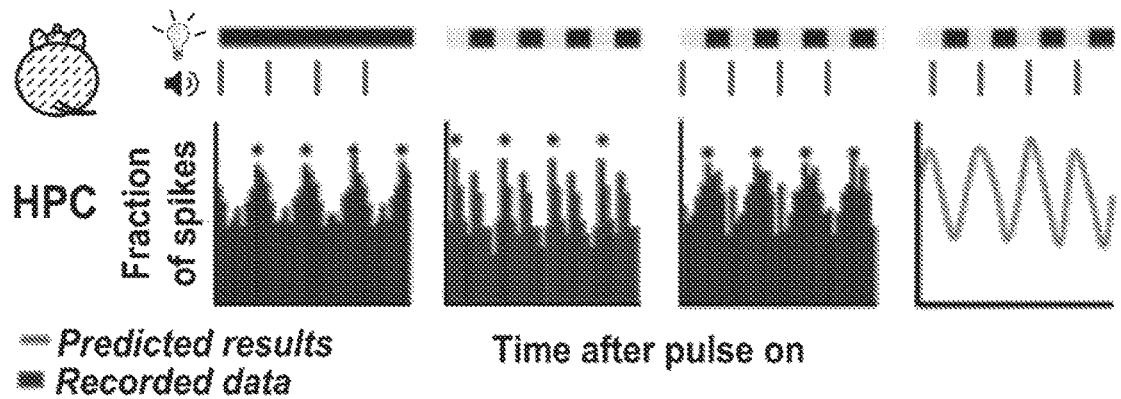
FIG. 13 shows testing different forms of sensory flicker to entrain neural activity. Animals are be exposed to auditory flicker alone, visual flicker alone, auditory and visual flicker in which both stimuli turn on simultaneously (in-phase multimodal flicker) and auditory and visual flicker in which auditory and light stimuli turn on offset by half of a cycle (offset-phase multimodal flicker).

Experimental Procedure:

First, different types of sensory flicker are tested to determine what drives the largest gamma entrainment in HPC in 3-months-old WT and 5XFAD mice (FIG. 13). Using a similar approach as in studies described above, neural activity in HPC is recorded while animals are presented with different auditory, visual, or multimodal flicker. Animals are presented with interleaved 10 s blocks of no stimuli (baseline) and flicker stimuli (alternating between auditory, visual, and multimodal flicker) to compare the effects of each stimulus within a recording. For multimodal flicker, stimuli are tested in which the light and sound turn on simultaneously (in-phase multimodal flicker) or turn on offset by half of a cycle (offset-phase multimodal flicker, FIG. 13). Animals are present with 40 Hz flicker with duty cycles (the percent of the cycle that stimulus is on) in line with previous studies and prior human research, namely auditory stimuli on for 1 ms and visual stimuli on for 12.5 ms in each 25 ms cycle. In a separate set of experiments, these duty cycles are varied, exposing animals to both visual and auditory stimuli with 4% duty cycles (on for 1 ms) or both with 50% duty cycles (on for 12.5 ms). For all stimuli, rhythmic neural entrainment is measured, including the interval between peaks in spiking rate and the depth of spiking rate modulation (FIG. 12). The effects of auditory, visual, in-phase multimodal, and offset-phase multimodal flicker are compared by using Wilcoxon rank sum tests and the Bonferroni method to correct for multiple comparisons since some results are not expected to be normally distributed. In addition, Rayleigh's circular statistical test is used to assess whether spiking is significantly locked to certain phases of the flicker stimulus. Then comparison is made regarding the number of cells significantly phase-locked to auditory, visual, in-phase multimodal, or offset-phase multimodal flicker using Wilcoxon rank sum tests and the Bonferroni method to correct for multiple comparisons. The same statistical analysis approach is used to compare the effects of different duty cycles. Also, the power spectral densities are used in the local field potential.

Figure 14:
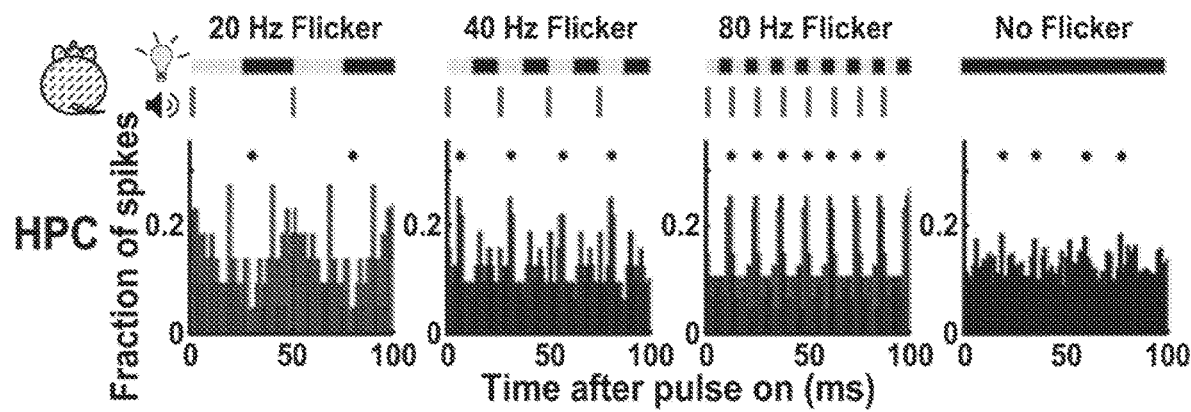
FIG. 14 shows the effects of different frequencies of sensory flicker. In preliminary studies, spiking in HPC is modulated by combined auditory and visual flicker at 20 Hz (far left), 40 Hz (center left), and 80 Hz (center right) compared to no flicker (far right) or random flicker controls. Histograms show the fraction of spikes as a function of light and tones turning on and off (above), peaks indicated with asterisks. In all studies, animals are exposed to 10 s blocks of 10, 20, 40, 60, 80, 100 Hz flicker.
Figure 16:
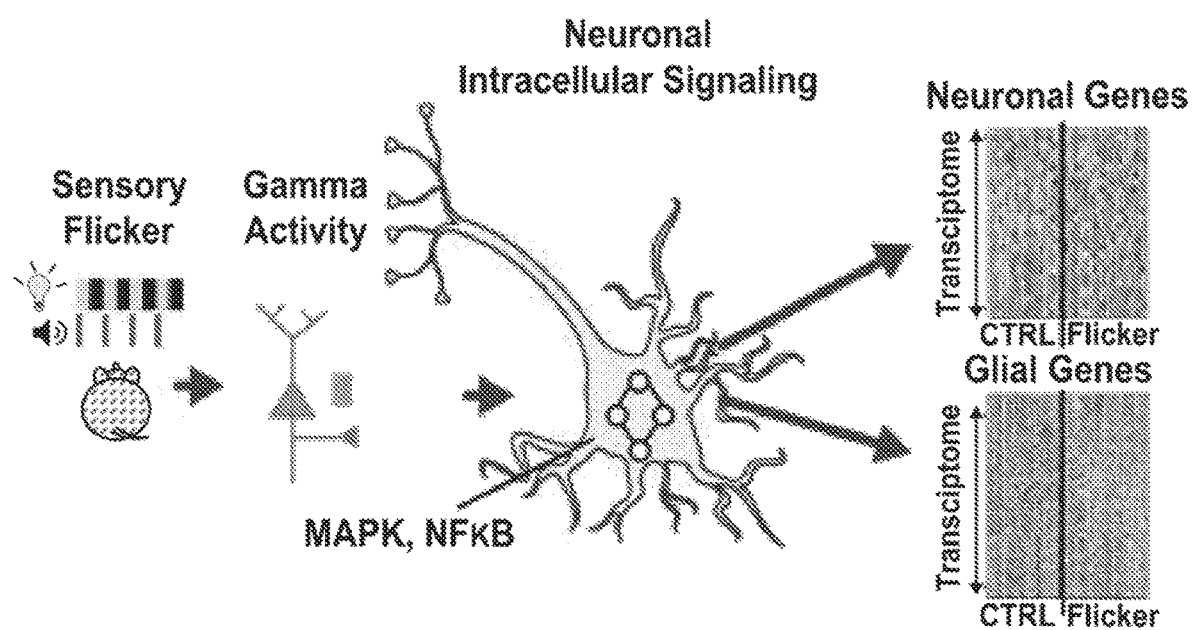
FIG. 16 shows mechanism of flicker-induced changes in gene expression. 1 effects of different patterns of stimulation on triggering gene expression patterns in the visual cortex. 2 simultaneous audio/visual flicker driving gene expression changes in deep brain regions, such as the hippocampus, relevant to Alzheimer's disease.

Second, using the flicker stimuli that produce the largest response in the first experiments, the frequency of flicker stimuli is then varied to determine over what frequency range sensory flicker entrains neural activity. Using the same approach as above, animals are exposed to 10 s blocks of 10, 20, 40, 60, 80, 100 Hz flicker (FIG. 14). Neural responses and reliability are measured as described above. A sample size of 8 male and 8 female mice per group, with 2 recordings per animal, are sufficient to detect significant differences in the percentage of periodic recording sites between flicker and baseline periods and between different frequencies of flicker at power greater 80% and p<0.05.

Example 3. A Comprehensive Map Created Between Specific Frequencies of Brain Activity Produced by Sensory Flicker and its Effects on Diverse Cellular Functions that Promote Brain Health in Alzheimer's Disease Here, a comprehensive map is created between specific frequencies of brain activity produced by sensory flicker and its effects on diverse cellular functions that promote brain health in Alzheimer's disease. It is shown that distinct frequencies and durations of stimulation trigger precise gene expression patterns that:
1. enhance memory, synaptic density, and neuronal survival
2. produce trophic factors that promote neuronal health
3. stimulate expression of factors that promote healthy neural immune function, including glial activation that can clear amyloid beta plaques and neurofibrillary tangles Thus, this work yields a "stimulation-to-gene expression map (StG Map)" using the 5xFAD mouse model of Alzheimer's pathology. This is the foundation for radical new ways to control cellular function and dysfunction in Alzheimer's disease.

This stimulation-to-gene expression (StG) map has the potential to transform the approach we develop to modifying the brain's response to Alzheimer's disease. The following innovations are identified:
1. The audio/visual sensory flicker technology is entirely noninvasive. This is the first work to determine how sensory flicker changes gene expression in deep brain regions associated with memory.
2. Although 40 Hz gamma stimulation has previously been used to change neuronal electrical activity on a time scale of seconds, this is the first work to interrogate the effects of a range of frequencies of stimulation on gene expression in the brain over multiple time scales from minutes to hours. This work thus dramatically extends previous findings that 40 Hz for 1 hr can induce expression of immune genes (FIG. 19).
3. A novel gene clustering approach is used to isolate gene expression signatures from different cell types using RNAseq data from whole tissues.

These innovations result in a first of its kind StG Map that enables us to identify noninvasive stimulation patterns that promote neuronal health, learning and memory, protective microglial activity, and amelioration of Alzheimer's amyloid pathology. Not only can this map identify protective stimulation regimens, but it also enables researchers to interrogate numerous mechanisms and pathways associated with the effects of flicker stimulation.

Visual Flicker Stimulates Cytokine Expression in a Stimulation-Dependent Manner:

Since 40 Hz gamma visual flicker promotes microglial transformation and MAPK and NFkB signaling, (FIG. 20), which strongly regulate transcription of neuroinflammation, including cytokines, protein expression of 32 cytokines/chemokines in the visual cortex is quantified after 1 hr of visual flicker. The data showed that 40 Hz flicker robustly promoted expression of numerous cytokines compared to stimulation with constant light, 20 Hz flicker, or random flicker (FIG. 17*a*). Importantly, each flicker stimulation group possessed a unique cytokine expression pattern, e.g., anti-inflammatory IL-10 was particularly stimulated by random flicker, VEGF, was most stimulated ty constant light, and 20 Hz flicker strongly suppressed all cytokines compared to the other groups (FIGS. 17*a,b*). These data show that different stimulation patterns yield expression of distinct genes important for modifying healthy neural immunity, clearing pathology, and promoting neuronal health. These data strongly support the importance of the creation of a StG Map to relate stimulation to gene expression.

It was found that different stimulation patterns yielded distinct cytokine protein expression profiles (FIG. 17*a,b*, arrows). Next, it is shown that duration and frequency of stimulation are key "levers" to produce different gene expression patterns within the brain (conceptualized in FIG. 18). These include 1) neuronal survival and trophic support, 2) synaptic plasticity, 3) microglial transformation and neural immunity.

Using combined audio+ visual flicker stimulation enables toentrain gamma in the visual cortex and the hippocampus. The StG is first created by analyzing gene expression in the visual cortex, then a companion map is created in the hippocampus, which enhances the translational relevance to Alzheimer's disease.

Mouse Cohort:

A cohort of male 5xFAD mice bred and housed in the joint Singer/Wood mouse colony at Georgia Tech. 5xFAD mice present elevated levels of soluble Aβ by 2 mo and robust plaque formation by 6 mo. To identify the effects of flicker therapy in a therapeutically relevant context of early Alzheimer's pathology, 3 mo 5xFAD mice are used for the present study.

Non-Invasive Gamma Sensory Flicker Stimulation:

5xFAD mice are exposed to a spread of flicker frequencies Hz and durations of exposure [0.5, 1, 2, 4, 8] hr. The spread of frequencies was identified due to 40 Hz flicker yielding a strong immune response in our preliminary data and because significantly lower and higher frequencies can have opposing effects on the nervous system (e.g., on plasticity). The range of durations was selected based on prior study showing that 0.5 hr of 40 Hz stimulation yielded changes in cytokine expression and 4-8 hr being a time constant associated with negative feedback within gene expression pathways. During stimulation, animals are brought to the lab, sit in a quiet room for 1 hour, placed in a clean empty exposure box and exposed to simultaneous audio/visual flicker for the prescribed time. Following flicker exposure, animals are sacrificed, brains are rapidly removed (<2 min), microdissected, and the visual cortex and hippocampus are isolated for RNA extraction. To establish a baseline, tissues from N=5 mice are collected and kept in constant light for 1 hr.

RNAseq Data Collection:

To broadly understand gene sets/pathways responsible for inflammatory response and/or cell death, RNA is isolated from each brain region (visual cortex, hippocampus) using TRIzol (Thermo Fisher). RNA quality is verified using a Bioznalyzer 2100 and only samples with RIN>6 are run. RNA is then prepared for analysis using a Nextera XT Index Kit v2 and sequenced in high output mode on Illumina NextSeq 500 (IBB, Georgia Tech Molecular Evolution and High Throughput Sequencing Core). Sequencing data are aligned using TopHat, and read counts are reported in terms of fragments per kilobase of exon per million (FPKM). Samples from each brain region are run in a single batch, so no batch effect is expected. This transcriptome-wide dataset will be content-rich and thus the data are rapidly reported in a journal manuscript and published with the StG Map discussed below.

Figure 18:
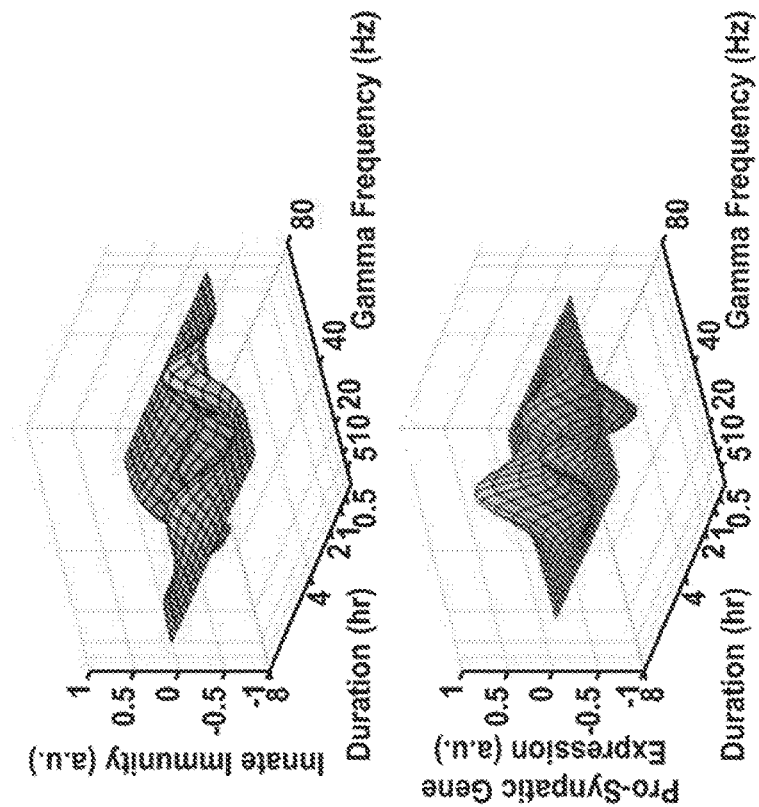
FIG. 18 shows conceptualization of stimulation-to-gene expression map (StG Map). This map identifies stimulation regiments that promote activation of different functional gene sets ("modules").
Figure 19:
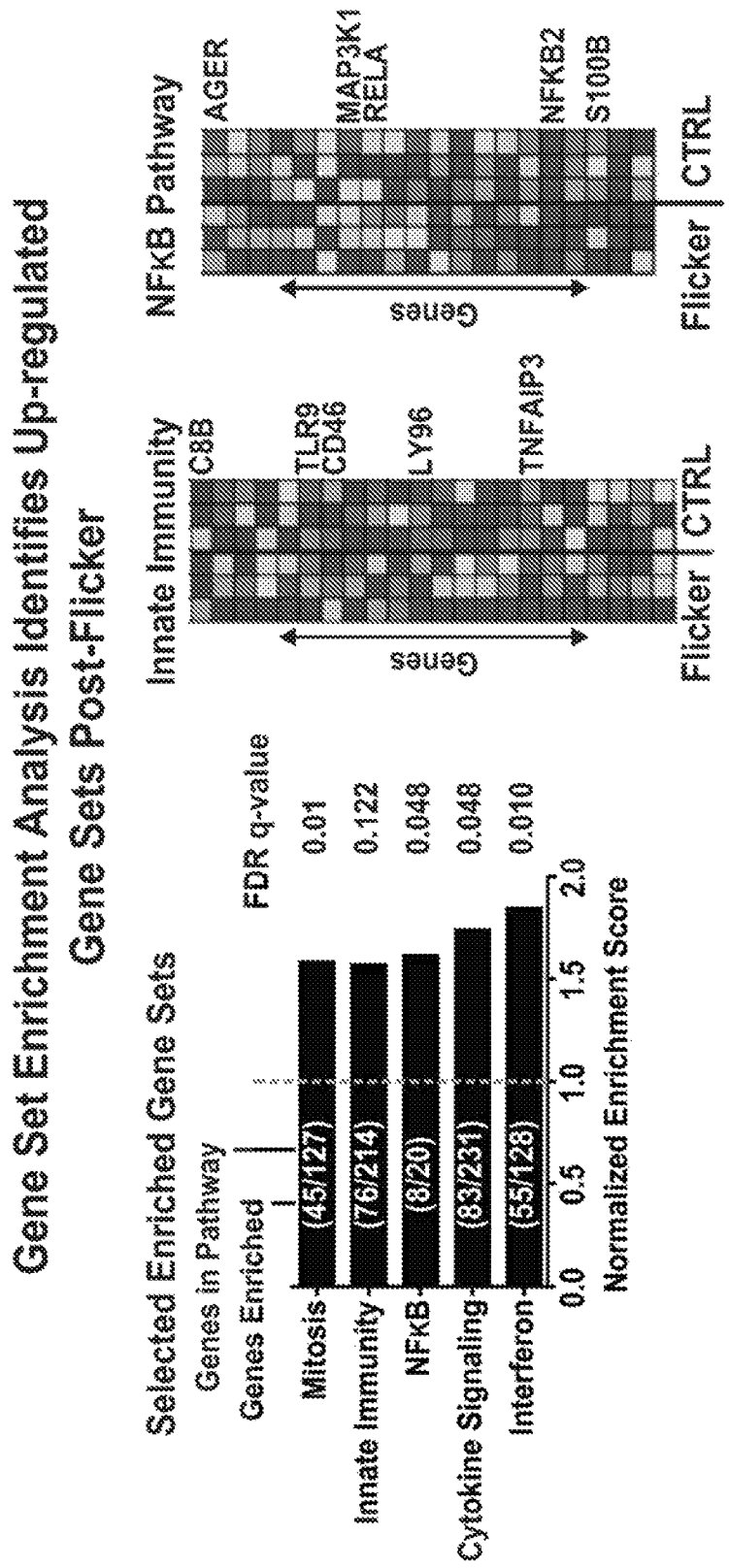
FIG. 19 shows RNAseq identifies pathway and cell-type specific gene expression.

StG Mapping:

The StG Map is the first of its kind. Therefore, three complementary mapping approaches are taken to construct the map:

1. Gene Set Enrichment: Existing curated gene sets from the Broad Molecular Signatures Database are used together with gene set enrichment analysis (GSEA) to identify enrichment of each gene set in response to each stimulation frequency/duration. A proof of principal application of this analysis is conducted to RNAseq data collected from mice exposed to either 40 Hz flicker or constant light for 1 hr (FIG. 19). This analysis identified 31 gene sets that were significantly enriched with a false discovery rate-adjusted q-value<0.25. By sweeping through frequencies and durations of stimulation and comparing each one to the constant light controls, the maps conceptualized in FIG. 18 is generated.

Figure 20C:
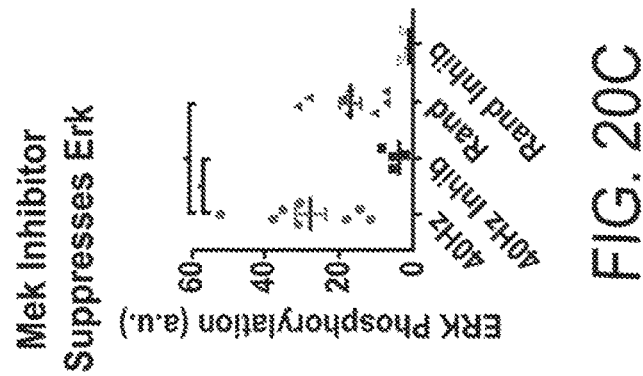
FIGS. 20A-20D. MAPK and NFκB phospho-signaling is up-regulated after exposure of mice to sensory visual flicker.
Figure 20B:
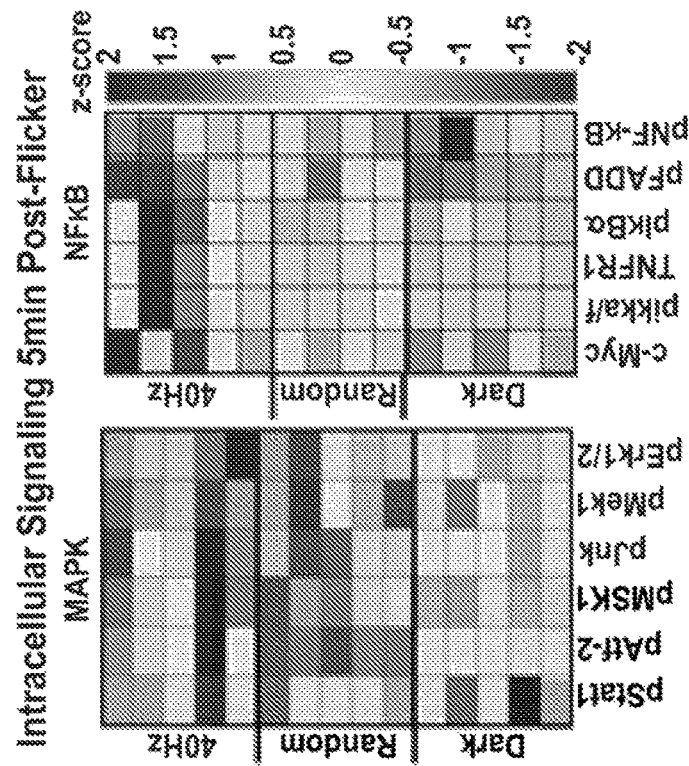
Figure 20A:
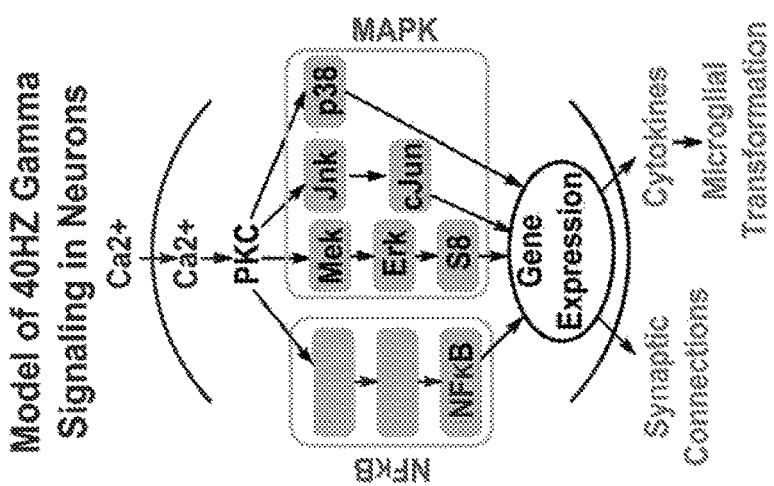
Figure 20D:
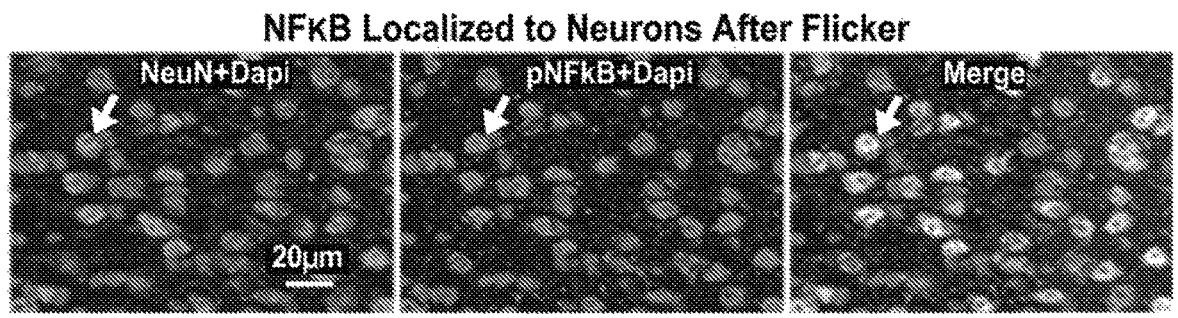

Sensory Flicker Up-Regulates Neuronal MAPK and NFκB Signaling. Immune activity is centrally regulated by intracellular signaling within several canonical kinase pathways, including the mitogen activated protein kinase (MAPK) and nuclear factor kappa-light-chain-enhancer of activated B cells (NFκB) pathways. These pathways regulate downstream expression of numerous factors, including cytokines, which are involved in recruitment and activation of microglia (FIG. 20a). Moreover, these pathways regulate immediate early genes (e.g. Arc, cFos), which are responsible for synaptic plasticity. it is next shown that MAPK and NFκB pathways, regulated by neuronal calcium influx, are the mechanisms of the dual synaptic and immune activities of flicker. To test the stimulation of these pathways by 40 Hz flicker, Luminex multiplexed ELISA panels (Millipore) are used to quantify 6 phospho-proteins in each pathway from whole-tissue visual cortex. Since activity in phospho-signaling pathways occurs much faster than gene or protein expression, tissues are collected after 5 min of visual flicker and rapidly collected brains within 2 min of euthanasia. The analysis showed that both pathways (e.g., phosphorylated Mek, Erk, Jnk, NFκB) were up-regulated in 40 Hz flicker compared to mice exposed to random stimulation or kept in the dark (FIG. 20b).

To modulate MAPK pathway signaling, mice were intraperitoneally (IP) injected with the blood-brain barrier penetrant small molecule Mek inhibitor, SL327. Assessing activity of the drug in terms of downstream Erk phosphorylation (FIG. 20c), It was found that 40 Hz flicker significantly increased phospho-Erk compared to random flicker and that the drug significantly suppressed phospho-Erk. No significant effect of the vehicle was identified (33% DMSO, 33% PEG, 33% saline; grey vs black points, FIG. 20c). In total, these data show that 40 Hz gamma flicker induce intraneuronal signaling, which can be modulated by using small molecule inhibitors.

40 Hz Flicker Induces Cytokine Expression, which is Mediated by MAPK and NFκB Signaling.

Figure 21:
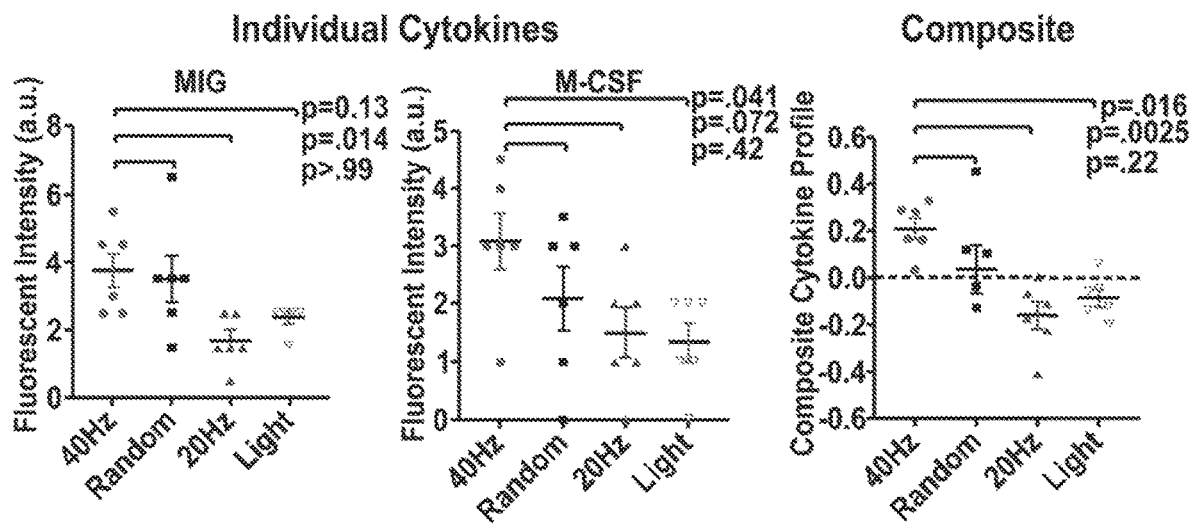
FIG. 21 shows that 40 Hz sensory visual flicker stimulates cytokine protein expression, which is suppressed by small molecule MAPK or NFκB inhibitors.
Figure 22:
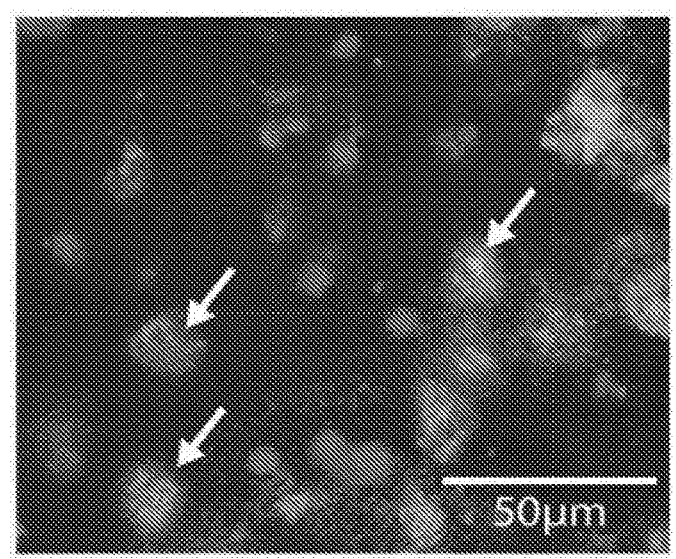
FIG. 22 IHC shows that M-CSF co-labels with NeuN after 1 hr of 40 Hz sensory visual flicker. Blue: DAPI, Green: NeuN, Red: M-CSF

To identify possible molecular mechanisms by which 40 Hz flicker and associated MAPK/NFκB signaling, recruit and transform microglia, Luminex was used to quantify expression of 32 cytokine proteins (Millipore) within the visual cortex after mice were presented with visual flicker for either 30 or 60 min. In response to 40 Hz flicker, this analysis revealed a subtle increase in certain cytokines by 30 minutes, and a pronounced increased in cytokines involved in microglial recruitment by 60 min compared to mice exposed to constant light, 20 Hz flicker, or random flicker (FIG. 21). Bar plots show selected cytokines that were significantly increased in 40 Hz flicker compared to 20 Hz flicker. Additionally, a discriminant partial least squares regression (D-PLSR) was used to identify a composite cytokine profile that strongly correlated with 40 Hz flicker. This composite cytokine profile demonstrated clear differences between groups (FIG. 21). Finally, IHC shows that M-CSF, a cytokine involved in microglial activation, was localized to the neuronal marker NeuN (FIG. 22).

Next, it is shown that MAPK and NFκB signaling mediate cytokine expression in response to 40 Hz flicker (FIG. 20a). To do so, mice are IP injected with small molecule inhibitors for each pathway 30 min prior to the start of flicker. To see if pathway inhibition would effect cytokines, MAPK inhibitors of Mek and Jnk were co-administered to inhibit the MAPK pathway in one group of mice and co-administered NFκB inhibitors of IKKβ and NFκB (curcumin, also activates Nrf2) to inhibit the NFκB pathway in a different group of mice. Excitingly, it was found that inhibition of either pathway suppressed cytokine expression in response to 40 Hz flicker. Together with the phospho-signaling data, these data show that 40 Hz flicker stimulates MAPK and NFκB pathway signaling which mediate expression of a breadth of cytokines known to regulate microglial activation and recruitment.

Mouse Models of Alzheimer's Disease have Deficits in Gamma in Vivo.

Previous work has shown deficits in gamma oscillations in mouse models of Alzheimer's, including in the transgenic 5XFAD amyloid mouse model. In particular, deficits was identified in the strength of gamma oscillations and in how well spikes are modulated by gamma oscillations during sharp wave ripples (SWRs), activity that is essential for spatial learning and memory in healthy mice. These deficits begin early in the disease prior to behavior deficits (first detected at 3-months-old). Furthermore, it has been found that driving gamma activity significantly reduced amyloid beta levels and recruited microglia to increase engulfment of amyloid. These results show that deficits in neural activity not only lead to learning and memory deficits but also contribute to the molecular and cellular pathology of AD. The deficits found in 5XFAD mice are strikingly similar to those found in humans, hAPP, and APOE4 mice. Thus, the non-invasive stimulation developed here has the potential to lead to new therapies for Alzheimer's disease, the most common dementia, or other diseases with deficits in rhythmic activity. As a result, this new non-invasive methods to drive specific patterns of rhythmic activity have wide-ranging clinical applications to modulate neural activity and impact molecular pathology. This simple non-invasive sensory stimulation is readily testable in humans. Next, we test our discoveries in human subjects with AD.

Preliminary data have demonstrated that 5XFAD Alzheimer's mice suffer reduced gamma activity. Moreover, it has been found that gamma oscillations induce intracellular signaling within the MAPK and NFκB pathways within minutes of stimulation, enhanced expression of numerous immunomodulatory cytokines within an hour, changed microglial activation after an hour, and reduced amyloid load over the course of a week. Next, it is shown that (1) MAPK and/or NFκB pathways are the mechanism by which gamma modulates neural immune activity, and (2) how gamma stimulation and the induction of these same molecular pathways affect deficits in synaptic efficacy that have been identified in mouse models of AD. This is the first work to interrogate molecular mechanisms of neuro-immune interactions, so pharmacologic perturbation of these pathways together with broad and cell-type specific analysis of tissue response yield deep insights into the mechanisms linking 40 Hz gamma with microglial neuro-immune response and learning and memory.

Generation of 5XFAD and APP/PS1 Cohorts:

3-4-month old male and female 5XFAD mice and 5-6-month old APPswe/PS1dE9 (APP/PS1) mice are used. 5XFAD mice hemizygously harbor three mutations in amyloid precursor protein and two mutations in presenilin 1, each of which is individually responsible for inherited AD in humans. APP/PS1 hemizygously harbor a single mutation each in APP and PS1 responsible for familial AD in humans. both directed to CNS neurons.

5XFAD mice present elevated soluble Aβ by 2 mo and robust plaque formation by 6 mo. It has been shown that 40 Hz flicker promotes Aβ clearance in this model.

Temporal Analysis of Immunomodulatory Signaling and Microglial Activity in Response to Flicker:

Wild-type (WT) and 5XFAD littermate mice are exposed to multi-modal audio/visual flicker (referred to as flicker). Mice are exposed to 40 Hz flicker, 20 Hz flicker, or random sensory flicker for 5 min, 1 hr, or 1 hr/day for 1 week. Random and 20 Hz groups serve as controls. During random flicker, lights and sound are presented at a randomized interval that averages 40 Hz. Random stimulation serves as a control because gamma frequency neural activity is not increased, but the same number of stimuli are delivered, on average, over the exposure period. Animals are brought to the lab, sit in a quiet room for 1 hr, placed in a clean empty exposure box and exposed to flicker or constant light for the prescribed time. For animals exposed to flicker for multiple days, this procedure is repeated at the same time each day and then animals are returned to the animal facility. Following the final flicker exposure, animals are sacrificed.

The temporal evolution of phospho-signaling, cytokine expression, and microglial phenotype in wild-type and 5XFAD mice in response to sensory flicker. For the first part, response to flicker is quantified at 5 min, 1 hr, and 1 week time points in both 5XFAD mice and wild-type littermates. These time points are selected because they correspond the shown data identifying changes in phospho-signaling (FIG. 20, 5 min), cytokine expression (FIG. 21, 1 hr), and the published finding that 1 week transforms microglial morphology and phenotype.

Experimental Groups:

Within each genotype, experimental groups consisting of 1) 40 Hz, 2) 20 Hz, and 3) random flicker are required. Neither the 20 Hz or random groups induce gamma. Based on the differences in Iba1+ microglial cell size, the differences we found in phospho-Erk between 40 Hz flicker and random animals (FIG. 20), and differences in M-CSF between 40 Hz and 20 Hz animals (FIG. 21), a power analysis (two-tailed, 80% power, α=0.05) shows that N=10 mice are required per experimental group to see differences between the 40 Hz and two control groups.

Signaling and Cytokines:

After stimulation, the left hemistphere is microdissect and Luminex (Millipore) is used to quantify phosphorylation of 12 proteins in the MAPK and NFκB pathways (FIG. 20) and 32 cytokines/chemokines (FIG. 21) at all time points from both the visual cortex and the hippocampus.

Immunohistochemistry (IHC) and Flourescent In Situ Hybridization (FISH):

The right hemisphere is fixed in 4% paraformaldehyde and use IHC to to quantify classical activation markers Iba1 (microglia, but non-specific) and GFAP (astrocytes). Additionally, IHC is used to co-label for top phospho-proteins (e.g., phospho-NFκB) and cytokines (e.g., MIG) together with the neuronal marker, NeuN (Novus), to determine their expression levels from neurons. FISH (Thermo Fisher) is also used to verify mRNA co-localization for key cytokines.

Microglial Phenotyping Via RNAseq:

For RNAseq analysis of isolated microglia, microglia are isolated from whole-brain using a CD11b+ column to avoid FACS-associated microglial activaitonTo conserve animals, this analysis is conducted at 1 hr and 1 week time points.

Quantification of Cytokines and Aβ:

Cytokines and Aβ are quantified using the methods described above. To quantify microglial response, Weighted Gene Co-expression Network Analysis (WGCNA) is used, which has recently been used to isolate inflammatory and other physiologic differences in AD patients, and which has been used to isolate Alzheimer's microglia gene expression signatures of. Using the WGCNA, it is determined how each of the gene modules changes in response to sensory flicker. Significant changes between groups are assessed using a Fisher exact test.

Deficits in Synaptic Efficacy in AD Mice:

To test whether connections between pyramidal cells and interneurons are altered in two mouse models of AD (5XFAD and APP/PS1), single units into putative excitatory pyramidal cells and inhibitory interneurons are classified by using spike width and the center of mass of the autocorrelogram. Putative monosynaptic connections and millisecond synchronous units are identified using jitter methods. To measure synaptic efficacy or strength, putative monosynaptically connected units are identified by detecting a significant peak or trough at 1-3 ms lag in the cross-correlogram of cell pairs compared to a shuffled average. Putative synchronous units are identified by detecting a significant peak at 0 ms lag in the cross correlogram of cell pairs compared to a shuffled average. Whether synaptic connections differed between AD mice and WT littermates are then compared by quantifying their connection strength, or functional synaptic efficacy. This is defined as the amplitude of the 0-3 ms range peak of the normalized cross-correlogram. Interestingly, data shows that the connection strength of the pyramidal-to-interneuron connections were significantly lower in the 5XFAD mice compared to WT littermates (FIG. 29a,b). Examining synchrony shows that there was significantly lower synchrony between interneuron-interneuron pairs but not other cell-types (FIG. 29c,d).

Example 4. Non-Invasive Sensory Stimulation Targets Deep Brain Structures in Awake Mice Results.

Figure 23A:
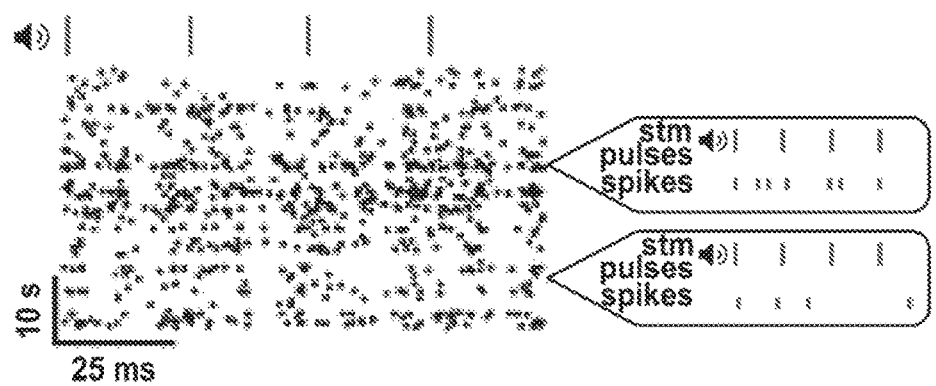
FIGS. 23A-23R show that 40 Hz auditory stimulation modulates spiking activity in AC, CA1, and mPFC.
Figure 23B:
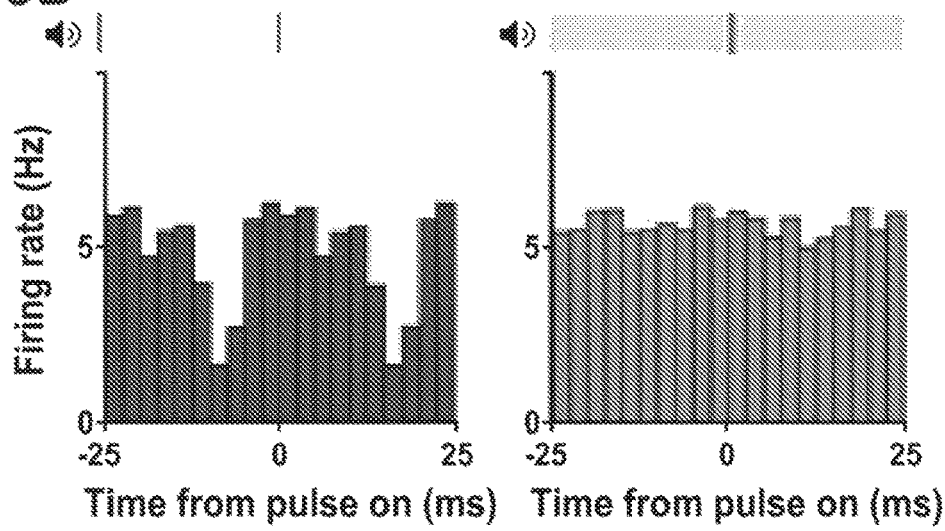
FIG. 23B show firing rate modulation of unit shown in A during 40 Hz auditory (blue) and random stimulation (orange) in AC. Blue ticks, auditory pulses; light blue bar, randomly distributed pulses.
Figure 23C:
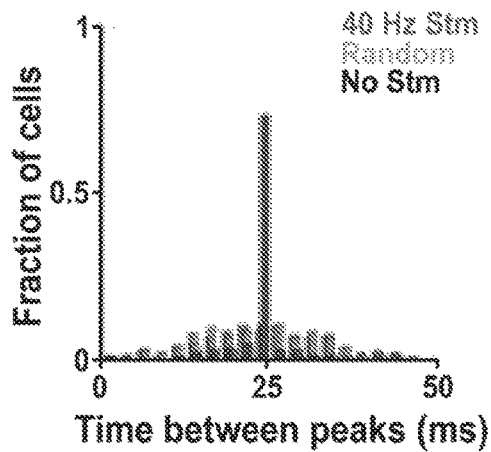
FIG. 23C shows intervals between peaks in firing rate in AC for no (grey, labeled no stim), random (orange, labeled random), and 40 Hz auditory stimulation (dark blue, labeled 40 Hz stim) conditions for all single units (n=292 units in 9 recording sessions in 5 mice. Proportion of intervals around inter-stimulus interval: P=0 40 Hz vs. No stim, P=0 40 Hz vs. Random; z-Test for two proportions. For all statistics reported, results are significant after controlling for multiple comparisons using the Bonferroni correction unless otherwise stated).
Figure 23D:
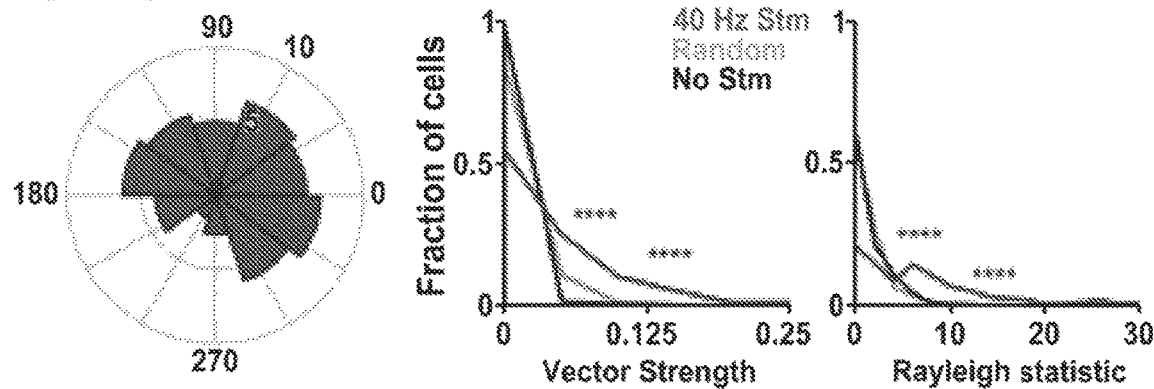
FIG. 23D shows an example polar plot of firing rate modulation relative to stimulus onset during 40 Hz auditory stimulation (left, stimulus onset at 0), vector strengths of single unit firing rate modulation during 40 Hz auditory, random, and no stimulation (center, **P<0.00005 40 Hz vs. No Stim, 40 Hz vs. Random; Kolmogorov-Smirnov test; 9 units had 40 Hz stim VS values greater than 0.25; 6 units had random stim VS values greater than 0.25), and Rayleigh statistic values of single unit firing rate modulation (right, P<0.00005 40 Hz vs. No Stim, 40 Hz vs. Random; Kolmogorov-Smirnov test; 40 units had 40 Hz stim RS values greater than 30; 2 units had random 40 Hz stim RS values greater than 30).
Figure 23E:
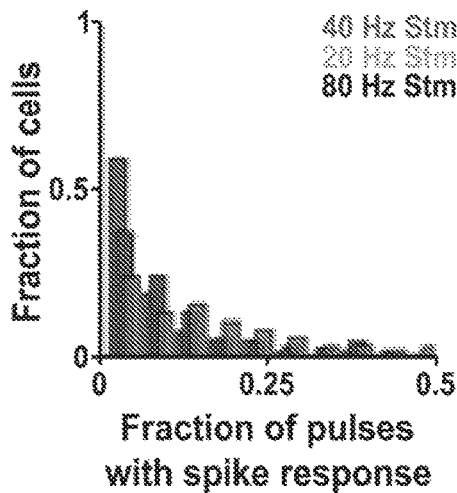
FIG. 23E shows fraction of pulses with spiking response from single units in AC for 20 Hz, 40 Hz, and 80 Hz auditory stimulation.
Figure 23F:
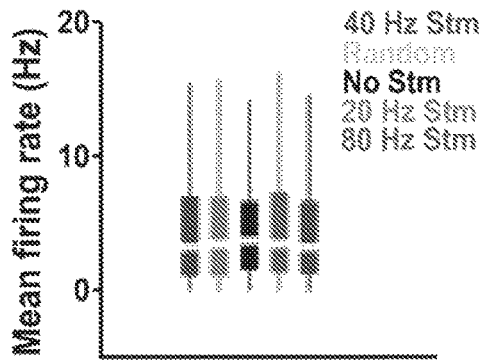
FIG. 23F shows mean firing rates between stimulation conditions in AC.
Figure 23G:
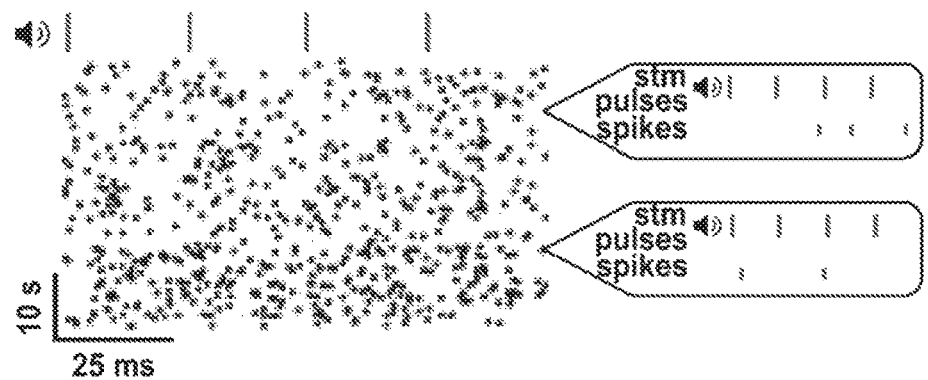
FIG. 23G shows the same as (23A) for CA1
Figure 23H:
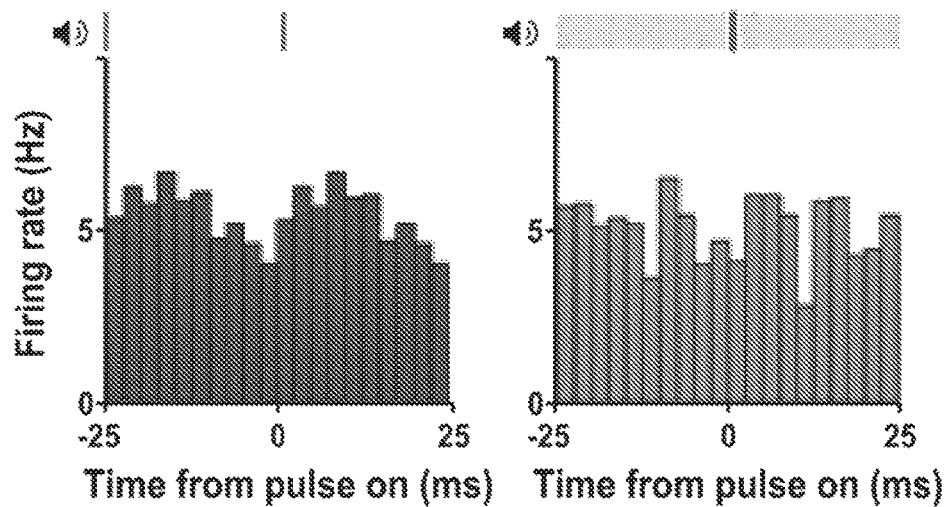
FIG. 23H shows the same as (23B) for CA1
Figure 23I:
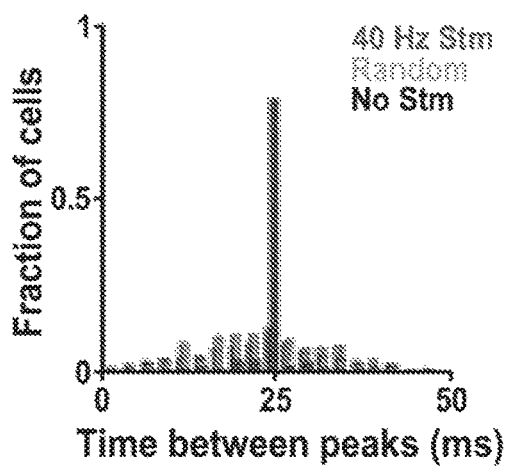
FIG. 23I shows the same as (23C) for CA1 (n=338 units in 10 recording sessions in 5 mice. P=0 40 Hz vs. No stim, P=0 40 Hz vs. Random; z-Test for two proportions).
Figure 23J:
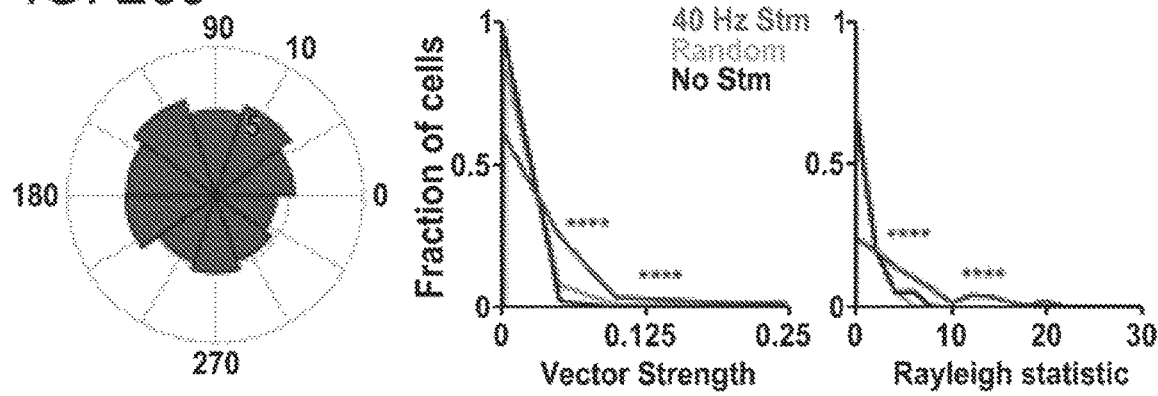
FIG. 23J shows the same as (23D) for CA1 (center, P<0.00005 40 Hz vs. No Stim, 40 Hz vs. Random; Kolmogorov-Smirnov test; 11 units and 2 units had VS values >0.25 during 40 Hz or random, respectively; right, P<0.00005 40 Hz vs. No Stim, 40 Hz vs. Random; Kolmogorov-Smirnov test; 7 units had 40 Hz stim RS values >30).
Figure 23K:
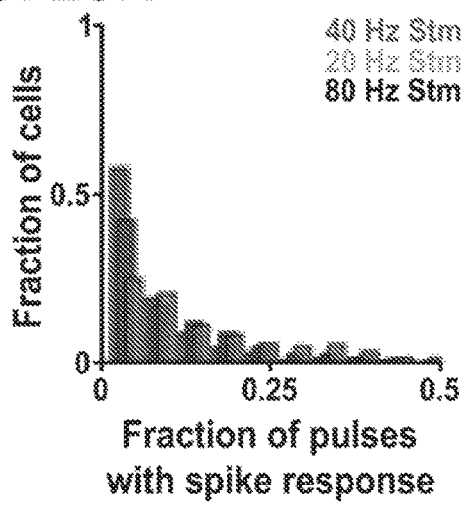
FIG. 23K shows the same as (23E) for CA1
Figure 23L:
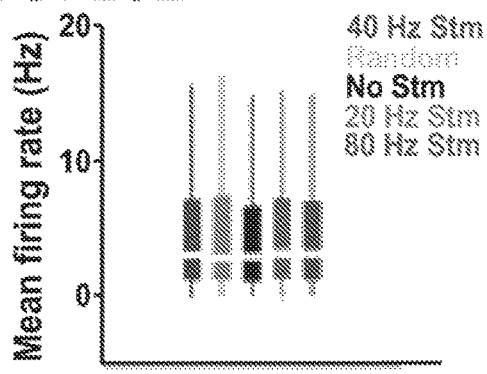
FIG. 23L shows the same as (23F) for CA1
Figure 23M:
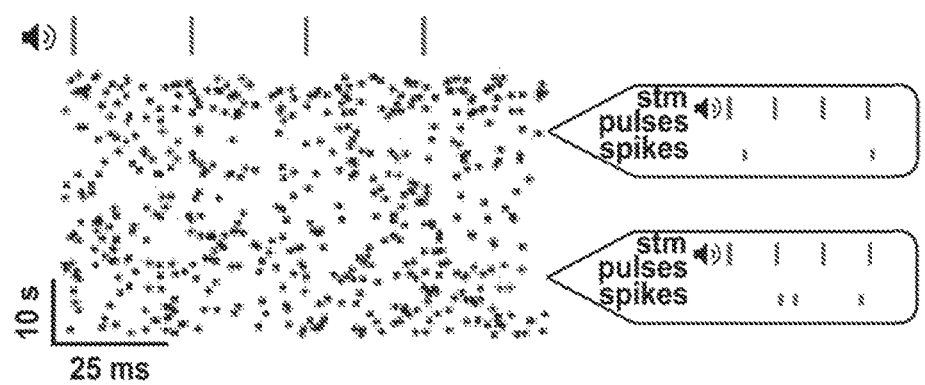
FIG. 23M shows the same as (23A) for mPFC.
Figure 23N:
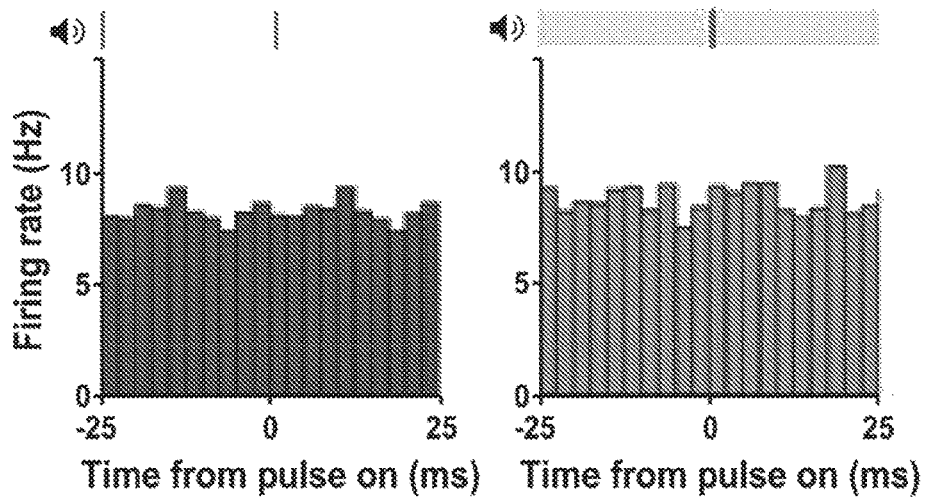
FIG. 23N shows the same as (23B) for mPFC.
Figure 23O:
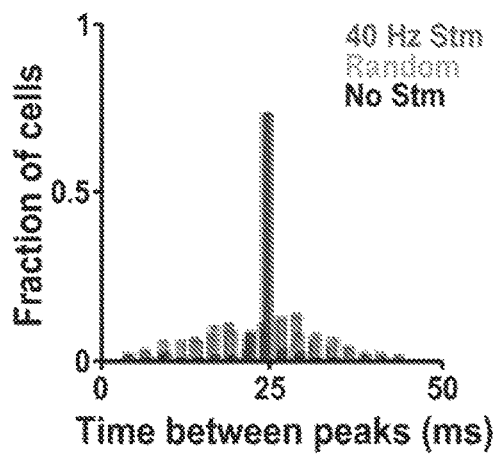
FIG. 23O shows the same as (23C) for mPFC (n=115 units in 7 recording sessions in 4 mice. P=0 40 Hz vs. No stim, P=0 40 Hz vs. Random; z-Test for two proportions).
Figure 23P:
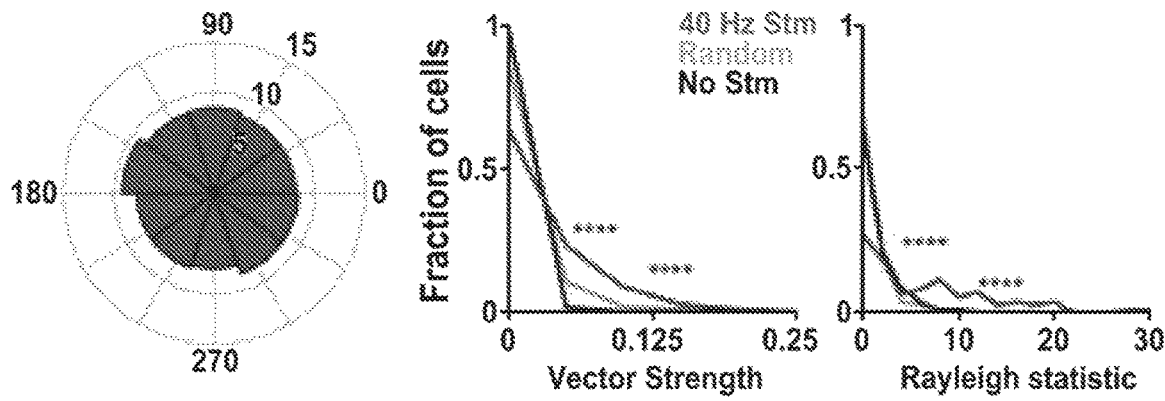
FIG. 23P shows the same as (23D) for mPFC (center, P<0.00005 40 Hz vs. No Stim, 40 Hz vs. Random; Kolmogorov-Smirnov test; right, **P<0.00005
Figure 23Q:
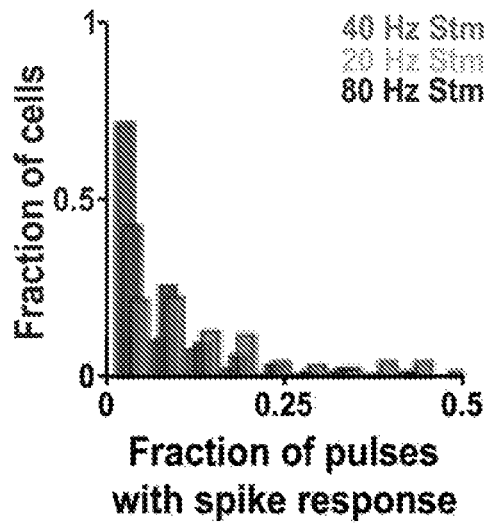
FIG. 23Q shows the same as (23E) for mPFC.
Figure 23R:
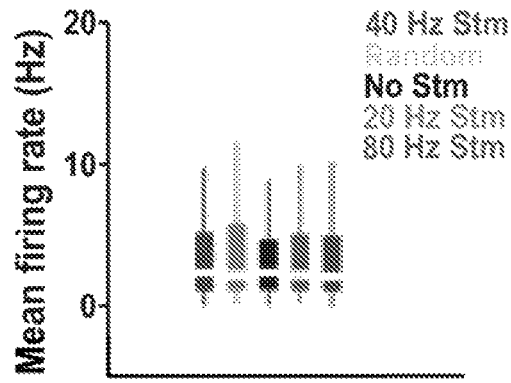
Figure 24A:
Figure 24B:
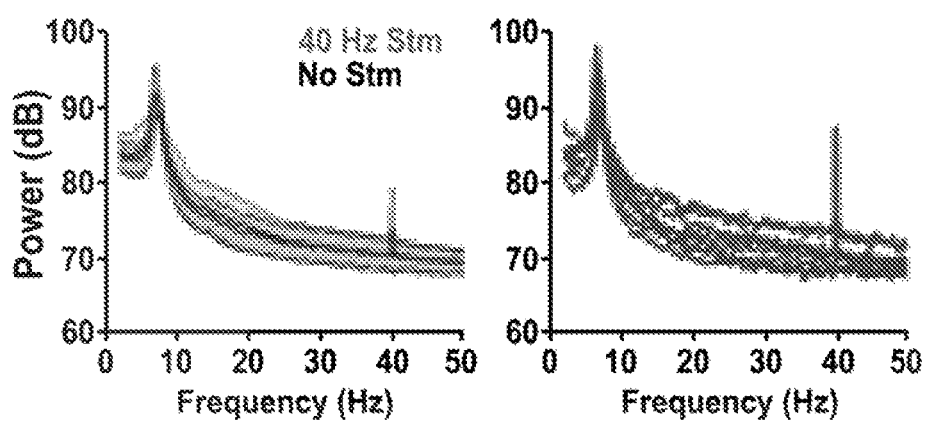
FIG. 24B shows power spectral density (PSD) response to 40 Hz auditory flicker stimuli and no stimulation periods, with mean and standard deviation across recording days (left), power spectrum LFP response to auditory flicker of all recording days in AC (recording site with largest 40 Hz peak during 40 Hz auditory flicker per recording depth is shown, see Methods) (right).
Figure 24C:
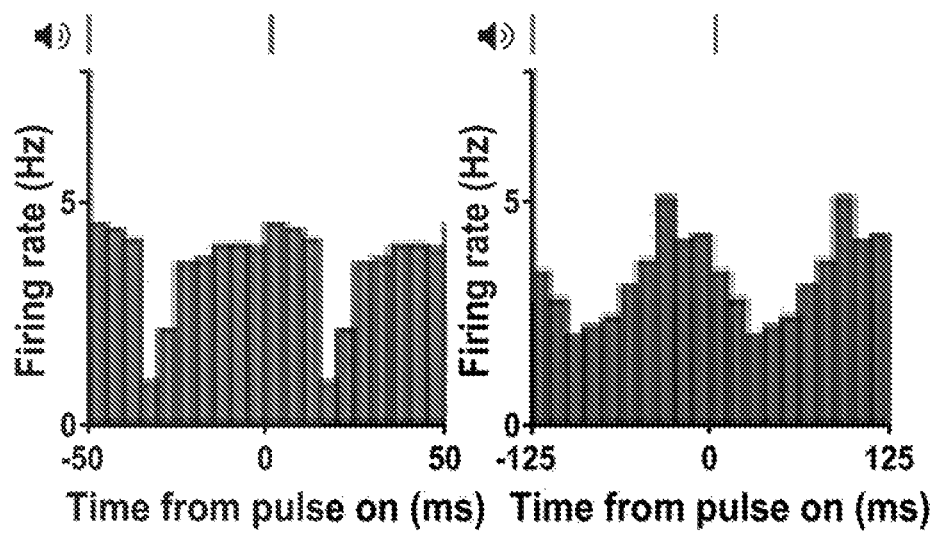
FIG. 24C shows firing rate modulation of a putative single unit in response to 20 Hz audio flicker stimulation (left, green) and 80 Hz auditory flicker (right, purple).
Figure 24D:
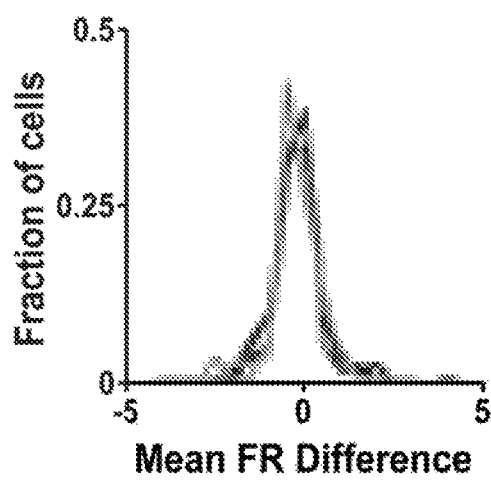
FIG. 24D shows mean firing rate difference between multiple stimulation conditions of single units in AC centers around 0 Hz ($P > 0.01$ 20 Hz-40 Hz, n.s. after controlling for five comparisons; **$P < 0.00002$ 40 Hz-no stimulation; all others n.s.; Wilcoxon signed rank test for zero median. In all statistical tests, significance remains after controlling for multiple comparisons using the Bonferroni correction, unless otherwise stated).
Figure 24H:
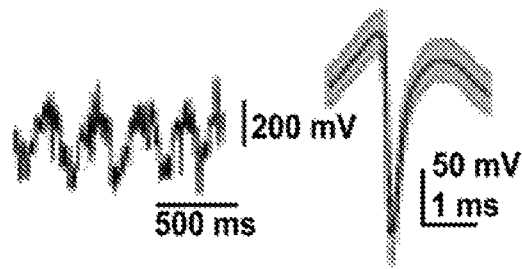
FIG. 24H shows an example of theta rhythm, a hallmark of hippocampus, used to detect CA1.
Figure 24I:
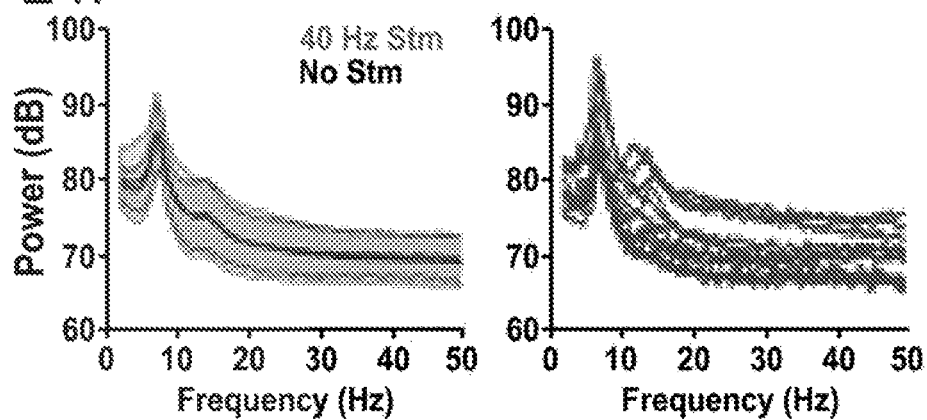
FIG. 24I shows the same as (24B) for CAL
Figure 24J:
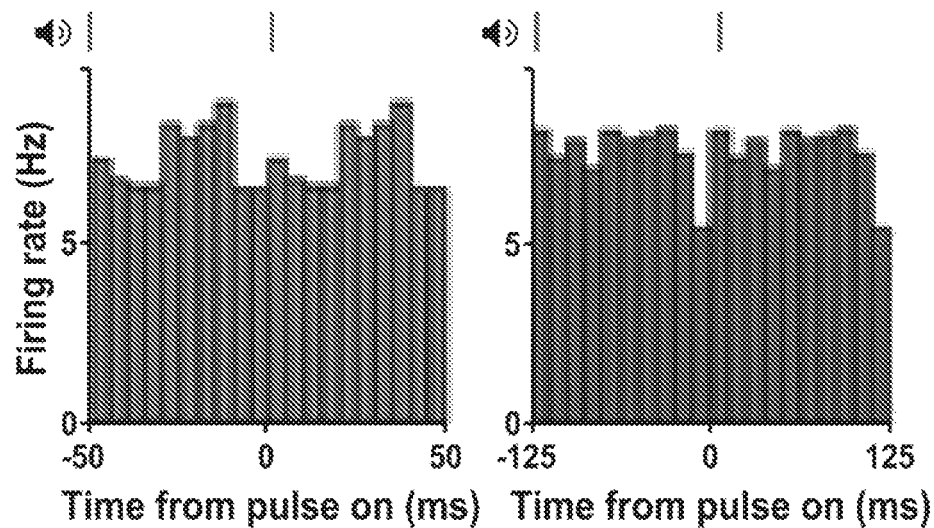
FIG. 24J shows the same as (24C) for CAL
Figure 24K:
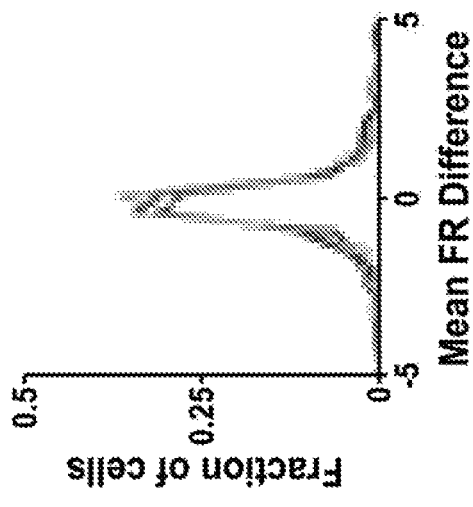
FIG. 24K shows the same as (24D) for CA1 ($P > 0.01$ 40 Hz—no stimulation, n.s. after controlling for five comparisons; all others n.s.; Wilcoxon signed rank test for zero median).
Figure 24L:
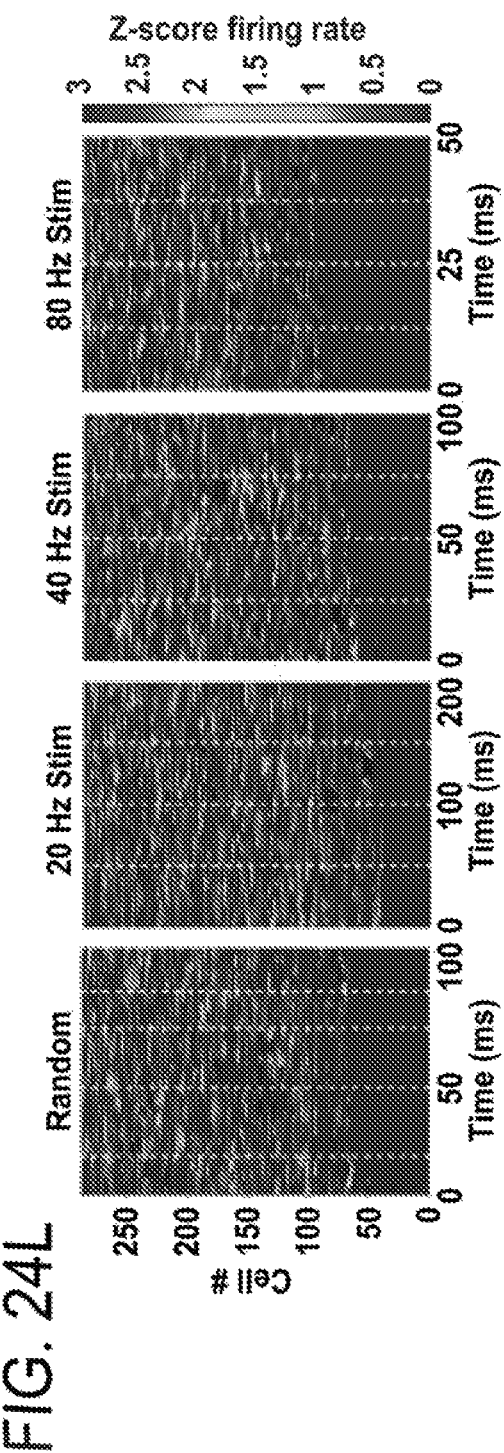
FIG. 24L shows the same as (24E) for CAL
Figure 24M:
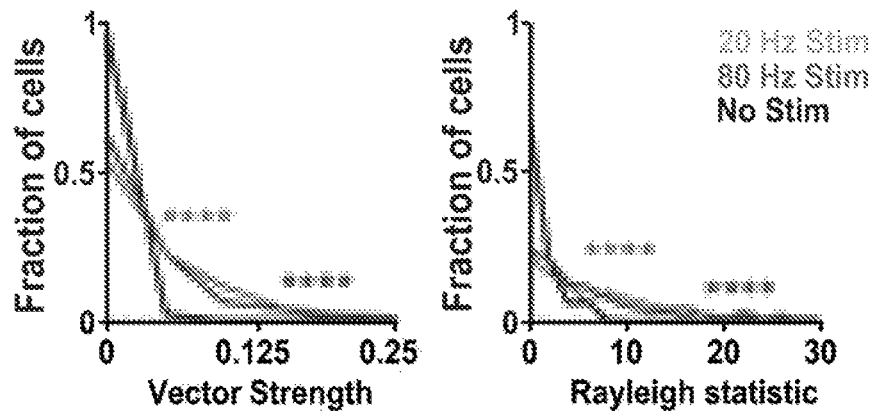
FIG. 24M shows the same as (24F) for CA1 (left, $P < 0.00005$, 20 Hz vs. No Stim, 80 Hz vs. No Stim; Kolmogorov-Smirnov test; 12 units had 20 Hz stim VS values greater than 0.25; 10 units had 80 Hz stim VS values greater than 0.25; right, $P < 0.00005$, 20 Hz vs. No Stim, 80 Hz vs. No Stim; Kolmogorov-Smirnov test; 4 units had 20 Hz stim RS values greater than 30; 5 units had 80 Hz stim RS values greater than 30).
Figure 24N:
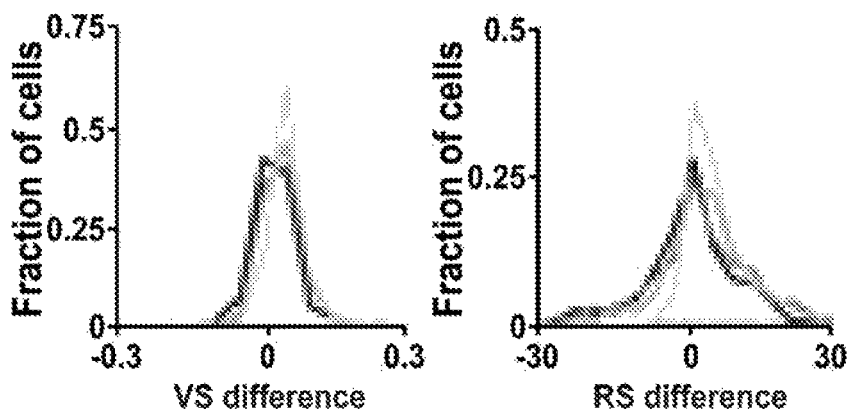
FIG. 24N shows the same as (24G) for CA1 (left, $P < 0.0025$ 20 Hz-80 Hz; *$P < 0.00025$ 20 Hz-40 Hz; $P < 0.000025$ 40 Hz—random, 40 Hz-80 Hz n.s.; Wilcoxon signed rank test for zero median; right, $P > 0.0125$ 20 Hz-80 Hz, n.s. after controlling for four comparisons; $P < 0.0025$ 20 Hz-40 Hz, **$P < 0.000025$ 40 Hz—Random, 40 Hz-80 Hz n.s.; Wilcoxon signed rank test for zero median).
Figure 24O:
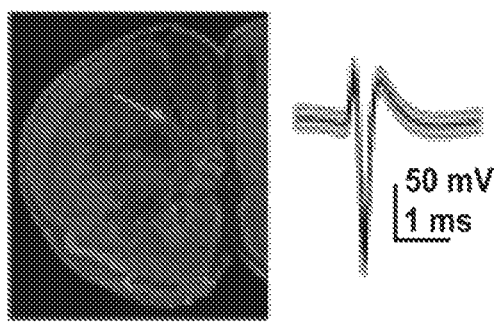
FIG. 24O shows histology image showing probe trace and recording location in mPFC. Red arrow indicates recording location.

40 Hz auditory stimulation modulates spiking activity in AC, CA1, and mPFC. To determine whether auditory tone stimulation can produce GENUS in AC, area CA1 of HPC, and mPFC, animals were present with trains of tones repeating at 20 Hz, 40 Hz, 80 Hz, or with trains of randomly spaced tones (1 ms-long, 10 kHz tones played every 12.5 ms, 25 ms, 50 ms, or with random inter-tone intervals, henceforward referred to as "auditory stimulation", Methods). Neural activity in AC, CA1, or mPFC during tone presentation was recorded by using 32 channel silicon probes in 3-8 month old male wild-type (C57BL6J) mice as they ran or rested on a spherical treadmill. The firing rate of putative single units increased and decreased periodically with each tone thereby entraining to the 40 Hz auditory stimulation (FIGS. 23A, G, and M; FIGS. 23B, H, and N, blue). Units were also modulated by random stimulation: when all random pulses were aligned, there was a change in firing rate modulation following the stimuli, indicating that single units responded to the random stimuli pulses. However, the random train of auditory tones did not induce periodic firing modulation because the stimuli themselves were not periodic (FIGS. 23B, H, and N, orange). Entrainment to auditory stimulation varied between single units in both phase distribution and amplitude. During auditory stimulation, neurons fired as a function of the stimulus, but did not fire on every cycle and often at a wide range of phases: in response to 40 Hz auditory stimulation most neurons fired every 0-22 pulses in AC, 0-30 pulses in CA1, and 0-34 pulses in mPFC ($1^{st}$-$3^{rd}$ quartiles reported; FIGS. 23B, H, and N; FIGS. 23E, K, and Q), although the interval between peaks in firing rate was around 25 ms (equivalent to 40 Hz) in the majority of single units (FIGS. 23C, I, and O). In contrast, during baseline periods with no tones and periods with random tones, the interval between peaks had a broad distribution around 25 ms (i.e. the firing rate was not modulated at 40 Hz; FIGS. 23C, I, and O). Modulation strength was quantified by considering single unit firing rate as a function of the stimulus phase and calculating its vector strength (VS) (FIGS. 23D, J, and P, left). Vector strength values range from 0 to 1:0 represents a uniform distribution of firing not modulated by the stimulus (VS=0) and 1 represents a distribution where a neuron only fired to a specific stimulus phase (VS=1). The distribution of vector strengths of single-unit response to 40 Hz auditory stimulation was significantly higher than no stimulation and random stimulation (FIGS. 23D, J, and P, center). Random stimulation vector strengths were also significantly higher than no stimulation (because vector strength measures modulation by a stimulus), but it did not induce periodic firing modulation. Similarly, the distribution of Rayleigh statistics for single units during 40 Hz auditory stimulation was significantly higher than that of no stimulation and random stimulation controls (FIGS. 23D, J and P, right). Differences in vector strength and Rayleigh statistics between stimulation conditions within single units showed that neurons were more strongly modulated by periodic stimuli, and that single units were significantly more strongly modulated by lower frequencies of stimulation (FIGS. 24G, N, and U). The mean firing rate of single neurons was similar between 40 Hz auditory stimulation and no stimulation, random stimulation, 20 Hz, and 80 Hz auditory stimulation controls (FIGS. 23F, L, and R; FIGS. 24D, K, and R). Local field potentials in AC displayed elevated power at 40 Hz during 40 Hz auditory stimulation, but the effects varied between recording locations, recording sessions, and response latency to mapping tones (FIGS. 24B, I, and P). These findings suggest that 40 Hz auditory stimulation induces GENUS robustly in AC, CA1, and mPFC.

Figure 24P:
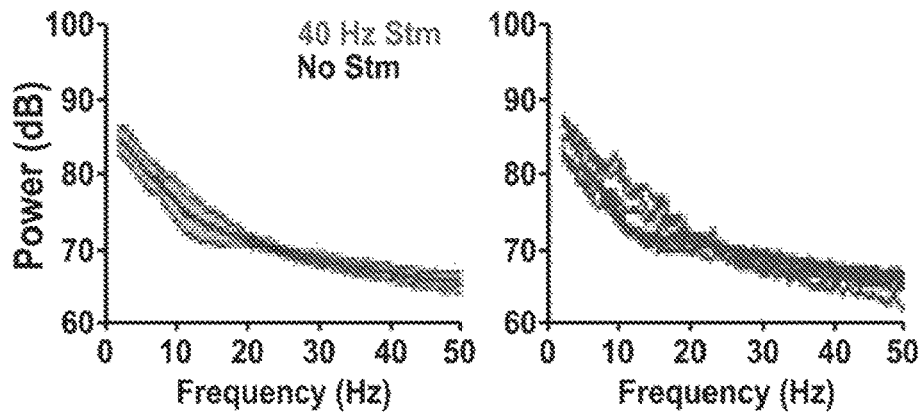
FIG. 24P shows the same as (24B) for mPFC.
Figure 24Q:
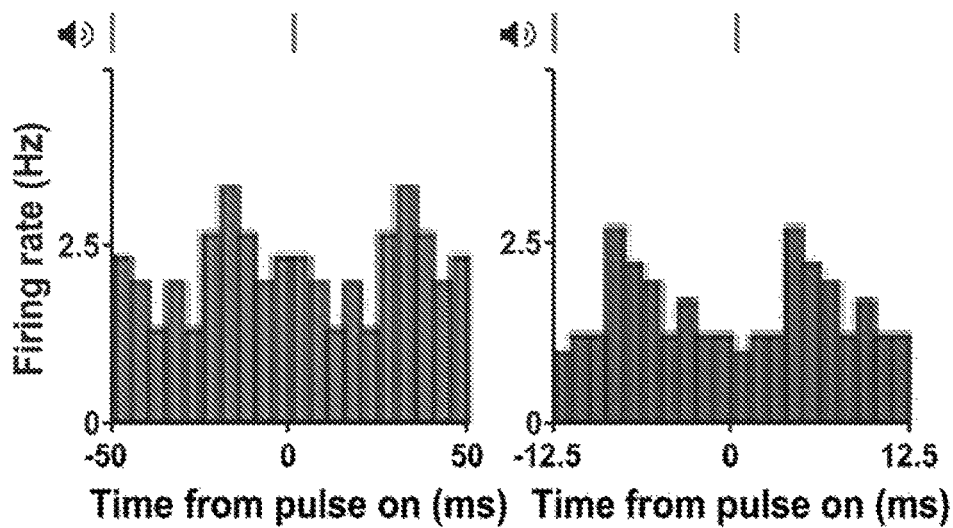
FIG. 24Q shows the same as (24C) for mPFC.
Figure 24R:
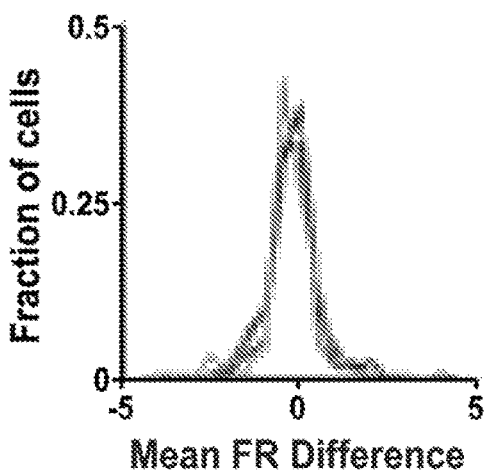
FIG. 24R shows the same as (24D) for mPFC (right, n.s.; Wilcoxon signed rank test for zero median).
Figure 25A:
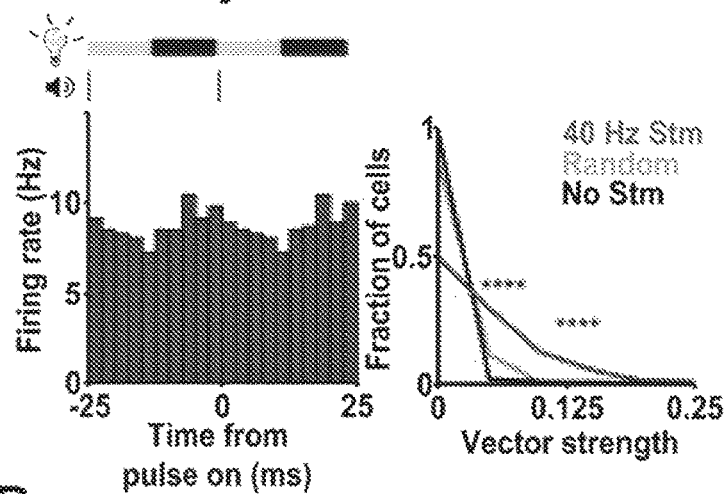
FIGS. 25A-25C show combined auditory and visual GENUS induces a clustering phenotype response by microglia.
Figure 25B:
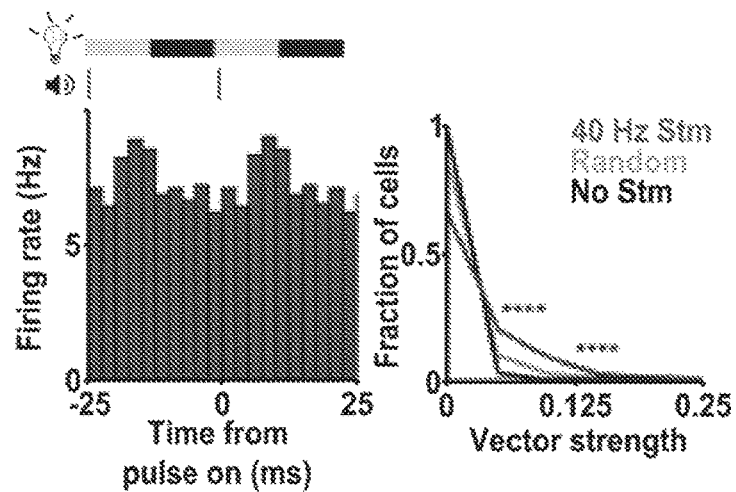
Figure 25C:
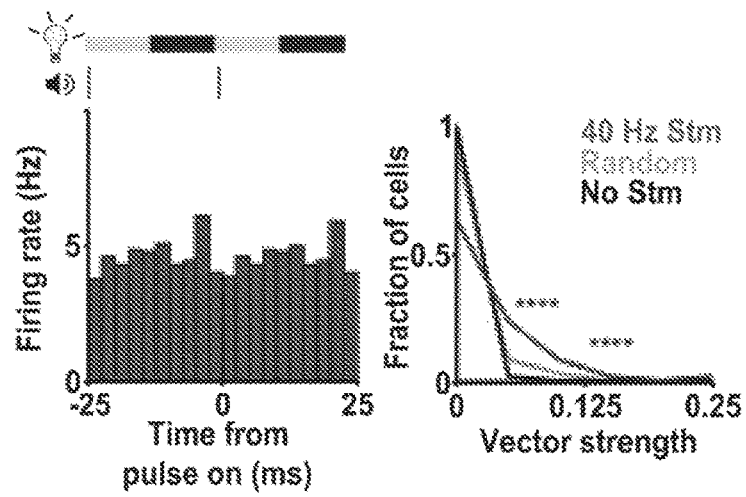
Figure 26D:
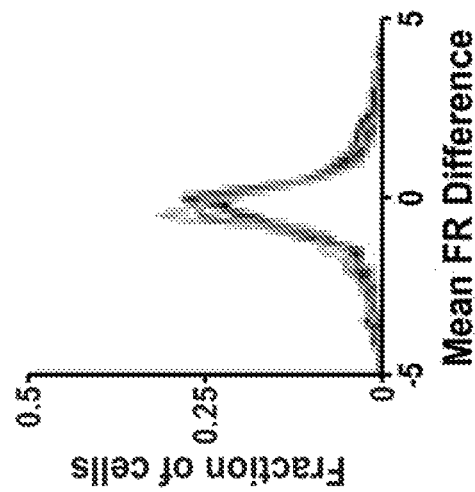
FIG. 26D shows mean firing rate difference of single units between multiple stimulation conditions in AC centers around 0 Hz ($P > 0.01$ 40 Hz—no stimulation, n.s. after controlling for five comparisons; all others n.s.; Wilcoxon signed rank test for zero median).
Figure 26E:
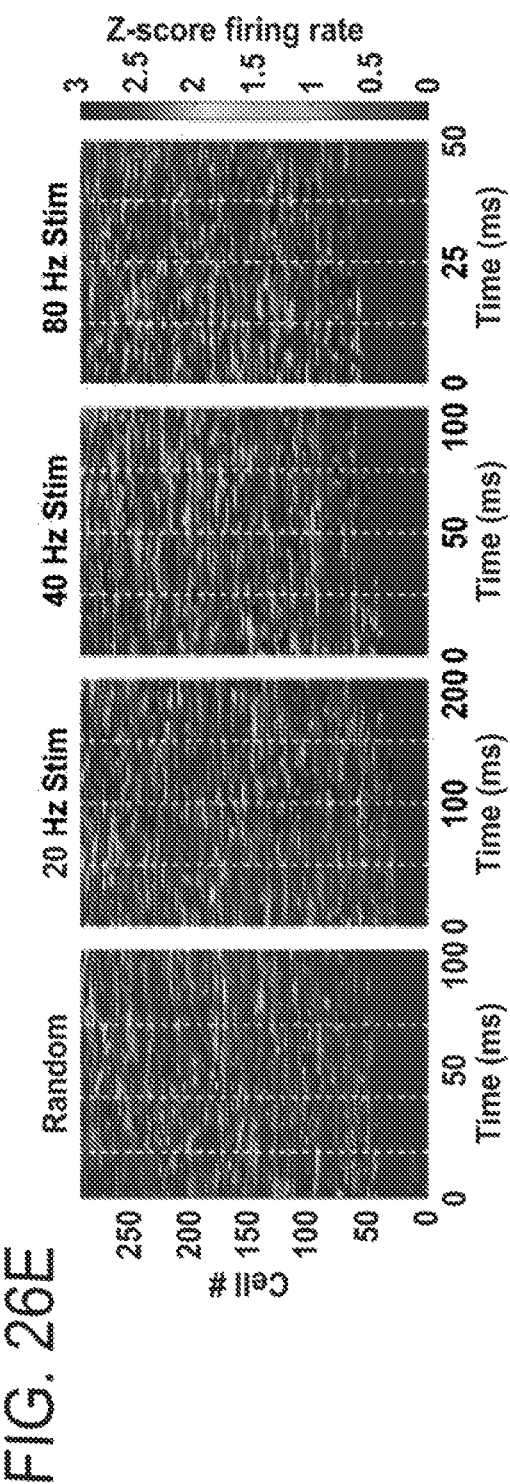
FIG. 26E shows the firing rate response of each single unit isolated in AC to Random, 20 Hz, 40 Hz, and 80 Hz audio-visual stimulation. Z-scored response to four consecutive stimulus cycles is shown. Units are ordered by their average stimulus phase preference in the analyzed four cycles. White dashed lines indicate auditory pulse timing.
Figure 26F:
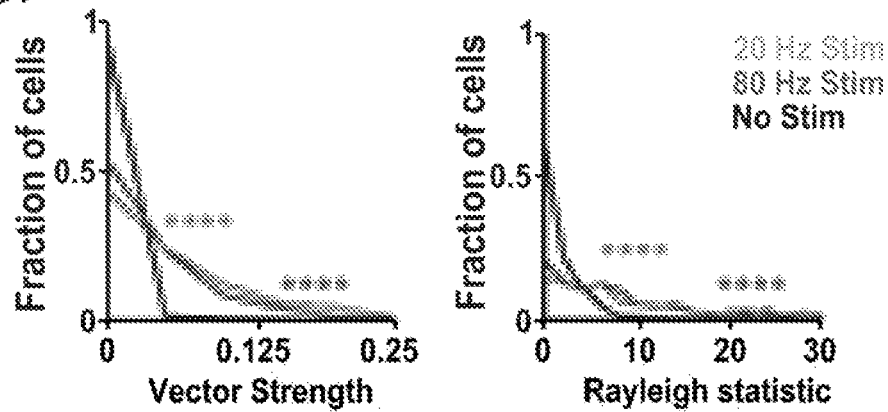
FIG. 26F shows vector strength distribution of 20 Hz and 80 Hz audio-visual stimulation vs. no stimulation condition (left, $P<0.00005$ 20 Hz vs. No Stim, 80 Hz vs. No Stim; Kolmogorov-Smirnov test; 12 units had 20 Hz stim VS values greater than 0.25; 10 units had 80 Hz stim VS values greater than 0.25), and Rayleigh statistic distribution of 20 Hz and 80 Hz audio-visual stimulation vs. no stimulation (right, $P<0.00005$ 20 Hz vs. No Stim, 80 Hz vs. No Stim; Kolmogorov-Smirnov test; 86 units had 20 Hz stim RS values greater than 30; 35 units had 80 Hz stim RS values greater than 30).
Figure 26G:
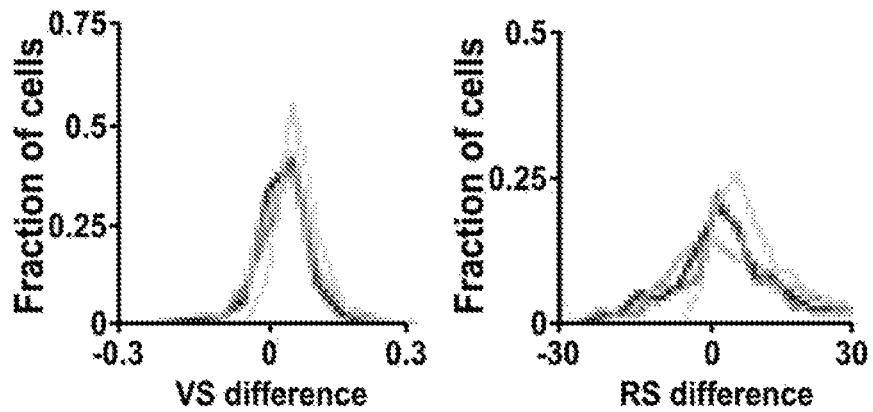
FIG. 26G shows the distribution of within cell differences in vector strength values between all frequencies of auditory stimulation (left, *$P<0.00025$ 20 Hz—40 Hz; **$P<0.000025$ 20 Hz-80 Hz, 40 Hz—Random; 40 Hz-80 Hz n.s.; Wilcoxon signed rank test for zero median). Within cell differences in Rayleigh statistic values between all frequencies of auditory stimulation (right, *$P<0.00025$ 20 Hz-80 Hz; **$P<0.000025$ 20 Hz-40 Hz, 40 Hz—Random; 40 Hz-80 Hz n.s.; Wilcoxon signed rank test for zero median).
Figure 26H:
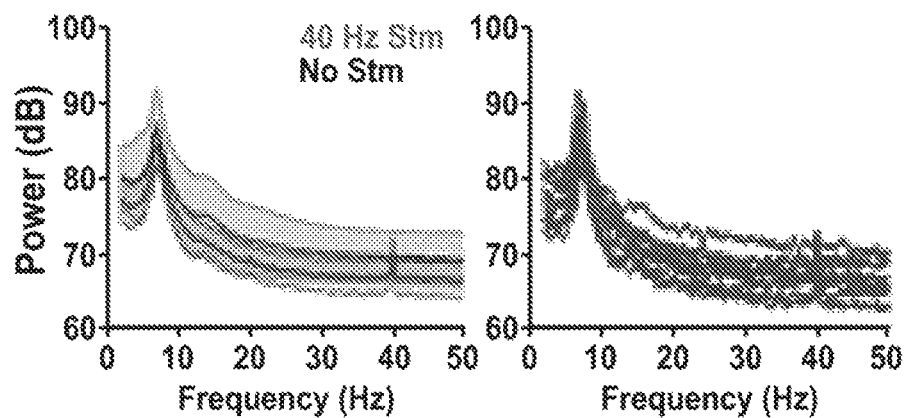
FIG. 26H shows the same as (26A) for CA1
Figure 26I:
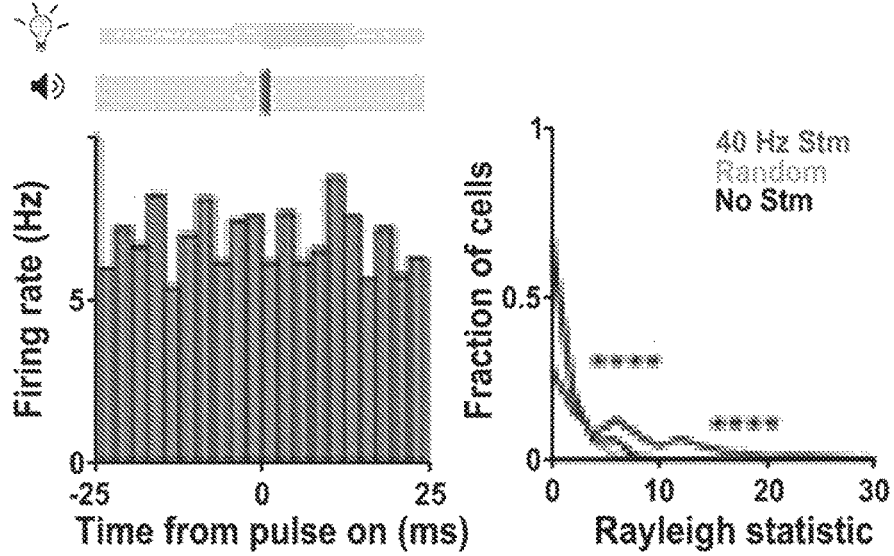
FIG. 26I shows the same as 26B for CA1 (right, $P<0.00005$ 40 Hz vs. No Stim, 40 Hz vs. Random; Kolmogorov-Smirnov test; 8 units had 40 Hz stim RS values greater than 30).
Figure 26J:
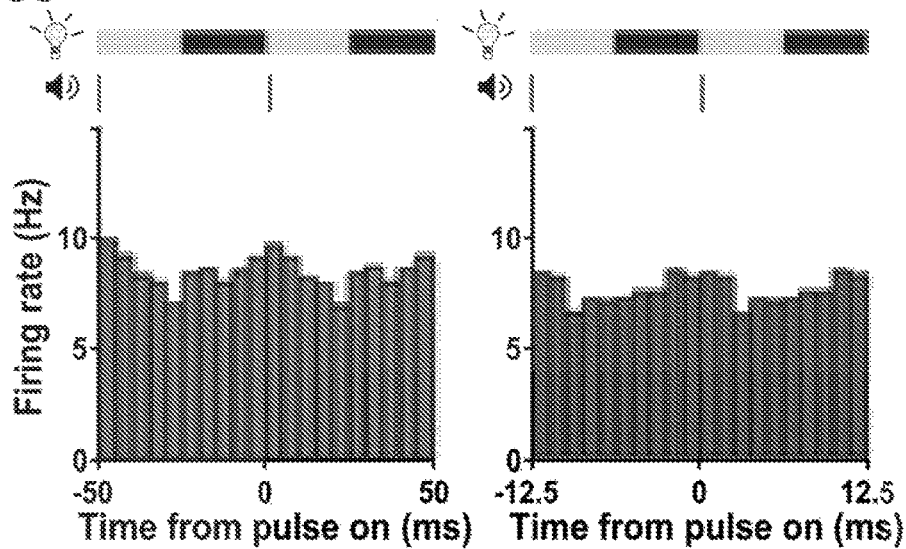
FIG. 26J shows the same as 26C for CA1
Figure 26K:
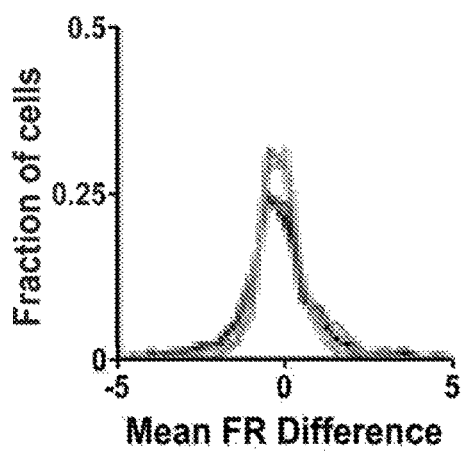
FIG. 26K shows the same as 26D for CA1 ($P>0.01$ 40 Hz—no stimulation, n.s. after controlling for five comparisons; all others n.s.; Wilcoxon signed rank test for zero median).
Figure 26L:
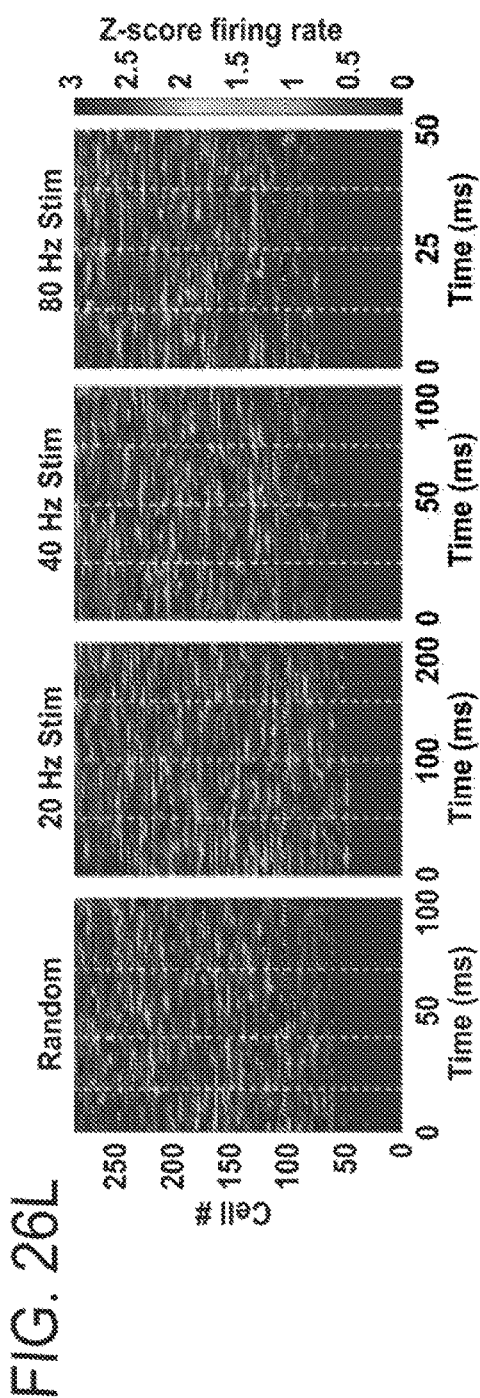
FIG. 26L shows the same as (26E) for CA1
Figure 26N:
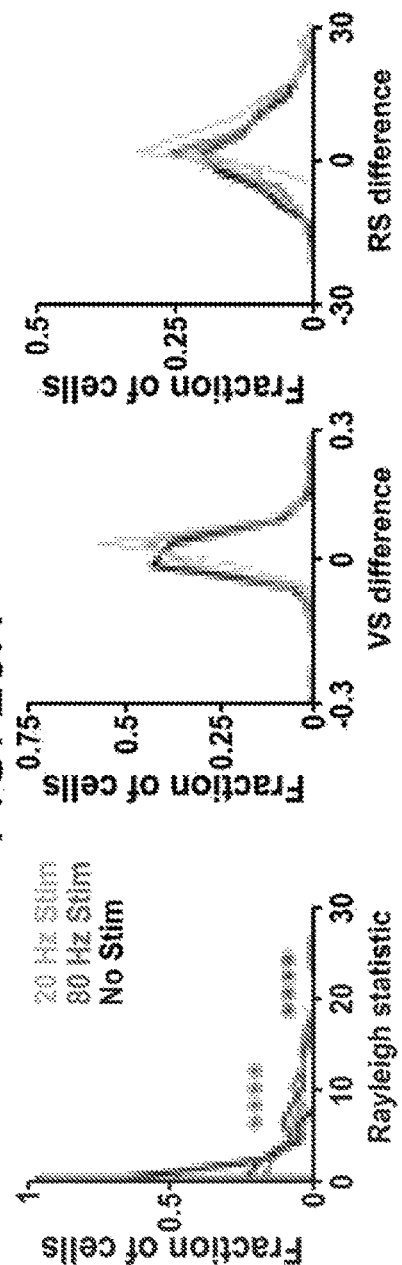
FIG. 26N shows the same as (26G) for CA1 (left, *$P<0.00025$ 20 Hz-40 Hz; **$P<0.00025$ 20 Hz-80 Hz, 40 Hz—random; 40 Hz-80 Hz n.s.; Wilcoxon signed rank test for zero median; right, $P<0.0025$ 20 Hz-40 Hz; **$P<0.000025$ 40 Hz—Random; all others n.s.; Wilcoxon signed rank test for zero median).
Figure 26M:
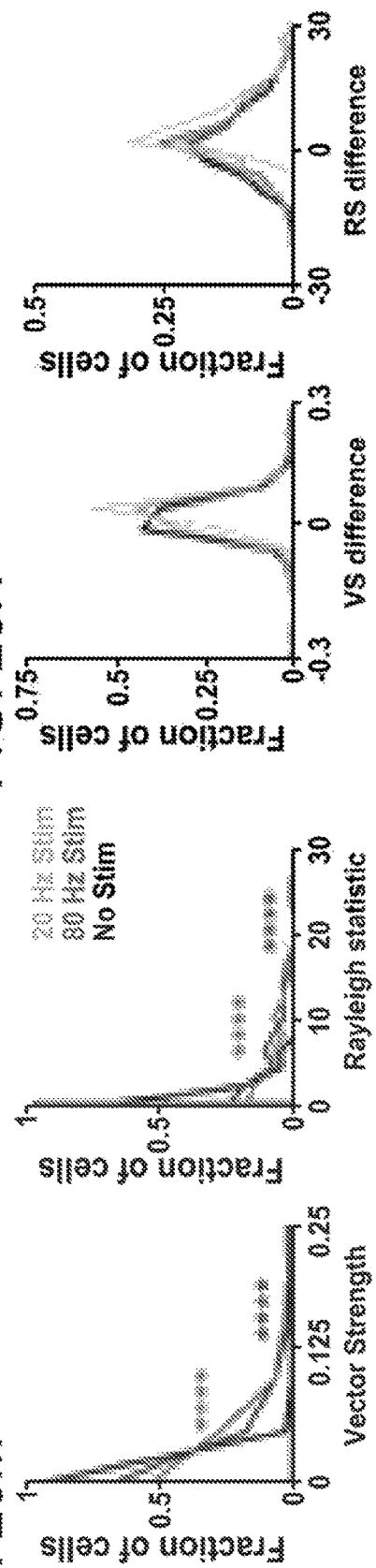
FIG. 26M shows the same as (26F) for CA1 (left, $P<0.0005$ 20 Hz vs. No Stim, 80 Hz vs. No Stim; Kolmogorov-Smirnov test; 16 units had 20 Hz stim VS values greater than 0.25; 7 units had 80 Hz stim VS values greater than 0.25; right, $P<0.0005$ 20 Hz vs. No Stim, 80 Hz vs. No Stim; Kolmogorov-Smirnov test; 21 units had 20 Hz stim RS values greater than 30; 3 units had 80 Hz stim RS values greater than 30).
Figure 26R:
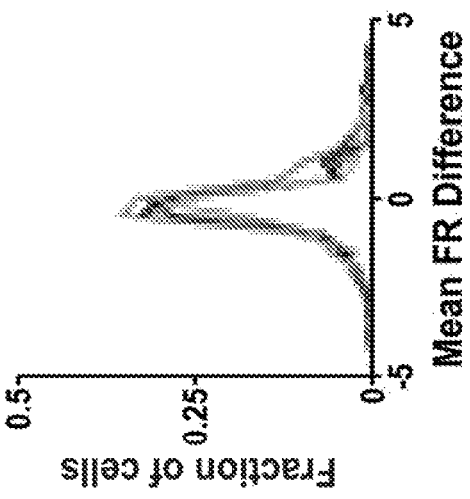
FIG. 26R shows the same as (26D) for mPFC ($P>0.01$ 40 Hz—no stimulation, n.s. after controlling for five comparisons; all others n.s.; Wilcoxon signed rank test for zero median).
Figure 26S:
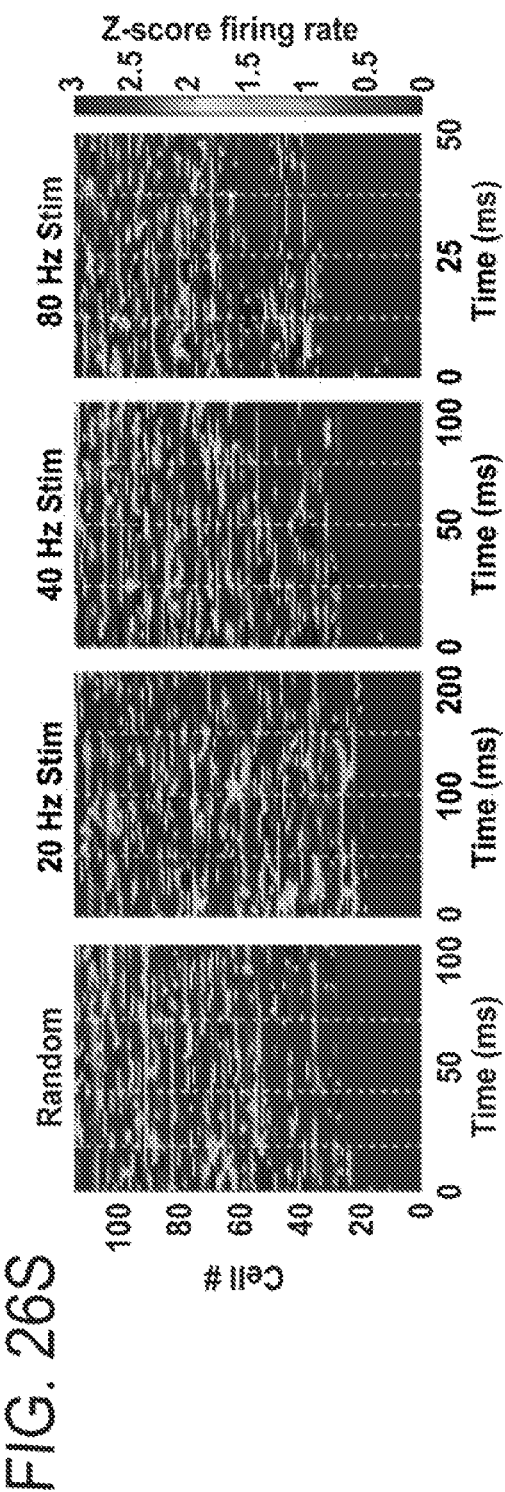
FIG. 26S shows the same as (26E) for mPFC.
Figure 26T:
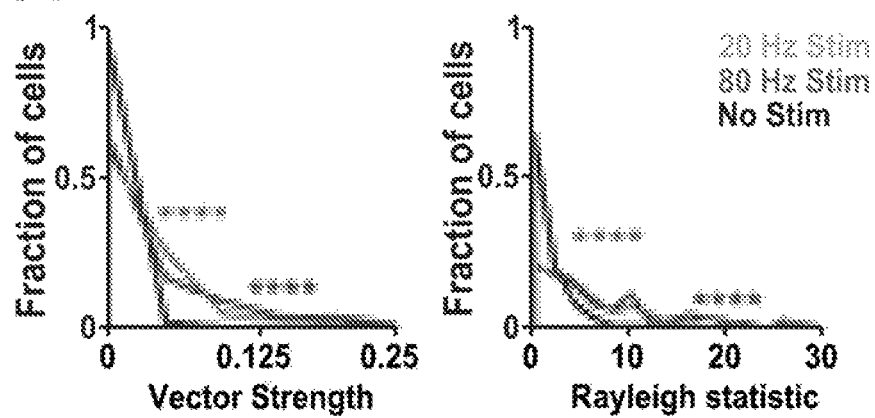
FIG. 26T shows the same as (26F) for mPFC (left, $P<0.00005$ 20 Hz vs. No Stim, 80 Hz vs. No Stim; Kolmogorov-Smirnov test; 4 units had 20 Hz stim VS values greater than 0.25; 1 unit had a 80 Hz stim VS value greater than 0.25; right, $P<0.00005$ 20 Hz vs. No Stim, 80 Hz vs. No Stim; Kolmogorov-Smirnov test; 5 units had 20 Hz stim RS values greater than 30; 1 unit had a 80 Hz stim RS value greater than 30).
Figure 26U:
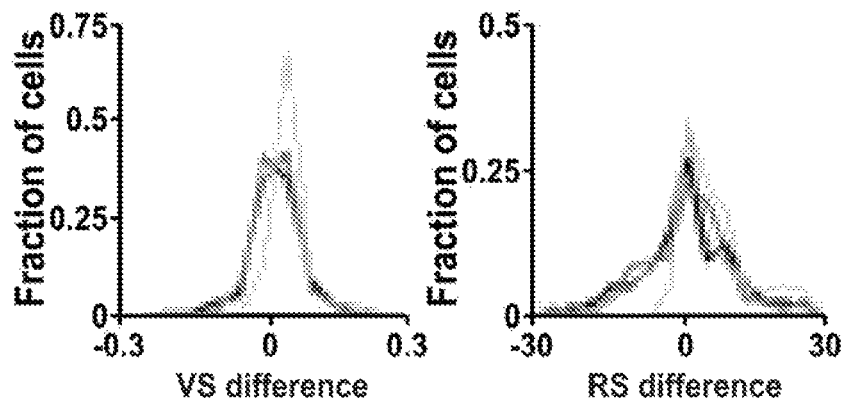

Combined auditory and visual GENUS induces a clustering phenotype response by microglia. Having shown that GENUS can be applied through both visual (Iaccarino et al., 2016) and auditory stimulation, next experiment aims to determine if a combination of 40 Hz auditory tone stimulation with 40 Hz light flicker (combined GENUS) entrain neural responses in AC, CA1, and mPFC and have stronger effects than either sensory modality alone. We presented 3-8 month old male wild-type (C57BL6J) mice with 1 ms-long auditory tones coupled with 12.5 ms-long light pulses (auditory plus visual, or A+V, stimulation) at 40 Hz while recording neural activity in AC, CA1, or mPFC using 32-channel silicon probes as animals ran or rested on a spherical treadmill (Methods). Single unit firing rate increased and decreased periodically with each tone and light-on period, thus entraining to 40 Hz during combined GENUS (FIG. 25A-C, left). Across AC, CA1, and mPFC, vector strength distributions were significantly higher, illustrating entrained spiking of single neurons to 40 Hz A+V, compared to random and no stimulation periods (FIG. 25A-C, right). Elevated power in the LFP at 40 Hz in AC, CA1, and mPFC was observed during 40 Hz A+V stimulation (FIGS. 26A, H, and O). Although the increase in LFP power was very small in mPFC, the median distribution of mean firing rate differences during A+V stimulation, compared to no stimulation, differed significantly from zero (FIG. 26O, R) whereas neither effects were seen in mPFC with auditory GENUS alone (FIG. 24P, R). Thus, combined tone plus light stimulation at 40 Hz induced GENUS in AC, CA1, and mPFC. Significant entrainment was also observed in all three regions with 20 Hz, 80 Hz, and random frequency A+V stimulation, although the latter did not induce periodic firing modulation (FIGS. 26B-G, I-N, P-U).

In one aspect, disclosed herein are methods of treating a neurological disease, injury, condition, or infection (such as, for example, Schizophrenia, Epilepsy, Frontotemporal dementia, vascular dementia, Bipolar disorder, Parkinson's disease, Alzheimer's disease, Autism, Amyotrophic Lateral Sclerosis, Stroke, Traumatic brain injury, bipolar disorder, ischemia reperfusion injury, Multiple sclerosis, and/or Depression) including inflammatory injury due to the neurological disease, injury, condition, or infection in a subject, comprising exposing the subject to a stimulus; the stimulus induces neural activity in the subject's brain and modulates expression of at least one soluble mediator of cellular activity within the subject, and the stimulus is delivered to the subject for less than one hour.

In one aspect, it is understood and herein contemplated that the stimulus used for treatment in the disclosed methods of treating a treating a neurological disease, injury, condition, or infection can be delivered for less than one hour in the disclosed methods. In one aspect, the less than one hour stimulus can be delivered as a single exposure or in 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 125, 130, 135, 140, 150 or more dosed exposures per day. Additionally, it is understood and herein contemplated that stimulus treatment can be administered at least once every 6, 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months. In one aspect, the treatment can be administered a single time or as needed to treat the neurological disease or condition. Thus, in one aspect, the treatment can occur for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 60 days, 3, 4, 5, 6, 7, 8, 9, 10, 11, 12, 13, 14, 15, 16, 17, 18, 19, 20, 21, 22, 23, 24 months, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 or more years. In one aspect, the treatment continues for the remainder of the life of the subject.

Also disclosed herein are methods of upregulating the expression of a soluble mediator of cellular activity in the brain of a subject comprising exposing a subject to a 40 Hz sensory flicker stimulus, a random sensory flicker stimulus, a constant sensory stimulus, or a combination thereof. In one aspect, disclosed herein are methods of upregulating the expression of a soluble mediator of cellular activity in the brain of a subject of any preceding aspect, wherein the method comprises exposing the cell to 40 Hz sensory flicker stimulus, and wherein the soluble mediator of cellular activity comprises IL-4, IL-7, GM-CSF, IL-12p70, IL-12p40, IFN-γ, LIF, TNF-α, MIP-1β, Eotaxin, MIG, GRO-α, IL-13, MCP-1, IL-1α, LIX, G-CSF, IL-1β, IL-3, IL-6, IL-15, RANTES, and/or M-CSF. In one aspect, disclosed herein are methods of upregulating the expression of a soluble mediator of cellular activity in the brain of a subject of any preceding aspect, wherein the method comprises exposing the cell to random sensory flicker stimulus, and wherein the soluble mediator of cellular activity comprises IL-10, MIG, GRO-α, LIX, G-CSF, IL-1β, IL-3, IL-6, IL-15, RANTES, and/or M-CSF. In one aspect, disclosed herein are methods of upregulating the expression of a soluble mediator of cellular activity in the brain of a subject of any preceding aspect, wherein the method comprises exposing the cell to a constant sensory stimulus, and wherein the soluble mediator of cellular activity comprises VEGF, IL-2, IL-5, IL-9, IL-13, MCP-1, IL-1α, and/or MIP-1α.

Also disclosed herein are methods of suppressing the expression of a soluble mediator of cellular activity in the brain of a subject comprising exposing a subject to constant or flickering light at 20 Hz.

DISCUSSION

Slow auditory click-train stimuli can elicit a synchronized, phase-locked spiking response from AC neurons although each click becomes more modulatory as the frequency increases. Consistent with these results, it was found that AC neurons entrain to tones repeating at 20 Hz, 40 Hz, and 80 Hz and that for faster frequencies, neurons fire in response to a smaller fraction and at a wider range of phases relative to individual tones. Although there is extensive evidence that CA1 and mPFC neurons can respond to sensory cues including auditory stimuli, it is shown for the first time that 40 Hz auditory, or A+V, stimulation elicits small but significant firing rate entrainment at 40 Hz in these brain regions (FIGS. 23B, H, and N and FIG. 25A-C). As in AC, single units in CA1 and mPFC show modulation and fired as a function of stimulus phase although they do not fire in response to every pulse. Weaker spiking modulation may be expected in HPC and mPFC as sensory inputs reach these regions through multiple indirect pathways which likely low-pass filter spiking entrainment.

Studies of rate coding show that neurons can encode click trains using firing rate without synchronizing to the stimulus. In each brain region, it was found that some neurons fire at a different rate depending on the frequency of the auditory train, although the population as a whole did not fire more or less to the different stimulation frequencies (FIGS. 23F, L, and R and FIGS. 26D, K, and R). Therefore, it is concluded that the observed changes—in microglia, astrocytes, vasculature, and amyloid levels, as well as behavioral performance—in response to 40 Hz auditory stimulation, but not other frequencies, cannot be explained by overall changes in firing rate.

Method and Materials.

Surgical Procedures.

Adult (2-3 month-old) mice were anesthetized with isoflurane and fixed in a stereotaxic frame. Ophthalmic ointment (Puralube Vet Ointment, Dechra) was applied to the eyes, and the scalp was shaved and sterilized with povidone-iodine (Dynarex) and 70% ethanol. A custom stainless steel headplate was fixed using dental cement (C&B Metabond, Parkell) and the target craniotomy site for LFP recordings was marked on the skull (in mm, from bregma: −2.0 anterior/posterior, +/−1.8 medial/lateral for targeting CA1, −2.0 to −3.0 anterior/posterior, +/−1.8 medial/lateral for targeting auditory cortex, and +1.3 to +1.4 anterior/posterior, +/−1.0 medial/lateral for targeting prefrontal cortex). A craniotomy was later performed in 3-8 month-old mice. The day before or day of the first recording session, craniotomies (200-500 μm diameter) were made by thinning the skull with a dental drill and then making a hole with a 27-gauge needle. When not recording, the craniotomy was sealed with a sterile silicon elastomer (Kwik-Sil WPI).

Electrophysiology Recordings.

During recordings, head-fixed animals ran on an air-floating 8-inch spherical treadmill. All animals had previously learned to maneuver on the treadmill until they were comfortable while occasionally receiving sweetened condensed milk (1:2 water dilution). Animals were on the ball for a maximum of 5 hours and had multiple periods of running and rest during this time. Single shank 32-channel probes (NeuroNexus) were advanced to the target location. Recording sites spanned 250 μm. For auditory cortex recordings, the probe was advanced at a 45° angle from vertical parallel to the coronal plane to a depth of 3-4.15 mm. A series of 50 ms tones of 5, 10, 15, and 20 kHz were presented to detect auditory response in the mean LFP. For CA1 recordings, the probe was advanced vertically through the craniotomy to a depth of 1.14-2.05 mm until hippocampal pyramidal layer electrophysiology characteristics were observed (large theta waves and sharp wave ripples, 150+μV spikes on multiple channels). For prefrontal cortex recordings, the probe was advanced at a 20° angle from vertical, at a 49° angle from the coronal plane to a depth of 1.48-2.15 mm. If data were collected at multiple depths during the same recording session; new depths were mapped in order to ensure the location of the recording sites remained in the target location (n=9 recording depths from 9 sessions in 5 mice for AC and 12 recording depths from 10 sessions in 5 mice for CA1, n=7 recording depths from 7 sessions in 4 mice for mPFC). Data were acquired with a sampling rate of 20 kHz using an Intan RHD2000 Evaluation System using a ground pellet as reference.

Auditory and Visual Stimuli for Electrophysiology Recordings.

Animals were presented with 10 s stimulation blocks interleaved with 10 s baseline periods. Stimulation blocks rotated between auditory-only or auditory and visual stimulation at 20 Hz, 40 Hz, 80 Hz, or with random stimulation (pulses were delivered with randomized inter-pulse intervals determined from a uniform distribution with an average interval of 25 ms). Stimuli blocks were interleaved to ensure the results observed were not due to changes over time in the neuronal response. 10 s long stimulus blocks were used to reduce the influence of onset effects, and to examine neural responses to prolonged rhythmic stimulation. All auditory pulses were 1 ms-long 10 kHz tones. All visual pulses were 50% duty cycle of the stimulation frequency (25 ms, 12.5 ms, or 6.25 ms in length). For combined stimulation, auditory and visual pulses were aligned to the onset of each pulse.

Prefrontal Cortex Histology.

During the final mPFC recording in each animal, the probe was coated with DiI and inserted to target depth. Mice were transcardially perfused with 4% paraformaldehyde in phosphate buffered saline (PBS) under anesthesia (isoflurane), and the brains were post-fixed overnight in 4% paraformaldehyde in 1×PBS. Brains were sectioned 100 μm thick with a Leica VT1000S vibratome (Leica). Sections were stained with 0.2% 1 mMol DAPI in 1×PBS and mounted onto microscopy slides with Vectashield mounting medium. Images were acquired on a Zeiss Axio Observer Z1 inverted epifluorescent microscope with the accompanying Zen Blue 2 software.

Spike Sorting and Single Unit Stability.

Spike detection and sorting was carried out using MountainSort automated spike sorting followed by manual curation based on visual inspection of waveforms and cross-correlograms. Prior to manual curation, quality thresholds were applied to only include units with peak SNR greater than or equal to 1, less than 10% overlap with noise, and greater than 95% isolation against other units which resulted in well-isolated single units. To account for periods of instability in the recordings during which single units were lost, stability criteria were applied such that only stable periods (no sudden loss of a single unit's firing rate) would be considered in analysis. Firing rate (FR) for each unit was computed over the course of the recording session. Firing rate was clustered into two distributions, low FR and high FR, using k-means clustering. For units with FR that dropped below 10% of the high FR mean, further analyses identified a stable recording period defined as the longest length of time that the FR was 2 standard deviations above the low FR mean.

LFP.

LFP was obtained by downsampling raw traces to 2 kHz and bandpass filtering between 1-300 Hz.

Power Spectrum.

Power spectral density analysis was performed using multitaper methods from the Chronux toolbox (time-bandwidth product=3, number of tapers=5). LFP traces were divided into 10 s trials of each stimulation condition. The average power spectral density was computed for each animal (within the same recording day and recording depth) over these trials, referencing to a ground pellet in saline above the skull. Power spectral density analysis was initially computed for all recording sites in AC, CA1, and mPFC. From each recording depth, the traces with the largest 40 Hz peak in response to 40 Hz flicker stimuli were included in the analysis. The per-depth traces displayed in the presented data had the largest 40 Hz peak in response to auditory flicker stimuli.

Firing During Flicker Stimulation.

The single unit peri-stimulus time histograms (PSTH) for each stimulus frequency encompassed two stimulus cycles $$\left(\text{where one cycle} = \frac{1}{\text{stimulus frequency}} \text{sec}\right),$$

with 10 bins per cycle, to show spiking across trains of stimuli. Displaying spiking modulation over multiple cycles is typical for displaying modulation by oscillations. PSTHs were computed for all single units by binning spikes for 1 stimulus cycles before and after the start of each light-on or audio-on pulse. No stimulation (baseline) histograms were calculated using randomly distributed pulse times, as in the random stimulation condition. Firing rate was computed in each bin by dividing the number of spikes per bin by the total time in that bin (the total number of pulses times the bin size). To quantify firing rate periodicity in relation to the stimulus frequency, the time interval between firing rate peaks was calculated for all single unit histograms. The peaks of each PSTH was the maximum firing rate within one stimulus interval. To quantify firing rate modulation by the stimulus and compute circular statistics, peri-stimulus spike times were converted into radians: (peri–stimulus spike time)*2π*(stimulus frequency) and vector strengths and Rayleigh statistics were computed. Vector strength was computed using methods from the CircStat toolbox; the Rayleigh statistic was computed using the equation $RS=2nVS^2$, where n is total spike count, and VS is vector strength (Berens, 2009), Ma et al. 2013). Differences in vector strength and Rayleigh statistic values were computed by taking the differences in these values between stimulus conditions for each unit. Heat maps showing the firing rate response to flicker for all recorded single units were computed over four consecutive stimulus cycles. In order to show the response of all neurons, we show four consecutive stimulus cycles of each stimulation period. To do this, we aligned the 10 s presentation periods of each stimulus condition, and then excluded the first 100 ms of each presentation period to prevent onset effects from obscuring entrainment. Then, we averaged spiking response over the next four stimulus cycles (200 ms for 20 Hz, 100 ms for 40 Hz, and 50 ms for 80 Hz) to obtain the firing rate response to flicker. Firing rate for each single unit was computed in 1 ms bins, smoothed with a gaussian windows proportional to each stimulus frequency $$\left(N = \frac{1}{\text{Stimulus frequency}} \text{sec}, \alpha = 3\right),$$

and z-scored. Neurons were aligned by their average stimulus phase preference in the analyzed four cycles.

Mean Firing Rate.

Mean firing rate was computed for each single unit for each stimulus condition. Only stable periods for each unit contributed to the mean FR calculation (see Spike sorting and single unit stability, above). Difference in mean firing rate between stimulus conditions was computed within each unit by taking the difference in mean FR in each condition for that unit.

REFERENCES

1. Iaccarino, H. F. et al. Gamma frequency entrainment attenuates amyloid load and modifies microglia. *Nature* (2016).
2. Stam, C. J. et al. Generalized Synchronization of MEG Recordings in Alzheimer's Disease: Evidence for Involvement of the Gamma Band. *J. Clin. Neurophysiol.* 19, 562-574 (2002).
3. Verret, L. et al. Inhibitory Interneuron Deficit Links Altered Network Activity and Cognitive Dysfunction in Alzheimer Model. *Cell* 149, 708-721 (2012).
4. Gillespie, A. K. et al. Apolipoprotein E4 Causes Age-Dependent Disruption of Slow Gamma Oscillations during Hippocampal Sharp-Wave Ripples. *Neuron* 1-12 (2016). doi:10.1016/j.neuron.2016.04.009
5. Eriksson, L. *Multi-and megavariate data analysis*. (MKS Umetrics AB, 2006).
6. Wood, L. B. et al. Identification of neurotoxic cytokines by profiling Alzheimer's disease tissues and neuron culture viability screening. *Sci Rep* 5, 16622 (2015).
7. Hanisch, U.-K. Microglia as a source and target of cytokines. *Glia* 40, 140-55 (2002).
8. Janes, K. A. et al. A systems model of signaling identifies a molecular basis set for cytokine-induced apoptosis. *Science* 310, 1646-1653 (2005).
9. Gierut, J. J. et al. Network-level effects of kinase inhibitors modulate TNF-alpha-induced apoptosis in the intestinal epithelium. *Sci Signal* 8, ra129 (2015).
10. Girardeau, G., Benchenane, K., Wiener, S. I., Buzsáki, G. & Zugaro, M. B. Selective suppression of hippocampal ripples impairs spatial memory. *Nat. Neurosci.* 12, 1222-1223 (2009).
11. Girardeau, G. & Zugaro, M. Hippocampal ripples and memory consolidation. *Curr. Opin. Neurobiol.* 21, 452-459 (2011).
12. Jadhav, S. P., Kemere, C., German, P. W. & Frank, L. M. Awake hippocampal sharp-wave ripples support spatial memory.e. *Science (80-.).* 336, 1454-8 (2012).
13. Carr, M. F., Jadhav, S. P. & Frank, L. M. Hippocampal replay in the awake state: a potential substrate for memory consolidation and retrieval. *Nat. Neurosci.* 14, 147-153 (2011).
14. Carr, M. F. F. F., Karlsson, M. P. P. P. & Frank, L. M. M. M. Transient Slow Gamma Synchrony Underlies Hippocampal Memory Replay. *Neuron* 75, 700-713 (2012).
15. Bahrami, S. & Drabløs, F. Gene regulation in the immediate-early response process. *Adv. Biol. Regul.* 62, 37-49 (2016).
16. Kaminska, B. MAPK signalling pathways as molecular targets for anti-inflammatory therapy—from molecular mechanisms to therapeutic benefits. *Biochim. Biophys. Acta* 1754, 253-62 (2005).
17. Rothschild, D. E., McDaniel, D. K., Ringel-Scaia, V. M. & Allen, I. C. Modulating inflammation through the negative regulation of NF-κB signaling. *J. Leukoc. Biol.* (2018). doi:10.1002/JLB.3MIR0817-346RRR
18. Allan, S. M. & Rothwell, N. J. Cytokines and acute neurodegeneration. *Nat. Rev. Neurosci.* 2, 734-44 (2001).
19. Dansokho, C. & Heneka, M. T. Neuroinflammatory responses in Alzheimer's disease. *J. Neural Transm.* (2017). doi:10.1007/s00702-017-1831-7
20. Wood, L. B., Winslow, A. R. & Strasser, S. D. Systems biology of neurodegenerative diseases. *Integr Biol* 7, 758-775 (2015).
21. Tischer, J. et al. Inhomogeneous distribution of Iba-1 characterizes microglial pathology in Alzheimer's disease. *Glia* 64, 1562-1572 (2016).
22. Keren-Shaul, H. et al. A Unique Microglia Type Associated with Restricting Development of Alzheimer's Disease. *Cell* 169, 1276-1290.e17 (2017).
23. Rehman, S. U. et al. Inhibition of c-Jun N-Terminal Kinase Protects Against Brain Damage and Improves Learning and Memory After Traumatic Brain Injury in Adult Mice. *Cereb. Cortex* 1-19 (2017). doi:10.1093/cercor/bhx164
24. Camer, D. et al. Bardoxolone methyl prevents high-fat diet-induced alterations in prefrontal cortex signalling molecules involved in recognition memory. *Prog. Neuro-Psychopharmacology Biol. Psychiatry* 59, 68-75 (2015).
25. Wang, Y.-Y., Yang, Y.-X., Zhe, H., He, Z.-X. & Zhou, S.-F. Bardoxolone methyl (CDDO-Me) as a therapeutic agent: an update on its pharmacokinetic and pharmacodynamic properties. *Drug Des. Devel. Ther.* 8, 2075-88 (2014).
26. Bennett, B. L. et al. SP600125, an anthrapyrazolone inhibitor of Jun N-terminal kinase. *Proc. Natl. Acad. Sci. U.S.A* 98, 13681-6 (2001).
27. Onai, Y. et al. Inhibition of IkappaB phosphorylation in cardiomyocytes attenuates myocardial ischemia/reperfusion injury. *Cardiovasc. Res.* 63, 51-9 (2004).
28. Rangaraju, S. et al. A systems pharmacology-based approach to identify novel Kv1.3 channel-dependent mechanisms in microglial activation. *J. Neuroinflammation* 14, 128 (2017).
29. Trapnell, C., Pachter, L. & Salzberg, S. L. TopHat: discovering splice junctions with RNA-Seq. *Bioinformatics* 25, 1105-1111 (2009).
30. Zhang, B. & Horvath, S. A general framework for weighted gene co-expression network analysis. *Stat. Appl. Genet. Mol. Biol.* 4, Article 17 (2005).
31. Seyfried, N. T. et al. A Multi-network Approach Identifies Protein-Specific Co-expression in Asymptomatic and Symptomatic Alzheimer's Disease. *Cell Syst.* 4, 60-72.e4 (2017).
32. Fries, P., Nikolić, D. & Singer, W. The gamma cycle. *Trends Neurosci.* 30, 309-16 (2007).
33. Buzsáki, G. *Rhythms of the brain*. (Oxford University Press, 2006).
34. Colgin, L. L. Rhythms of the hippocampal network. *Nat. Rev. Neurosci.* 17, 239-249 (2016).
35. O'Keefe, J. & Dostrovsky, J. The hippocampus as a spatial map. Preliminary evidence from unit activity in the freely-moving rat. Brain Research 34, (1971).
36. Dragoi, G. & Buzsaki, G. Temporal Encoding of Place Sequences by Hippocampal Cell Assemblies. *Neuron* 50, 145-157 (2006).
37. Skaggs, W. & McNaughton, B. Replay of neuronal firing sequences in rat hippocampus during sleep following spatial experience—ProQuest. *Science (80-.).* 271, 1870 (1996).
38. Foster, D. J. & Wilson, M. A. Reverse replay of behavioural sequences in hippocampal place cells during the awake state. *Nature* 440, 680-3 (2006).
39. Singer, A. C. & Frank, L. M. Rewarded outcomes enhance reactivation of experience in the hippocampus. *Neuron* 64, 910-21 (2009).
40. Singer, A. C., Carr, M. F., Karlsson, M. P. & Frank, L. M. Hippocampal SWR activity predicts correct decisions during the initial learning of an alternation task. *Neuron* 77, 1163-73 (2013).
41. Buzsaki, G. et al. Hippocampal network patterns of activity in the mouse. *Neuroscience* 116, 201-211 (2003).
42. Clemens, Z. et al. Temporal coupling of parahippocampal ripples, sleep spindles and slow oscillations in humans. *Brain* 130, 2868-78 (2007).
43. Logothetis, N. K. et al. Hippocampal-cortical interaction during periods of subcortical silence. *Nature* 491, 547-553 (2013).
44. Axmacher, N., Elger, C. E. & Fell, J. Ripples in the medial temporal lobe are relevant for human memory consolidation. *Brain* 131, 1806-17 (2008).
45. Rajasethupathy, P. et al. Projections from neocortex mediate top-down control of memory retrieval. *Nature* 526, 653-659 (2015).
46. Dombeck, D. A. & Reiser, M. B. Real neuroscience in virtual worlds. *Curr. Opin. Neurobiol.* 22, 3-10 (2012).

47. Ravassard, P. et al. Multisensory control of hippocampal spatiotemporal selectivity. *Science* (80-.). 340, 1342-6 (2013).
48. Karlsson, M. P. & Frank, L. M. Awake replay of remote experiences in the hippocampus. *Nat. Neurosci.* 12, 913-8 (2009).
49. Hasselmo, M. E. & Stern, C. E. Theta rhythm and the encoding and retrieval of space and time. *Neuroimage* 85 Pt 2, 656-66 (2014).
50. Nakazawa, K., McHugh, T. J., Wilson, M. A. & Tonegawa, S. NMDA receptors, place cells and hippocampal spatial memory. *Nat. Rev. Neurosci.* 5, 361-372 (2004).
51. Elmore, M. R. P. et al. Colony-Stimulating Factor 1 Receptor Signaling Is Necessary for Microglia Viability, Unmasking a Microglia Progenitor Cell in the Adult Brain. *Neuron* 82, 380-397 (2014).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for controlling brain activity in a subject, comprising:
   delivering a stimulus to the subject, wherein the stimulus is delivered to the subject for less than one hour;
   inducing, in response to the stimulus delivered to the subject, neural activity in the subject's brain;
   modulating, in response to the stimulus delivered to the subject, expression of at least one soluble mediator of cellular activity within the subject; and
   invoking, in response to the stimulus delivered to the subject, an immunomodulatory response in the subject, wherein the stimulus is a 20 Hz sensory flicker stimulus, and wherein the stimulus is at least one of a visual or auditory stimulus.

2. The method of claim 1, wherein the at least one soluble mediator of cellular activity comprise a cytokine, chemokine, or growth factor.

3. The method of claim 1, wherein the stimulus is delivered to the subject for less than about 30 minutes.

4. The method of claim 3, wherein the stimulus is delivered to the subject for less than about 10 minutes.

5. The method of claim 4, wherein the stimulus is delivered to the subject for less than about 5 minutes.

6. The method of claim 1, wherein the stimulus is a non-invasive stimulus.

7. The method of claim 1, further comprising:
   selecting a soluble mediator of cellular activity to modulate, wherein the at least one soluble mediator includes the selected soluble mediator; and
   selecting a stimulation protocol that modulates the selected soluble mediator of cellular activity, wherein the stimulus is delivered according to the selected stimulation protocol.

8. The method of claim 7, wherein the stimulation protocol is the 20 Hz sensory flicker stimulus.

9. The method of claim 1, wherein the at least one soluble mediator of cellular activity comprises Interleukin-4 (IL-4), Interleukin-7 (IL-7), Granulocyte-macrophage colony-stimulating factor (GM-CSF), Interleukin-12 p70 (IL-12p70), Interleukin-12 p40 (IL-12p40), Interferon-γ (IFN-γ), LIF, Tumor necrosis factor-α (TNF-α), Macrophage inflammatory protein 1β (MIP-1β), Eotaxin, Interleukin-10 (IL-10), vascular endothelial growth factor (VEGF), Interleukin-2 (IL-2), Interleukin-5 (IL-5), Interleukin-9 (IL-9), Macrophage inflammatory protein 1α (MIP-1α), monokine induced by gamma interferon (MIG), growth-regulated oncogene-α (GRO-α), LIX (CXCL5), granulocyte colony-stimulating factor (G-CSF), Interleukin-1β(IL-1β), Interleukin-3 (IL-3), Interleukin-6 (IL-6), Interleukin-15 (IL-15), Regulated upon Activation, Normal T cell Expressed, and Secreted (RANTES), macrophage colony-stimulating factor (M-CSF), Interleukin-13 (IL-13), monocyte chemoattractant protein 1 (MCP-1), and/or Interleukin-1α (IL-1α).

10. The method of claim 1, wherein the sensory flicker stimulus is a combined visual and auditory flicker stimulus.

11. The method of claim 1, wherein the brain activity is induced in at least one of the sensory cortices.

12. The method of claim 1, wherein the brain activity is induced in at least one of the hippocampus, medial temporal lobes, frontal lobes, subcortical structures, thalamus, hypothalamus, or brainstem.

13. The method of claim 1, wherein the stimulus drives neural activity in the subject's brain.

14. The method of claim 13, wherein the neural activity in the subject's brain is neural activity in a range between about 20 and 80 Hz.

15. The method of claim 1, further comprising treating at least one of disease, injury, infection, or normal aging in the subject's brain using the stimulus delivered to the subject.

16. The method of claim 1, wherein the method comprises treating a neurodegenerative disease using the stimulus delivered to the subject.

17. The method of claim 16, wherein the neurodegenerative disease is Alzheimer's disease, Parkinson's disease, dementia, frontotemporal dementia, vascular dementia, amyotrophic lateral sclerosis (ALS), or multiple sclerosis (MS).

18. The method of claim 1, wherein the method comprises treating a condition in the subject by modulating at least one of immunomodulatory signaling or cell survival signaling within the subject.

19. The method of claim 18, wherein the condition is epilepsy, schizophrenia, autism, traumatic brain injury (TBI), bipolar disorder, stroke, or depression.

20. The method of claim 1, wherein the method comprises inducing or suppressing neuroplasticity of the subject's brain using the stimulus delivered to the subject.

21. The method of claim 1, wherein the stimulus upregulates at least one intracellular signaling pathway.

22. The method of claim 21, wherein the at least one intracellular signaling pathway comprises a canonical kinase pathway.

23. The method of claim 21, wherein the at least one intracellular signaling pathway comprises mitogen activated protein kinase (MAPK) pathway, nuclear factor kappa-light-chain-enhancer of activated B cells (NFκB) pathway, Cyclooxygenase-2 (COX-2) pathway, Nuclear factor (erythroid-derived 2)-like 2 (Nrf2) pathway, Phosphatidylinositol-4,5-bisphosphate 3-kinase (P13K)/Akt pathway, or Janus kinase (JAK)-Signal Transducer and Activator of Transcription (STAT) pathway.

24. The method of claim 1, wherein the stimulus effects on intracellular signaling modulate expression or activity of at least one immediate early gene.

25. The method of claim 24, wherein the at least one immediate early gene is activity-regulated cytoskeleton-associated protein (ARC) or Fos proto-oncogene (C-Fos).

26. The method of claim 1, wherein the stimulus modulates intracellular signaling that regulates differentiation.

27. A method of treating a neurological condition in a subject, comprising:
- exposing the subject to a stimulus, wherein the stimulus is delivered to the subject for less than one hour;
- inducing, in response to the stimulus exposed to the subject, neural activity in the subject's brain; and
- modulating, in response to the stimulus exposed to the subject, expression of at least one soluble mediator of cellular activity within the subject, wherein the stimulus is a 20 Hz sensory flicker stimulus, and wherein the stimulus is at least one of a visual or auditory stimulus.

28. The method of claim 27, wherein the neurological condition comprises Schizophrenia, Epilepsy, Frontotemporal dementia, vascular dementia, Bipolar disorder, Parkinson's disease, Alzheimer's disease, Amyotrophic Lateral Sclerosis, Stroke, Traumatic brain injury, Multiple sclerosis, or Depression.

29. The method of claim 27, wherein the neurological condition is depression.

30. The method of claim 27, wherein the neurological condition comprises inflammatory damage resulting from aging, traumatic brain injury, stress, schizophrenia, and/or depression.

* * * * *